(12) United States Patent
Goetz et al.

(10) Patent No.: US 8,751,007 B2
(45) Date of Patent: Jun. 10, 2014

(54) SHIFTING BETWEEN ELECTRODE COMBINATIONS IN ELECTRICAL STIMULATION DEVICE

(75) Inventors: Steven M. Goetz, Brooklyn Center, MN (US); Andrew H. Houchins, Lino Lakes, MN (US); Jeffrey T. Keacher, St. Paul, MN (US); Gary W. King, Fridley, MN (US); Kenneth T. Heruth, Edina, MN (US); Roy L. Testerman, New Hope, MN (US); Michael T. Lee, Minnetonka, MN (US); Nathan A. Torgerson, Andover, MN (US); Joseph J. Nolan, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/251,911
(22) Filed: Oct. 3, 2011

(65) Prior Publication Data
US 2012/0022614 A1    Jan. 26, 2012

Related U.S. Application Data

(63) Continuation of application No. 13/152,870, filed on Jun. 3, 2011, which is a continuation of application No. 12/406,607, filed on Mar. 18, 2009, now Pat. No. 7,974,703, which is a continuation of application No. 11/401,100, filed on Apr. 10, 2006, now Pat. No. 7,519,431, which is a continuation-in-part of application No. 11/352,389, filed on Feb. 10, 2006, now abandoned.

(60) Provisional application No. 60/670,059, filed on Apr. 11, 2005.

(51) Int. Cl.
*A61N 1/08* (2006.01)
*A61N 1/372* (2006.01)

(52) U.S. Cl.
CPC .................................. *A61N 1/37247* (2013.01)
USPC ............................................... 607/59; 607/30

(58) Field of Classification Search
CPC ........... A61N 1/37211; A61N 1/37235; A61N 1/37241; A61N 1/37247; A61N 1/37252; A61N 1/37264
USPC .................... 607/30, 31, 32, 59, 66
See application file for complete search history.

(56) References Cited

U.S. PATENT DOCUMENTS

| 4,803,988 A | 2/1989 | Thomson |
| 4,813,418 A | 3/1989 | Harris |

(Continued)

FOREIGN PATENT DOCUMENTS

| EP | 0 811 395 | 12/1997 |
| EP | 1 145 731 | 10/2001 |

(Continued)

OTHER PUBLICATIONS

Notification of Transmittal of the International Search Report and the Written Opinion for corresponding PCT application No. PCT/US2006/004861 dated Aug. 3, 2006 (15 pgs.).

(Continued)

*Primary Examiner* — Christopher D Koharski
*Assistant Examiner* — Frances Oropeza
(74) *Attorney, Agent, or Firm* — Shumaker & Sieffert, P.A.

(57) ABSTRACT

The disclosure is directed to techniques for shifting between two electrode combinations. An amplitude of a first electrode combination is incrementally decreased while an amplitude of a second, or subsequent, electrode combination is concurrently incrementally increased. Alternatively, an amplitude of the first electrode combination is maintained at a target amplitude level while the amplitude of the second electrode combination is incrementally increased. The stimulation pulses of the electrode combinations are delivered to the patient interleaved in time. In this manner, the invention provides for a smooth, gradual shift from a first electrode combination to a second electrode combination, allowing the patient to maintain a continual perception of stimulation. The shifting techniques described herein may be used during programming to shift between different electrode combinations to find an efficacious electrode combination. Additionally, the techniques may be used for shifting between different electrode combinations associated with different stimulation programs or program sets.

35 Claims, 37 Drawing Sheets

(56) References Cited

U.S. PATENT DOCUMENTS

| | | | |
|---|---|---|---|
| 4,977,895 | A | 12/1990 | Tannenbaum |
| 5,002,053 | A | 3/1991 | Garcia-Rill et al. |
| 5,014,705 | A | 5/1991 | Graupe et al. |
| 5,052,391 | A | 10/1991 | Silberstone et al. |
| 5,081,989 | A | 1/1992 | Graupe et al. |
| 5,117,826 | A | 6/1992 | Bartelt et al. |
| 5,143,089 | A | 9/1992 | Alt |
| 5,215,086 | A | 6/1993 | Terry, Jr. et al. |
| 5,314,458 | A | 5/1994 | Najafi et al. |
| 5,330,515 | A | 7/1994 | Rutecki et al. |
| 5,335,657 | A | 8/1994 | Terry, Jr. et al. |
| 5,354,320 | A | 10/1994 | Schaldach et al. |
| 5,387,231 | A | 2/1995 | Sporer |
| 5,417,719 | A | 5/1995 | Hull et al. |
| 5,423,877 | A | 6/1995 | Mackey |
| 5,443,486 | A | 8/1995 | Hrdlicka et al. |
| 5,458,625 | A | 10/1995 | Kendall |
| 5,458,626 | A | 10/1995 | Krause |
| 5,540,730 | A | 7/1996 | Terry, Jr. et al. |
| 5,562,276 | A | 10/1996 | Blick |
| 5,562,718 | A | 10/1996 | Palermo |
| 5,569,166 | A | 10/1996 | Stone |
| 5,643,329 | A | 7/1997 | Solomonow et al. |
| 5,643,330 | A | 7/1997 | Holsheimer et al. |
| 5,662,691 | A | 9/1997 | Behan et al. |
| 5,716,377 | A | 2/1998 | Rise et al. |
| 5,716,384 | A | 2/1998 | Snell |
| 5,785,043 | A * | 7/1998 | Cyrus et al. ............ 600/525 |
| 5,938,690 | A | 8/1999 | Law et al. |
| 6,002,966 | A | 12/1999 | Loeb et al. |
| 6,052,624 | A | 4/2000 | Mann |
| 6,219,580 | B1 | 4/2001 | Faltys et al. |
| 6,304,787 | B1 | 10/2001 | Kuzma et al. |
| 6,308,102 | B1 | 10/2001 | Sieracki et al. |
| 6,345,202 | B2 | 2/2002 | Richmond et al. |
| 6,355,031 | B1 | 3/2002 | Edwards et al. |
| 6,381,496 | B1 | 4/2002 | Meadows et al. |
| 6,393,325 | B1 * | 5/2002 | Mann et al. ............ 607/46 |
| 6,516,227 | B1 | 2/2003 | Meadows et al. |
| 6,529,195 | B1 | 3/2003 | Eberlein |
| 6,580,948 | B2 | 6/2003 | Haupert et al. |
| 6,587,724 | B2 | 7/2003 | Mann |
| 6,609,031 | B1 | 8/2003 | Law et al. |
| 6,609,032 | B1 | 8/2003 | Woods et al. |
| 6,654,642 | B2 | 11/2003 | North et al. |
| 6,731,986 | B2 | 5/2004 | Mann |
| 6,748,276 | B1 | 6/2004 | Daignault, Jr. et al. |
| 6,856,315 | B2 | 2/2005 | Eberlein |
| 6,909,917 | B2 | 6/2005 | Woods et al. |
| 7,359,751 | B1 * | 4/2008 | Erickson et al. ............ 607/27 |
| 7,519,431 | B2 | 4/2009 | Goetz et al. |
| 2001/0007950 | A1 | 7/2001 | North et al. |
| 2002/0150679 | A1 | 10/2002 | Minami et al. |
| 2003/0135248 | A1 | 7/2003 | Stypulkowski |
| 2003/0171789 | A1 | 9/2003 | Malek et al. |
| 2004/0147978 | A1 | 7/2004 | Bernhard et al. |
| 2004/0158298 | A1 | 8/2004 | Gliner et al. |
| 2004/0215286 | A1 | 10/2004 | Stypulkowski |
| 2004/0215288 | A1 | 10/2004 | Lee et al. |

FOREIGN PATENT DOCUMENTS

| | | |
|---|---|---|
| EP | 1 145 735 | 10/2001 |
| EP | 1 145 736 | 10/2001 |
| WO | WO 97/49452 | 12/1997 |
| WO | WO 02/073526 | 9/2002 |
| WO | WO 03/059441 | 7/2003 |
| WO | WO 2004/093984 | 11/2004 |

OTHER PUBLICATIONS

Notification of Transmittal of the International Search Report and the Written Opinion for corresponding PCT application No. PCT/US2006/013379 dated Aug. 4, 2006 (17 pgs.).

Notification Concerning Transmittal of International Preliminary Report on Patentability for PCT/US2006/004861, dated Oct. 25, 2007 (10 pgs.).

Notification of Transmittal of the International Preliminary Report on Patentability for corresponding PCT/US2006/013379, dated May 10, 2007 (21 pgs.).

Reply to Written Opinion for corresponding PCT/US2006/013379, dated Feb. 9, 2007 (28 pgs.).

U.S. Appl. No. 12/392,876, filed Feb. 25, 2009 entitled: Shifting Between Electrode Combinations in Electrical Stimulation Device.

Office Action dated Sep. 29, 2010 for U.S. Appl. No. 12/392,876, (8 pgs.).

Responsive Amendment dated Dec. 23, 2010 for U.S. Appl. No. 12/392,876, (18 pgs.).

U.S. Appl. No. 12/406,607, filed Mar. 18, 2009 entitled: Shifting Between Electrode Combinations in Electrical Stimulation Device.

Office Action dated Sep. 29, 2010 for U.S. Appl. No. 12/406,607, (9 pgs.).

Responsive Amendment dated Dec. 23, 2010 for U.S. Appl. No. 12/406,607, (14 pgs.).

Response to Office Action mailed Jun. 5, 2013, from U.S. Appl. No. 13/251,925, filed Sep. 5, 2013, 11 pp.

Office Action from U.S. Appl. No. 13/251,925, dated Jun. 5, 2013, 8 pp.

Office Action from U.S. Appl. No. 13/251,925, dated Oct. 31, 2013, 10 pp.

Response to Office Action dated Oct. 31, 2013, from U.S. Appl. No. 13/251,925, filed Dec. 19, 2013, 6 pp.

Notice of Allowance from U.S. Appl. No. 13/251,925, dated Jan. 13, 2014, 6 pp.

* cited by examiner

SHIFTING BETWEEN ELECTRODE COMBINATIONS IN ELECTRICAL STIMULATION DEVICE

This application is a continuation of U.S. application Ser. No. 13/152,870 filed on Jun. 3, 2011, which is a continuation of U.S. application Ser. No. 12/406,607, filed Mar. 18, 2009, which is a continuation of U.S. application Ser. No. 11/401,100, filed Apr. 10, 2006 (issued Apr. 14, 2009 as U.S. Pat. No. 7,519,431), which is a continuation-in-part of U.S. application Ser. No. 11/352,389, filed Feb. 10, 2006, which claims the benefit of U.S. provisional application No. 60/670,059, filed Apr. 11, 2005. This application claims the benefit of the above-identified applications. The entire content of each of the above applications is incorporated herein by reference.

TECHNICAL FIELD

The invention relates to neurostimulation therapy and, more particularly, to selection of electrode combinations for delivery of neurostimulation therapy to a patient.

BACKGROUND

Implantable neurostimulators may be used to deliver neurostimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver neurostimulation therapy via leads that include electrodes located proximate to the spinal cord, pelvic nerves, stomach, or within the brain of a patient. In general, the implantable medical device delivers neurostimulation therapy in the form of electrical pulses.

A clinician selects values for a number of programmable parameters in order to define the neurostimulation therapy to be delivered to a patient. For example, the clinician selects an amplitude, which may be a current or voltage amplitude, and pulse width for a stimulation waveform to be delivered to the patient, as well as a rate at which the pulses are to be delivered to the patient. The clinician may also select particular electrodes within an electrode set to be used to deliver the pulses and the polarities of the selected electrodes. A group of parameter values may be referred to as a program in the sense that they drive the neurostimulation therapy to be delivered to the patient.

The process of selecting values for the parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician typically needs to test a large number of possible electrode combinations within the electrode set implanted in the patient, in order to identify an optimal combination of electrodes and associated polarities. An electrode combination is a selected subset of one or more electrodes located on one or more implantable leads coupled to an implantable neurostimulator. As a portion of the overall parameter selection process, the process of selecting electrodes and the polarities of the electrodes can be particularly time-consuming and tedious.

In some cases, the clinician may test electrode combinations by manually specifying each combination based on intuition or some idiosyncratic methodology. The clinician may then record notes on the efficacy and side effects of each combination after delivery of stimulation via that combination. In this manner, the clinician is able to later compare and select from the tested combinations. As an example of the magnitude of the task, an implantable neurostimulator commonly delivers spinal cord stimulation therapy (SCS) to a patient via two leads that include eight electrodes per lead, which equates to over 43 million potential electrode combinations.

In order to improve the efficacy of neurostimulation therapy, neurostimulators have grown in capability and complexity. Modern neurostimulators tend to have larger numbers of electrode combinations, larger parameter ranges, and the ability to simultaneously deliver multiple therapy configurations by interleaving stimulation pulses in time. Although these factors increase the clinician's ability to adjust therapy for a particular patient or disease state, the burden involved in optimizing the device parameters has similarly increased. Unfortunately, fixed reimbursement schedules and scarce clinic time present challenges to effective programming of neurostimulator therapy.

SUMMARY

In general, the disclosure is directed to techniques for shifting stimulation energy between electrode combinations in an implantable neurostimulator. An electrode combination is a selected subset of one or more electrodes located on one or more implantable leads coupled to an implantable neurostimulator. The electrode combination also refers to the polarities of the electrodes in the selected subset. In the implantable neurostimulator, neurostimulation energy is delivered to different electrode combinations on a time-interleaved basis.

The techniques described herein may be used during a test or evaluation mode to shift between different electrode combinations in an effort to identify efficacious electrode combinations. Additionally, the techniques may be used for shifting between different electrode combinations associated with different stimulation programs or program sets during an operational mode. In either case, the neurostimulator gradually transitions from a first electrode combination to a second electrode combination in incremental steps.

For example, the neurostimulator or programmer may incrementally decrease an amplitude of a first electrode combination over a series of time slots while concurrently increasing an amplitude of a second electrode combination over a series of alternating time slots. Alternatively, the amplitude of the first electrode combination may be maintained at a target level while the amplitude of the second electrode combination is incrementally increased. Then, the amplitude of the first electrode combination may be incrementally decreased after the amplitude of the second electrode combination has reached the target level. In either case, the stimulator interleaves the stimulation pulses provided by the first and second electrode combinations in time at a sufficiently high frequency so that the patient perceives the physiological effects of the stimulation energy as smooth, or nearly simultaneous or overlapping in time. Each time slot may include a single pulse or multiple pulses from a given electrode combination.

In this manner, the time-interleaved stimulation energy is effective in simulating a continuous shifting of voltage or current amplitude from one electrode combination to another. The amplitudes of the first and second electrode combinations are ramped downward and upward, respectively, in incremental steps until the amplitude of the second electrode combination reaches a target amplitude. Alternatively, the second electrode combination may be ramped upward while the first electrode combination is held constant, followed by ramping the first electrode combination downward while the second electrode combination is held constant. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off.

In a test mode, the shifting process between successive electrode combinations may proceed under user control. In one embodiment, each incremental step in the transition may be contingent on input from a user, such as a physician or the patient. For example, the programmer may perform each incremental step in the shift in response to user input. In another embodiment, the programmer may proceed through all of the incremental steps automatically unless it receives input from the user. During the test mode, the user may mark stimulation parameters and electrode combinations that are found to be particularly efficacious.

User control may proceed in a time- or sequence-domain, with the user advancing and reversing the shift progression in terms of the time of an increment over a course of time, or the position of an increment within a sequence of defined increments. For example, the user controls may present a time-domain metaphor, such as that found within compact disc players, or audio or video tape players, where the user has access to input controls similar to play, stop, pause, rewind, and fast forward. Alternatively, user control may proceed in a planar domain, with the user selecting steps up, down, left or right.

In one embodiment, the disclosure provides a method comprising delivering electrical stimulation to a patient via a first electrode combination, delivering electrical stimulation to the patient via a second electrode combination on a time-interleaved basis with the electrical stimulation delivered via the first electrode combination, incrementally increasing an amplitude of the electrical stimulation delivered via the second electrode combination while the electrical stimulation delivered via the second electrode combination is delivered on a time-interleaved basis with the electrical stimulation delivered via the first electrode combination, and incrementally decreasing an amplitude of the electrical stimulation delivered via the first electrode combination while the electrical stimulation delivered via the second electrode combination is delivered on a time-interleaved basis with the electrical stimulation delivered via the first electrode combination.

The amplitude of the electrical stimulation delivered via the first electrode combination may be maintained, e.g., at a target level, while the amplitude of the electrical stimulation delivered via the second electrode combination is incrementally increased. Alternatively, the amplitude of the electrical stimulation delivered via the first electrode combination may be incrementally decreased while the amplitude of the stimulation delivered via the second electrode combination is incrementally increased.

In another embodiment, the disclosure provides a system comprising a medical device that includes one or more electrodes, a pulse generator to deliver electrical stimulation via the electrodes, and a switch device to couple the stimulation to selected electrodes. The system also comprises a programmer that programs the medical device, wherein the programmer controls the medical device to deliver electrical stimulation to a patient via a first electrode combination, deliver electrical stimulation to the patient via a second electrode combination on a time-interleaved basis with the electrical stimulation delivered via the first electrode combination, incrementally increase an amplitude of the electrical stimulation delivered via the second electrode combination while the electrical stimulation delivered via the second electrode combination is delivered on a time-interleaved basis with the electrical stimulation delivered via the first electrode combination, and incrementally decrease an amplitude of the electrical stimulation delivered via the first electrode combination while the electrical stimulation delivered via the second electrode combination is delivered on a time-interleaved basis with the electrical stimulation delivered via the first electrode combination.

In an additional embodiment, the disclosure provides a medical device comprising one or more implantable leads that include a plurality of electrodes, and a pulse generator to deliver stimulation energy, a switch device to couple the stimulation energy to selected electrodes. The medical device further comprises a processor to control the pulse generator and the switch device to deliver stimulation to the patient in accordance with a plurality of programs. The processor controls the pulse generator and the switch device to deliver electrical stimulation to a patient via a first electrode combination, deliver electrical stimulation to the patient via a second electrode combination on a time-interleaved basis with the electrical stimulation delivered via the first electrode combination, incrementally increase an amplitude of the electrical stimulation delivered via the second electrode combination while the electrical stimulation delivered via the second electrode combination is delivered on a time-interleaved basis with the electrical stimulation delivered via the first electrode combination, and incrementally decrease an amplitude of the electrical stimulation delivered via the first electrode combination while the electrical stimulation delivered via the second electrode combination is delivered on a time-interleaved basis with the electrical stimulation delivered via the first electrode combination.

In another embodiment, the disclosure provides a programmer comprising a processor that generates instructions to control an implantable pulse generator and deliver stimulation to a patient in accordance with a plurality of program. The instructions direct delivery of electrical stimulation to a patient via a first electrode combination, delivery of electrical stimulation to the patient via a second electrode combination on a time-interleaved basis with the electrical stimulation delivered via the first electrode combination, incremental increases in an amplitude of the electrical stimulation delivered via the second electrode combination while the electrical stimulation delivered via the second electrode combination is delivered on a time-interleaved basis with the electrical stimulation delivered via the first electrode combination, and incremental decreases in an amplitude of the electrical stimulation delivered via the first electrode combination while the electrical stimulation delivered via the second electrode combination is delivered on a time-interleaved basis with the electrical stimulation delivered via the first electrode combination. The programmer further comprises a telemetry interface to transmit the instructions to the implantable pulse generator.

In another embodiment, the disclosure provides a system comprising an medical device that includes one or more implantable leads that include a plurality of electrodes, a pulse generator to deliver electrical stimulation, and a switch device to couple the stimulation to selected electrodes. The system further comprises a programmer that programs the medical device, wherein the programmer controls the medical device to deliver electrical stimulation to a patient via a first electrode combination, deliver electrical stimulation to the patient via a second electrode combination on a time-interleaved basis with the stimulation delivered via the first electrode combination, and incrementally shift the delivery of stimulation from the first electrode combination to the second electrode combination.

In an additional embodiment, the disclosure provides a medical device comprising one or more implantable leads that include a plurality of electrodes, a pulse generator to deliver stimulation energy, a switch device to couple the stimulation energy to selected electrodes, and a processor to control the pulse generator and the switch device to deliver stimulation to the patient in accordance with a plurality of programs, wherein the processor controls the pulse generator and the switch device to deliver stimulation to the patient via a first electrode combination and to deliver electrical stimulation to the patient via a second electrode combination on a time-interleaved basis with the stimulation delivered via the first electrode combination, and wherein the processor incrementally shifts the delivery of stimulation from the first electrode combination to the second electrode combination.

In another embodiment, the disclosure provides a programmer comprising a memory that stores a first electrode combination and a second electrode combination, and a processor that controls delivery of electrical stimulation to a patient via the first electrode combination, delivery of electrical stimulation to the patient via the second electrode combination on a time-interleaved basis with the electrical stimulation via the first electrode combination, and incremental shifting of the delivery of electrical stimulation from the first electrode combination to the second electrode combination.

In a further embodiment, the disclosure provides computer-readable media comprising instructions that cause a processor to perform any of the techniques described in this disclosure.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
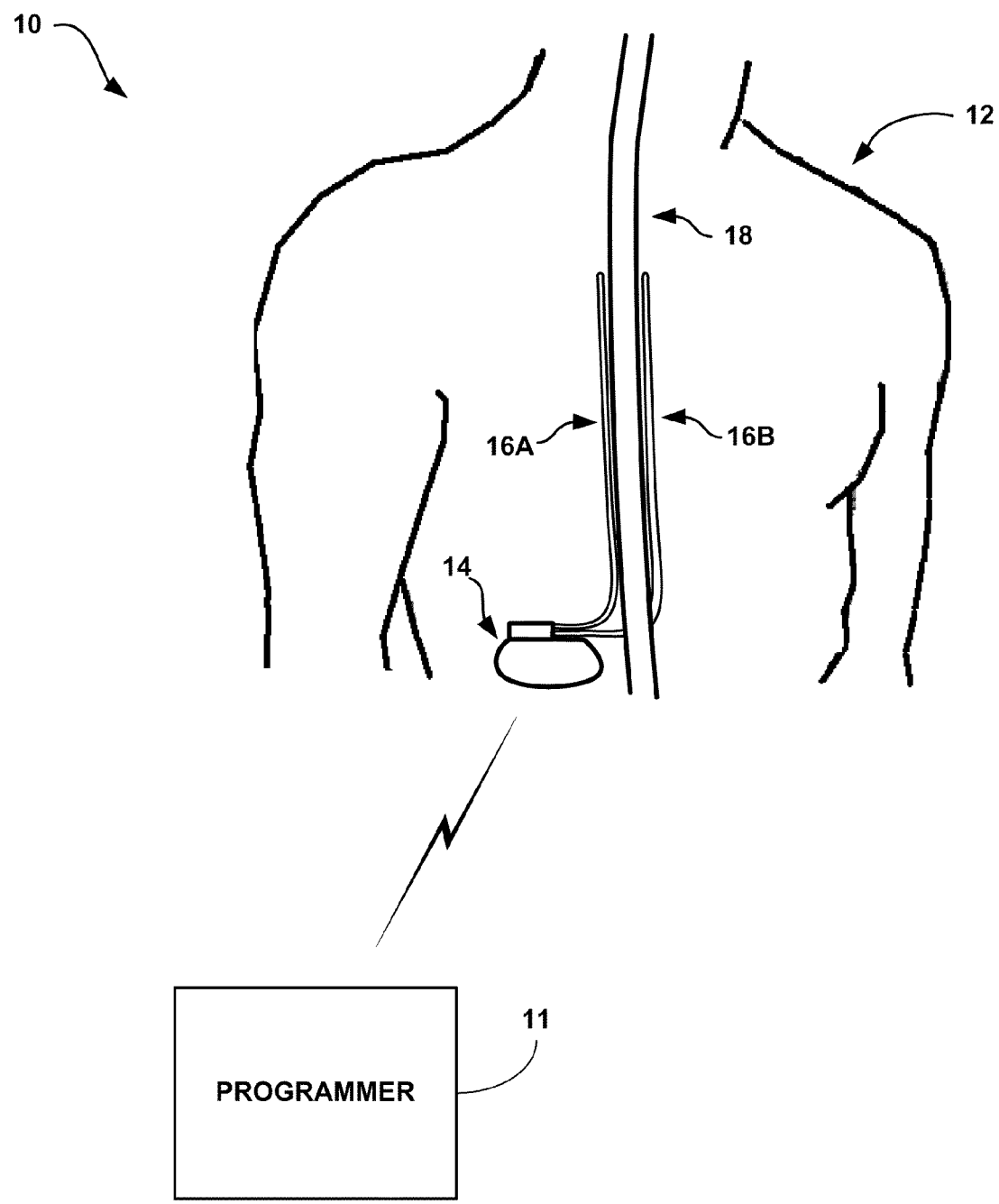
FIG. 1 is a schematic diagram illustrating an exemplary system for delivery and programming of neurostimulation therapy.

In general, the invention is directed to techniques for shifting between two electrode combinations during delivery of neurostimulation energy on a time-interleaved basis. An electrode combination is a selected subset of one or more electrodes located on one or more implantable leads coupled to an implantable neurostimulator. The electrode combination also refers to the polarities of the electrodes in the selected subset. As an illustration, if two leads are provided, and one lead carries electrodes 0 through 7, and another lead carries electrodes 8-15, one simple electrode combination is a combination of electrodes 6 and 7, with electrode 6 as a cathode and electrode 7 as an anode. Another example electrode combination is electrodes 6, 7 and 14, with electrodes 6 and 7 as anodes and electrode 14 as a cathode. Any number and polarity of electrodes may be selected as an electrode combination, provided there is at least one anode and at least one cathode.

The techniques described herein may be used during a programming test mode, e.g., within a clinic, to shift between different electrode combinations in an effort to identify efficacious electrode combinations for a patient who has been selected as a candidate for stimulation therapy. Also, the techniques may be used in a screening mode in which the patient is evaluated for chronic implantation of a stimulator. Additionally, the techniques may be used for shifting between different electrode combinations associated with different stimulation programs or program sets in an operational mode, i.e., in normal usage by the patient after programming of an implanted stimulator. In each case, the implanted stimulator gradually shifts from a first electrode combination to a second electrode combination, and so forth, in incremental steps.

As will be described, in accordance with some embodiments, a stimulator incrementally shifts voltage or current amplitude between electrode combinations in alternating time intervals, i.e., time slots, delivered on a time-interleaved basis. Each time slot may include one or more pulses of stimulation energy delivered via one electrode combination. Hence, in a first time slot, one or more stimulation pulses are delivered via a first electrode combination and, in a second time slot, one or more stimulation pulses are delivered via a second electrode combination. Depending on the length of the time slot, and the pulse width and pulse rate of the stimulation energy, a time slot may contain one pulse or many pulses. The testing of programming of electrode combinations can be accelerated to improve the chances of identifying an electrode combination and parameter settings that yield efficacious therapy. For SCS involving two leads with eight electrodes each, the number of electrode combination possibilities is well over 43 million. By directing the stimulator through a series of incremental voltage or current amplitude shifts, the speed and ease with which electrode combinations may be tried is increased.

The incremental shifting of voltage or current amplitude may be controlled automatically or in response to user input. The user input may specify incremental forward advancement or reversal of amplitude shifting among a series of successive electrode combinations. Alternatively, or additionally, the user input may specify a directional transition from one electrode combination to another. In each case, the incremental shifting of voltage or current amplitude is simulated by delivering stimulation energy to different electrode combinations in alternating, time-interleaved time slots. For example, individual stimulation pulses may be applied to different electrode combinations on an alternating, time-interleaved basis. Alternatively, groups of stimulation pulses may be applied to different electrode combinations in alternating, time-interleaved time slots. In this manner, a single stimulation pulse generator may be, in effect, multiplexed across the electrode combinations. However, the use of multiple stimulation pulse generators to deliver stimulation energy to different electrode combinations is also possible.

The amplitude shifting techniques described in this disclosure may provide a rapid way to scan electrode combinations across a lead or set of leads, allowing the therapeutic effects of the lead to be quickly evaluated. As an example, a clinician may start with a bipolar electrode combination at the distal end of a lead and then direct the stimulator to incrementally select other bipolar electrode combinations along the length of the lead, e.g., from the distal end to the proximal end. In this manner, the clinician does not need to reset the amplitude and electrode combination for every step of the process.

In addition, the amplitude shifting techniques may provide an efficient way to explore the electrode space defined by a given lead or lead set, allowing many neighboring therapy options to be tried in quick succession. For example, the clinician may select a combination of electrodes and then shift the chosen combination up or down a lead, or left and right between adjacent leads, while the patient reports perceived efficacy of the combinations, including side effects, if applicable. Again, a voltage or current amplitude is applied to electrode combinations in alternating, time-interleaved time slots to simulate gradual amplitude shifting between the successive electrode combinations. Notably, the shifting may proceed in forward or reverse so that the clinician may quickly revisit an electrode combination, if desired.

The simulation of gradual shifting over a series of time-interleaved time slots avoids a sudden, full-amplitude jump from one electrode combination to another, which could be disconcerting to the patient. Instead, amplitudes applied to electrode combinations during transition from one electrode to another are incrementally adjusted to produce a sensation of gradual transition for the patient. In this manner, a programming clinician can rapidly scan through an electrode combination space during programming. Also, during ordinary operation of the stimulator, similar technique can be applied to transition between electrode combinations associated with programs manually selected by the patient or automatically selected by the stimulator.

FIG. 1 is a schematic diagram illustrating an exemplary system 10 for programming neurostimulation therapy and for delivering neurostimulation therapy to a patient 12. System 10 includes an implantable neurostimulator 14 that delivers neurostimulation therapy to patient 12 and a programmer 11 for programming implantable neurostimulator 14. Neurostimulator 14 delivers neurostimulation therapy to patient 12 via leads 16A and 16B (collectively "leads 16"). Leads 16 may, as shown in FIG. 1, be implanted proximate to spinal cord 18 of patient 12 to deliver spinal cord stimulation (SCS) therapy to patient 12. Spinal cord stimulation may be used, for example, to reduce pain experienced by patient 12. Although an implantable neurostimulator 14 is described for purposes of illustration, various embodiments of this disclosure also may be applicable to external neurostimulators that reside outside the patient's body, and deliver stimulation therapy using one or more implanted leads deployed via a percutaneous port. Leads 16 may also be located at other nerve or tissue sites within patient 12. In addition, system 10 is not limited to spinal cord stimulation, and may be applicable to other electrical stimulation applications including pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, Parkinson's disease, epilepsy, urinary or fecal incontinence, sexual dysfunction, obesity, or gastroparesis.

Neurostimulator 14 delivers neurostimulation therapy to patient 12 according to one or more neurostimulation therapy programs. A neurostimulation therapy program may specify an electrode combination and values for a number of parameters associated with neurostimulation therapy delivered via the electrode combination. The parameters may include stimulation pulse voltage or current amplitudes, pulse widths, pulse rates, and other appropriate parameters such as duration or duty cycle. Leads 16 each include one or more electrodes (not shown in FIG. 1). The program further specifies an electrode combination in terms of electrodes that have been selected to deliver pulses according to the program and the polarities of the selected electrodes.

Two parameters for optimization of therapy are the electrode combination and the stimulation amplitude. The selection of electrodes determines which tissues are stimulated and, therefore, which physiological effects are perceived. Stimulation voltage or current amplitude determines the intensity and the extent of those effects. These electrode combination and stimulation amplitude settings are tightly coupled. A comfortable stimulation amplitude for one electrode combination might be uncomfortable or imperceptible for a second electrode combination.

Programmer 11 provides a programming interface that simulates the shifting of stimulation parameters smoothly from one electrode combination to a second electrode combination in a manner gradual enough to allow adjustments of amplitude should the sensation become uncomfortable or imperceptible to the patient during the shifting process. This gradual shifting is accomplished by the adjustment of stimulation voltage or current amplitudes of two or more electrode combinations having output pulses or pulse groups that are interleaved in time.

Neurostimulator 14 may deliver neurostimulation therapy to patient 12 according to a plurality of programs for a single symptom area, such as a number of leg pain programs. Neurostimulator 14 may have different program parameters for each of the leg pain programs based on a position of patient 12, an activity rate of patient 12, or other patient parameters. For example, neurostimulator 14 may deliver neurostimulation therapy to patient 12 during a first leg pain program using a first electrode combination when patient 12 is lying down and deliver neurostimulation therapy to patient 12 using a second leg pain program via a second electrode combination when patient 12 is standing. In some embodiments, patient 12 may use programmer 11 to input parameters to indicate posture changes, such as sitting, standing, or lying down. In other embodiments, neurostimulator 14 may include an orientation device to automatically determine the position of patient 12. The orientation device may be similar to an accelerometer or gyroscope.

In accordance with this disclosure, neurostimulator 14 is programmed to simulate a gradual shift between different electrode combinations, either for program transitions during clinician programming or during normal operation after programming has been completed. Neurostimulator 14 may shift between different program electrode combinations using incremental steps. For example, an amplitude of an initial electrode combination associated with the first program is incrementally decreased over a series of pulses or time slots, while an amplitude of the next electrode combination associated with the second program is incrementally increased over a series of alternating pulses or time slots. In alternative embodiments, e.g., as described later in this disclosure with respect to FIGS. 23-39, the first electrode combination may be maintained at a constant target amplitude until the second electrode combination reaches the target amplitude, at which time the amplitude of the first electrode combination may be incrementally decreased while the second electrode combination is maintained at the constant target amplitude. The first and second programs deliver one or more stimulation pulses in assigned time slots, such that stimulation energy is delivered by the electrode combinations on a time-interleaved basis.

An embodiment in which the amplitudes of stimulation energy delivered via the first and second electrode combinations are ramped downward and upward, respectively, will be described first. Specifically, the amplitudes of the first and second electrode combinations are ramped downward and upward, respectively, in incremental steps until the amplitude of the second electrode combination reaches a target amplitude. The incremental steps can be of fixed size or may vary according to an exponential, logarithmic or algorithmic change in accordance with the particular stimulation program. The incremental steps may also vary by a linear function, power law, or other function. The incremental steps may be taken automatically or under user control. In addition, the beginning amplitude of any electrode combination may be a non-zero amplitude. When the second electrode combination reaches its target amplitude, the first electrode combination associated with the first neurostimulation therapy program is shut off. These incremental adjustment techniques support perception of a smooth shift between programs. The techniques of the invention may further be used to shift between electrode combinations associated with program sets. A program set refers to a plurality of programs for treating different symptom areas that are provided to the patient virtually simultaneously using time-division multiplexing.

A programmer user, such as the clinician or patient 12, may use programmer 11 to program neurostimulation therapy for patient 12. In particular, the user may use programmer 11 to create neurostimulation therapy programs and update the neurostimulation therapy programs delivered by neurostimulator 14. As part of the program creation process, programmer 11 allows the user to evaluate electrode combinations that enable neurostimulator 14 to deliver neurostimulation therapy that is desirable in terms of, for example, symptom relief, coverage area relative to symptom area, and lack of side effects. Programmer 11 may also allow the user to evaluate electrode combinations that enable neurostimulator 14 to deliver effective neurostimulation therapy with desirable device performance characteristics, e.g., low battery consumption.

Programmer 11 controls neurostimulator 14, e.g., by instructions delivered via wireless telemetry, to test electrode combinations in order to allow a user to identify desirable combinations. Programmer 11 controls neurostimulator 14 to test a number of electrode combinations and allows the user to select particular electrode combinations that provide efficacious results. Programmer 11 may, for example, test a predefined sequence of electrode combinations, automatically identify the sequence of electrode combinations to test as the testing process progresses, or test electrode combinations in respond user input. In each case, neurostimulator 14 gradually shifts between different electrode combinations, as described herein.

As will be described in greater detail below, programmer 11 gradually shifts stimulation from a first electrode combination to a second electrode combination by incrementally adjusting stimulation amplitudes of the two electrode combinations and interleaving one or more output pulses in time. Although the electrode combinations do not deliver stimulation energy at the same time, the rate at which pulses or pulse groups in the time slots are interleaved serves to simulate a smooth shift of stimulation energy between electrode combinations. In other words, stimulation is delivered on a time-interleaved basis in time slots via respective electrode combinations at a sufficiently high frequency so that the patient perceives an overlap in the physiological effects of the interleaved time slots.

Programmer 11 initially programs neurostimulator 14 to gradually shift from a first electrode combination to a second electrode combination, then from the second electrode combination to a third electrode combination and so forth, through an nth electrode combination. The process may continue until an entire or partial set of electrode combinations is tested, or the physician or patient identifies a particularly efficacious electrode combination. In either case, the user may return to electrode combinations that were marked as particularly efficacious and optimize the parameter settings for those electrode combinations.

The shifting feature described herein may be embedded as a single function within a full featured programmer, which includes the option to program parameters incorporating traditional programming tools, as well as the diagnostic, measurement, and other features necessary to manage an implantable neurostimulator. Alternatively, the shifting feature could be deployed as a stand alone tool in a clinician programmer or patient programmer. Moreover, the shifting process may be executed by neurostimulator 14 in response to instructions from a clinician programmer during programming at a clinic, in response to instructions from a patient programmer during ordinary, chronic usage of the neurostimulator by a patient, or in response to instructions generated by a processor within the neurostimulator itself.

In some embodiments, the instructions generated by the clinician programmer or patient programmer may specify each shift increment in the transition from one electrode combination to another. In other cases, the instructions generated by clinician programmer or patient programmer may simply specify movement from one electrode combination to another electrode combination, or specify selection of a new program that requires such movement. In this latter case, neurostimulator 14 may execute the full shifting of amplitude from one electrode combination to another, as instructed by a clinician programmer or patient programmer, as a series of incremental shifting steps. As a further alternative, neurostimulator 14 may execute an electrode combination shift automatically, without receiving external instructions, e.g., in response to timing, patient activity or patient posture triggers that specify program changes in response to various sensed or tracked events.

During clinic evaluation of different electrode combinations for programming of neurostimulator 14, the shift process between subsequent electrode combinations proceeds under user control. In one embodiment, each incremental step in the shift may be contingent on input from the user. For example, programmer 11 may wait for the user to actuate an input device before performing the next incremental step in the shift. In another embodiment, programmer 11 may proceed through the incremental steps automatically unless it receives input from the user. For example, the user may control a dead man switch, and programmer 11 may cease the incremental steps upon deactivation of the dead man switch.

The user may control the sequence of electrode combinations using a time-domain metaphor, such as that found within compact disc players, or audio or video tape players. For example, in some embodiments, programmer 11 may provide input controls similar to play, stop, pause, rewind, and fast forward. These controls may permit the user to shift forward and backward between electrode combinations, as well as between incremental amplitude adjustments during shifting from one electrode combination to another.

Such controls may be in addition to amplitude, pulse width and rate adjustment controls, and may be operated by a physician or patient 12. Alternatively, the user may be able to control the sequence of electrode combinations using a directional input mechanism, such as a joystick, and a mapping program that maps the joystick movement to a particular electrode combination. In either case, programmer 11 shifts between each of the electrode combinations using shifting techniques described herein.

Additionally, programmer 11 may provide the user with the ability to control the overall intensity of the stimulations. Programmer 11 may, for example, include an input mechanism that allows the user to increase or decrease the intensity of the stimulations at any point during the shifting process to maintain comfortable sensations. In response to receiving input to increase or decrease the intensity of the stimulation, programmer 11 may adjust the intensity of one or both of the currently active programs as well as the target amplitude towards which the stimulation amplitude is progressing.

Programmer 11 may perform the same process to develop programs for other symptom areas. After developing a neurostimulation therapy program for all of the symptom areas of patient 12, programmer 11 assembles the individual programs into a program set and communicates the program set to neurostimulator 14. The program set may be delivered on a time-interleaved basis. For example, each program in the program set may be applied at a particular time, followed by each other program in succession, such that different stimulation parameters, and potentially different electrode combinations, are activated at different times, on a time-interleaved basis.

In order to control neurostimulator 14 to test electrode combinations, programmer 11 may communicate with neurostimulator 14 via wireless telemetry techniques known in the art. For example, programmer 11 may communicate with neurostimulator 14 via an RF telemetry head (not shown) or by local area telemetry. Information identifying desirable combinations of electrodes identified by the clinician may be stored as part of the neurostimulation therapy programs. Neurostimulation therapy programs created by the clinician using programmer 11 may be transmitted to neurostimulator 14 via telemetry, and/or may be transmitted to another programmer (not shown), e.g., a patient programmer, that is used by patient 12 to control the delivery of neurostimulation therapy by neurostimulator 14 during daily use.

Programmer 11 may include different programming modes. In one programming mode, programmer 11 supports testing of different electrode combinations and stimulation parameters. In this test mode, programmer 11 may receive user input and transmit programming signals to neurostimulator 14 to repeatedly change the electrode combinations, stimulation parameters, or both, based on the user input. The test mode makes use of the shifting techniques described herein. In another programming mode, programmer 11 transmits one or more program groups to neurostimulator 14 for operation. The program groups specify electrode combinations and stimulation parameters selected based on the results obtained during the test mode. Neurostimulator 14 stores the program groups within internal memory.

The invention is not limited to the combination of leads 16 shown in FIG. 1. For example, system 10 may include only a single lead or more than two leads implanted proximate spinal cord 18. Furthermore, the invention is not limited to the delivery of SCS therapy. For example, one or more leads 16 may extend from neurostimulator 14 to the brain (not shown) of patient 12, and neurostimulator 14 may deliver deep brain stimulation (DBS) therapy to patient 12 to treat tremor or epilepsy. As further examples, one or more leads 16 may be implanted proximate to the pelvic nerves (not shown) or stomach (not shown), and neurostimulator 14 may deliver neurostimulation therapy to treat incontinence or gastroparesis.

In some embodiments, electrode combination testing may be a continuing process throughout stimulation therapy. As patient 12 becomes accustomed to the therapy, the current stimulation programs may become less effective while other stimulation programs previously deemed ineffective may offer more effective therapy. To overcome these physiological changes, patient 12 may repeat electrode combination testing when the current therapy no longer provides relief. Alternatively, neurostimulator 14 may prompt patient 12 to repeat electrode combination testing upon unusual stimulation activity or a programmed schedule.

While programmer 20 of FIG. 1 and other programmers described herein are described as individual units, a programmer may instead be shown on a touch screen, or other display, of a larger computer. In other words, programmer 20, or other programmers, may be virtual programmers that allow a user to interact with them through the touch screen or other pointing device. Operation of a virtual programmer may be substantially similar to an individual, or standalone, programmer.

Figure 2:
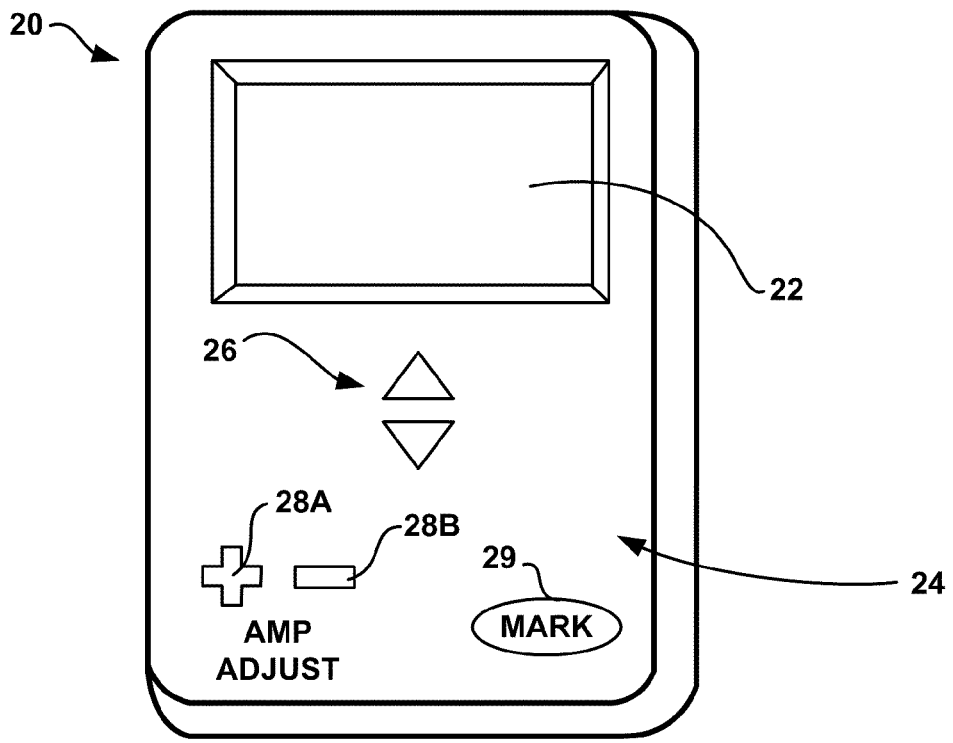
FIG. 2 is a schematic diagram illustrating an exemplary programmer for controlling an implantable neurostimulator to test electrode combinations for generating neurostimulation therapy programs.

FIG. 2 is a schematic diagram illustrating an exemplary programmer 20 for controlling neurostimulator 14 to test electrode combinations for generating neurostimulation therapy programs. Programmer 20 includes a display 22 to display information to a program user (not shown in FIG. 2). Display 22 may, for example, comprise an LCD or LED display. Programmer 20 also includes a keypad 24, which may be used by the user to interact with programmer 20.

Keypad 24 includes shift control buttons 26, amplitude adjustment buttons 28A and 28B ("amplitude adjustment buttons 28"), and a mark button 29. The user interacts with programmer 20 via keypad 24 to test electrode combinations in accordance with the techniques of the invention. In addition to shift control buttons 26, amplitude adjustment buttons 28, and a mark button 29, keypad 24 may include an alphanumeric keypad or additional keys associated with particular functions.

Although programmer 20 of FIG. 2 includes a keypad 24, a keypad is not required. In some embodiments, for example, display 22 may be a touch screen display, and the user may interact with programmer 20 via the touch screen display 22. The user may also interact with programmer 20 using peripheral pointing devices, such as a stylus, scroll wheel, mouse, or any combination of such devices, as well as hard keys or soft keys.

Programmer 20 controls neurostimulator 14 to test a number of electrode combinations, and allows the user to identify particular electrode combinations that provide efficacious results. Programmer 20 may, for example, control neurostimulator 14 to test a pre-defined sequence of electrode combinations or include a program for automatically identifying the sequence of electrode combinations to test. Programmer 20 controls neurostimulator 14 to shift between each of the electrode combinations by shifting stimulation energy from a first electrode combination to a second electrode combination in incremental steps on a time-interleaved basis. Specifically, programmer 20 gradually increases the amplitude of stimulation of the second electrode combination over a series of pulses or time slots while concurrently decreasing the amplitude of stimulation of the first electrode combination over a series of alternating pulses or time slots.

As described briefly above, the shifting process may be responsive to input from the user. For example, programmer 20 may require that the user actuate one of shift control buttons 26 between incremental steps (up/down) in the shift. If the user does not actuate one of shift control buttons 26, programmer 20 does not further adjust the amplitudes of the pulses. This feature helps to ensure that patient 12 remains comfortable during the incremental shifting process. If an incremental shift does result in discomfort to patient 12, a further incremental step would likely increase that discomfort. Therefore, requiring the user to actuate shift control buttons 26 reduces the likelihood of an incremental step being performed to the further discomfort of patient 12.

The amplitudes of the first and second electrode combinations are ramped downward and upward, respectively, until the amplitude of the second electrode combination reaches a target amplitude. The target amplitude may, for example, be a strong but comfortable (SBC) level measured during a calibration stage. An SBC level is a stimulation level at which patient 12 notices a therapeutic stimulation effect without the therapy inducing pain or discomfort. The first electrode combination is shut off upon the second electrode combination reaching the target amplitude, and a subsequent (e.g., third) electrode combination is turned on.

The subsequent electrode combination is the next electrode combination of the pre-defined or calculated electrode combination sequence. The subsequent electrode combination of the sequence may be an adjacent electrode combination. Adjacent electrode combinations include electrode combinations generated by shifting an electrode combination pattern upward or downward on a lead or by shifting left or right across columns in an array of leads or electrodes. For example, in a single lead numbered 0-7, the bipoles at 0-1 and 2-3 would be adjacent to the bipole at 1-2. For an array of electrodes or the parallel implant of linear leads, the bipole at 1-2 in a first column (or first linear lead) would be considered adjacent to the bipole in the second column at level 1-2.

The subsequent electrode combinations of the sequence, however, need not be adjacent electrode combinations. Although shifting between adjacent electrodes is the most likely use of this shifting feature, this feature could also be used to shift stimulation gradually between non-adjacent or unrelated combinations. This may be desirable in the case where the 'adjacency' in sensation does not directly correlate with adjacency on the lead, which may be due to nerve branching or other anatomical structure. Nonadjacent shifting may simply prove more pleasing to the patient than the traditional method of stopping one group of settings prior to beginning stimulation on a second group.

When the shifting process is finished, a subset of marked points, i.e., electrode combinations and parameters, may be further refined using optimization tools similar to those described in U.S. Published Patent Application No. 2004/0215288, entitled "Identifying combinations of electrodes for neurostimulation therapy," to Lee et al., the entire content of which is incorporated herein by reference. For example, a number of neighboring electrode combinations may be selected and evaluated.

Programmer 20 shifts from the second electrode combination to the third in the same manner described above. Programmer 20 continues to shift between subsequent electrode combinations until all of the electrode combinations of the sequence have been tested. The "up" shift control button 26 serves to shift the process forward from a first electrode combination to a second electrode combination in an incremental step.

For example, upon one actuation of the "up" shift control button 26, the stimulation amplitude on the first electrode combination decreases by one step, while the stimulation amplitude on the second electrode combination increases by one step. In this case, the shift sequence moves forward. Likewise, the "down" shift control button 26 serves to shift the process backward from the second electrode combination to the first electrode combination. Upon one actuation of the "down" shift control button 26, the stimulation amplitude on the first electrode combination increases by one step, while the stimulation amplitude on the second electrode combination decreases by one step. In this case, the shift sequence moves backward.

In the example of FIG. 2, the user interacts with programmer 20 via mark button 29 to indicate points at which the parameters of stimulation yield efficacious results. The user may actuate mark button 29 at any time throughout the electrode testing sequence. Furthermore, the user may actuate mark button 29 numerous times throughout the electrode testing sequence. Programmer 20 stores the current parameter values of the stimulations upon actuation of mark button 29. For example, the programmer 20 may store the amplitude values for each of the electrode combinations, the current target amplitude, i.e., the SBC level, and other parameter values necessary to generate a program in memory. After programmer 20 completes the electrode testing sequence, the user may return to the marked settings to optimize the parameters. The user may, for example, switch between two or more marked settings for the purpose of comparison.

The user may also interact with programmer 20 via amplitude adjustment buttons 28 to control the overall intensity of the stimulation. The user may adjust the overall intensity of the stimulations at any point during the electrode testing sequence using amplitude adjustment buttons 28. The user may, for example, actuate the "−" amplitude adjustment button 28B to decrease the overall intensity of stimulations when the stimulations become uncomfortable. Likewise, the user may actuate the "+" amplitude adjustment button 28A to increase the overall intensity of the stimulations when patient 12 can no longer perceive the stimulation or desires more therapy. In response to actuation of one of amplitude adjustment buttons 28, programmer 20 adjusts the amplitudes of one or both of the electrode combinations as well as the target amplitude towards which it is working. Programmer 20 also may include inputs for pulse width and pulse rate adjustments.

Figure 3:
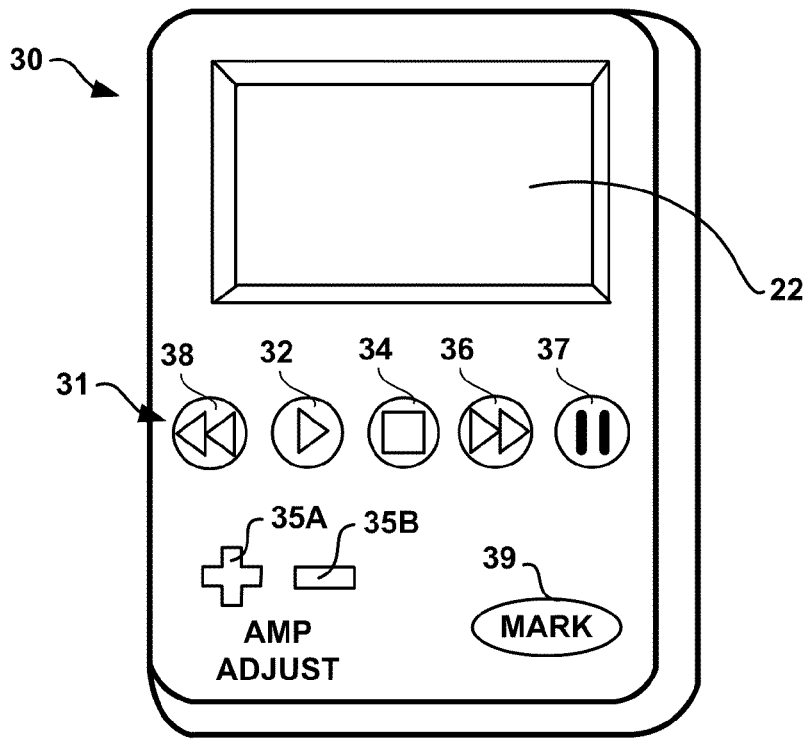
FIG. 3 is a schematic diagram illustrating an exemplary programmer to search stimulation programs for controlling an implantable neurostimulator to test electrode combinations.

FIG. 3 is a schematic diagram illustrating another exemplary programmer 30 for controlling neurostimulator 14 to test electrode combinations for generating neurostimulation therapy programs. Programmer 30 conforms substantially to programmer 20 illustrated in FIG. 2, but programmer 20 incorporates a different set of shift control buttons. Shift control buttons 31 include a play button 32, stop button 34, fast forward button 36, rewind button 38, and pause button 37. Also included are amplitude adjustment buttons 35A and 35B and mark button 39. With programmer 30, the user input may be obtained using a time-domain metaphor, such as that found within compact disc players, or audio or video tape players. Other input devices with similar forward/rewind functionality, such as a scroll wheel, may also be used. An example of a scroll wheel is the touch scroll wheel implemented by the iPod devices manufactured by Apple Computer.

The user interacts with programmer 30 in a slightly different fashion to control the shift. Unlike programmer 20, programmer 30 does not require the user to provide input between each incremental step of the shift. Instead, the user initiates the electrode combination testing sequence by pressing play button 32. Programmer 30 incrementally adjusts the stimulation amplitude of subsequent electrode combinations in a predefined sequence until the user presses stop button 34.

In this manner, programmer 30 proceeds through the incremental steps automatically unless it receives input from the user. The user may also use fast forward button 36 to move more quickly through the sequence and rewind button 38 to return to a previous location in the sequence. In this way, the user may return to an electrode combination and parameter setting quickly and repeatedly, if desired. This feature may be especially useful for the patient in rewinding, or revisiting, the sequence to reevaluate a point in the sequence observed to provide efficacy.

Programmer 30 is not limited to the shift control buttons depicted in FIG. 3. For example, programmer 30 may include other types of shift control buttons such as a scroll wheel to allow the user to move through the electrode combination testing more quickly. Like programmer 20 of FIG. 2, the user may interact with the programmer to indicate points at which the parameters of stimulation yield efficacious results using mark button 39 and to control parameters such as amplitude, pulse width and pulse rate using buttons 35, respectively.

Figure 4:
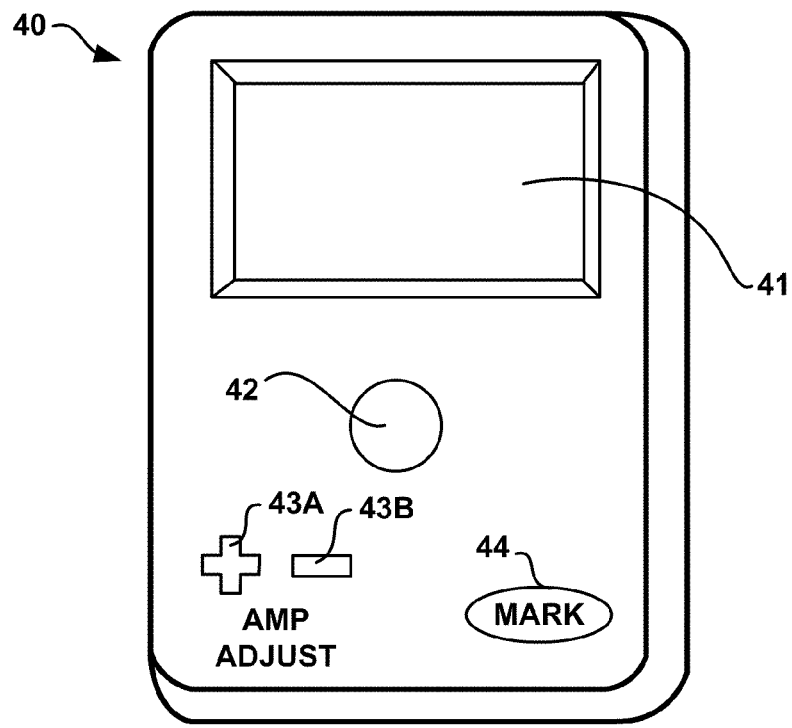
FIG. 4 is a schematic diagram illustrating an exemplary programmer with a dead-man switch for controlling an implantable neurostimulator to test electrode combinations.

FIG. 4 is a schematic diagram illustrating another exemplary programmer 40 for controlling neurostimulator 14 to test electrode combinations for generating neurostimulation therapy programs. Programmer 40 conforms substantially to programmer 30 illustrated in FIG. 3, but incorporates deadman switch 42 instead of a play button 32, stop button 34, fast forward button 36 and rewind button 38. Programmer 30 incrementally shifts the stimulation energy between successive electrode combinations in the sequence while dead-man switch 42 is actuated. Upon release of dead-man switch 42, programmer 40 no longer adjusts the amplitudes of the electrode combinations. In this manner, the user can start and stop the shift sequence. Programmer 40 also includes screen 41, amplitude buttons 43A and 43B, and mark button 44, similar to programmers 20 and 30.

Figure 5:
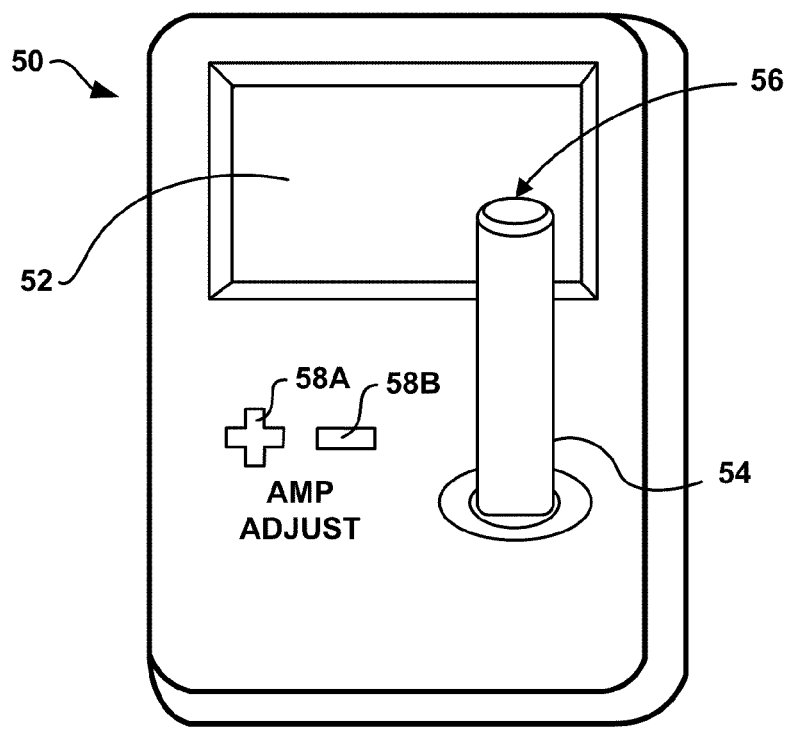
FIG. 5 is a schematic diagram illustrating an exemplary programmer with a directional device for controlling an implantable neurostimulator to test electrode combinations.

FIG. 5 is a schematic diagram illustrating an exemplary programmer 50 for controlling neurostimulator 14 to test electrode combinations for generating neurostimulation therapy programs. Programmer 50 includes a display 52 to display information to a program user (not shown in FIG. 5). Display 52 may, for example, comprise an LCD or LED display. In some embodiments, a touch screen display may be provided. As shown in FIG. 5, a directional controller 54, a mark button 56 and amplitude adjustment buttons 58A and 58B ("amplitude adjustment buttons 58") are disposed within and/or on programmer 50.

In the illustrated embodiment, directional controller 54 is a joystick, and mark button 56 is disposed on an end of directional controller 54. Mark button 56 may be located at any place on directional controller 54 or programmer 50. In other embodiments, any or all of directional controller 54, mark button 56, and amplitude adjustment buttons 56 may be software screen objects on a display. For example, in some embodiments, directional controller 54 may take the form of a representation of, e.g., a joystick, or up-down and side-to-side arrows, on a touch-screen display that is capable of being manipulated by a user.

Programmer 50 generates an output as a function of the direction of manipulation of directional controller 54. In particular, programmer 50 uses a map to select combinations of electrodes located on leads 16 as a function of the direction of manipulation of directional controller 54. Directional controller 54 thus allows a user to provide input to select electrode combinations. In this manner, the user may manipulate directional controller 54 to search for an electrode combination that provides effective stimulation to patient 12.

When the user manipulates directional controller 54 beyond a certain location to select a new electrode combination, programmer 50 shifts between the electrode combinations in accordance with the shift techniques described herein. The amplitudes of the pulses on the first and second electrode combinations are incrementally ramped downward and upward, respectively, on a time-interleaved basis over a series of time slots, until the amplitude of the second electrode combination reaches a target amplitude. The incremental steps in the shift may be contingent on input from the user or may proceed automatically. For example, the incremental steps may proceed as a function of the rate or amount of directional movement indicated by directional controller 54.

Like programmer 20 of FIG. 2, the user may interact with programmer 50 to indicate points at which the parameters of stimulation yield efficacious results using mark button 56. In the example of FIG. 5, mark button 56 may be mounted on a joystick, e.g., for thumb actuation. Additionally, the user may interact with programmer 50 to control the overall intensity of the stimulations using adjustment buttons 58, e.g., for amplitude, pulse width and pulse rate.

In some embodiments, directional controller 54 may provide force feedback to the user. For example, certain electrode combinations may cause discomfort or pain to patient 12. These locations may be pre-programmed or marked once discovered during testing. These locations may be blocked through the use of feedback in controller 54. In this case, controller 54 may be physically prevented from moving to defined locations of programmer 50. Alternatively, electrode combinations associated with specific control 54 locations may not be turned on when controller 54 is moved to these locations.

Figure 6:
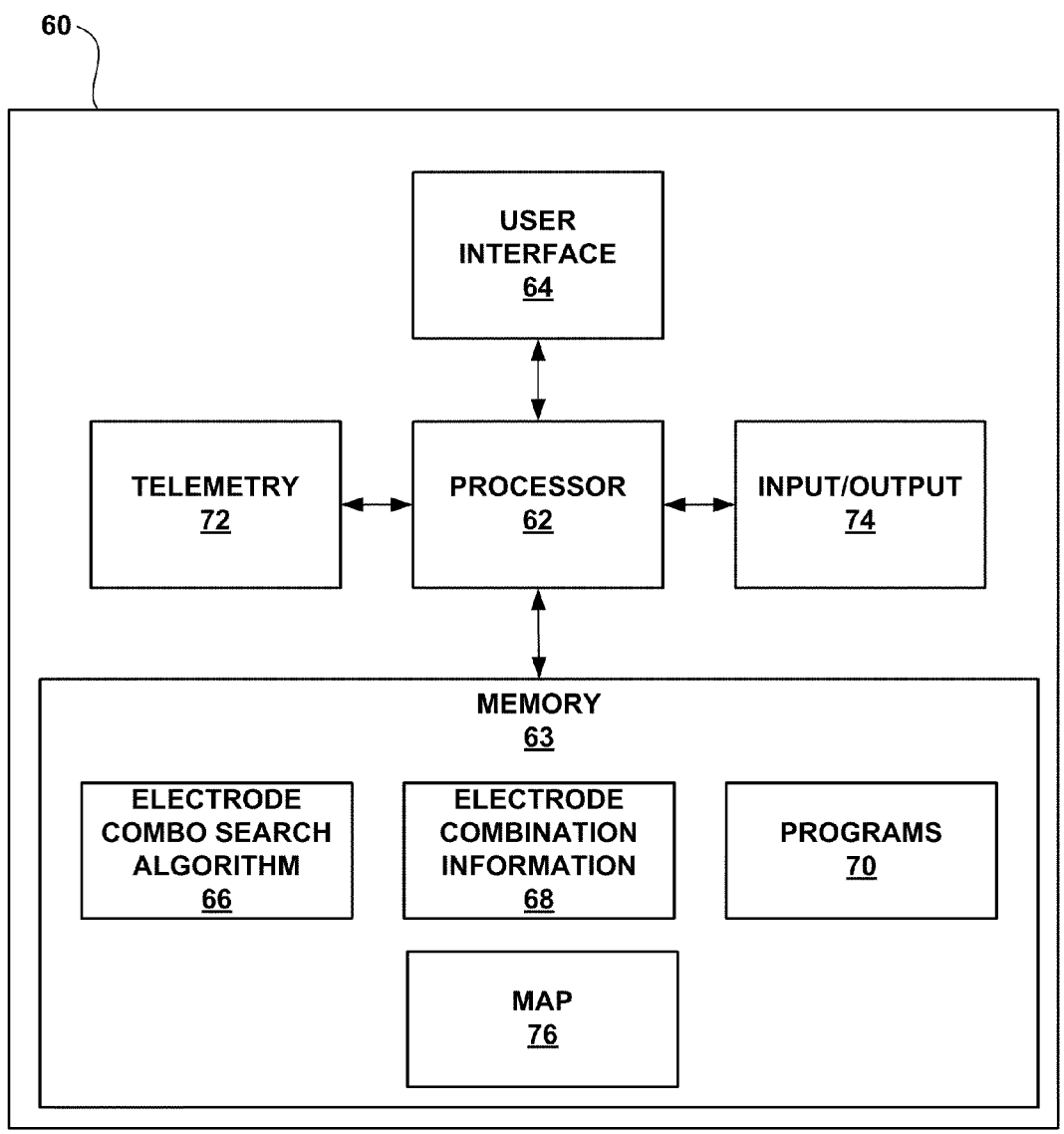
FIG. 6 is a block diagram illustrating exemplary components of a programmer.

FIG. 6 is a block diagram illustrating an example configuration of a programmer 60, such as any of programmers 11, 20, 30, 40 and 50 of FIGS. 1-5. A user may interact with a processor 62 via a user interface 64 in order to identify efficacious electrode combinations as described herein. User interface 64 may include a display and one or more input mechanisms. Using programmer 20 of FIG. 2 as an example, user interface 64 may include display 22, arrow buttons 26, amplitude adjustment buttons 28, and a mark button 29. Processor 62 may also provide a graphical user interface (GUI) via user interface 64 to facilitate interaction with the user. Processor 62 may include a microprocessor, a microcontroller, a DSP, an ASIC, an FPGA, or other equivalent discrete or integrated logic circuitry.

Programmer 60 also includes a memory 63. Memory 63 may include program instructions that, when executed by processor 62, cause programmer 60 to perform various functions ascribed to programmer 60 herein. As described in detail above, processor 62 runs a user-controlled test of a sequence of electrode combinations to identify effective electrode combinations for alleviating symptom areas. Memory 63 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 62 may receive a pre-defined set of electrode combinations to test from a clinician and store the pre-defined set of electrode combinations in electrode combination information 68. Alternatively, processor 62 may execute an electrode combination search algorithm 66 stored within memory 63 to select individual electrodes or electrode combinations to test. Processor 62 shifts between subsequent electrode combinations in accordance with the shifting techniques described herein.

In embodiments in which programmer 60 includes a directional controller for receiving input to select electrode combinations, programmer 60 may further include a map 76 to select combinations of electrodes located on leads 16 as a function of the location or direction of movement indicated by manipulation of directional controller 54. Map 76 may map, for example, X-Y coordinates of controller 54 to particular combinations of electrodes on leads 16. In this manner, the user may manipulate directional controller 54 to search for an electrode combination that provides effective stimulation to patient 34. Alternatively, controller 54 may indicate a progression between successive electrode combinations in an array without regard to position, and without the need to map X-Y coordinates to particular electrode combinations.

Processor 62 may collect information relating to tested electrode combinations, and store the information in memory 63 for later retrieval and review by the user to facilitate identification of desirable electrode combinations. Neurostimulation therapy programs 70 created by the user may be stored in memory 63, and information identifying electrode combinations selected by the user to be utilized for one of programs 70 may be stored as part of the program within memory 63. Memory 63 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 62 controls neurostimulator 14 to test selected electrode combinations by controlling neurostimulator 14 to deliver neurostimulation therapy to patient 12 via the selected electrode combinations. In particular, processor 62 transmits programming signals to neurostimulator 14 via a telemetry circuit 72. As a sequence of electrode combinations proceeds, the programming signals may be transmitted at a rate consistent with the control input provided by a user. In this manner, the user may quickly observe the effects of each increment in the shift between electrode combinations.

Additionally, after completion of electrode testing, processor 62 may transmit one or more of neurostimulation therapy programs 70 created by the clinician to neurostimulator 14 via telemetry circuit 72, or to another programmer used by the patient to control delivery of neurostimulation therapy via input/output circuitry 74. I/O circuitry 74 may include transceivers for wireless communication, appropriate ports for wired communication or communication via removable electrical media, or appropriate drives for communication via removable magnetic or optical media. In other embodiments, processor 62 may transmit one or more of neurostimulation therapy programs 70 created by the clinician to neurostimulator 14 during the electrode testing process.

Figure 7:
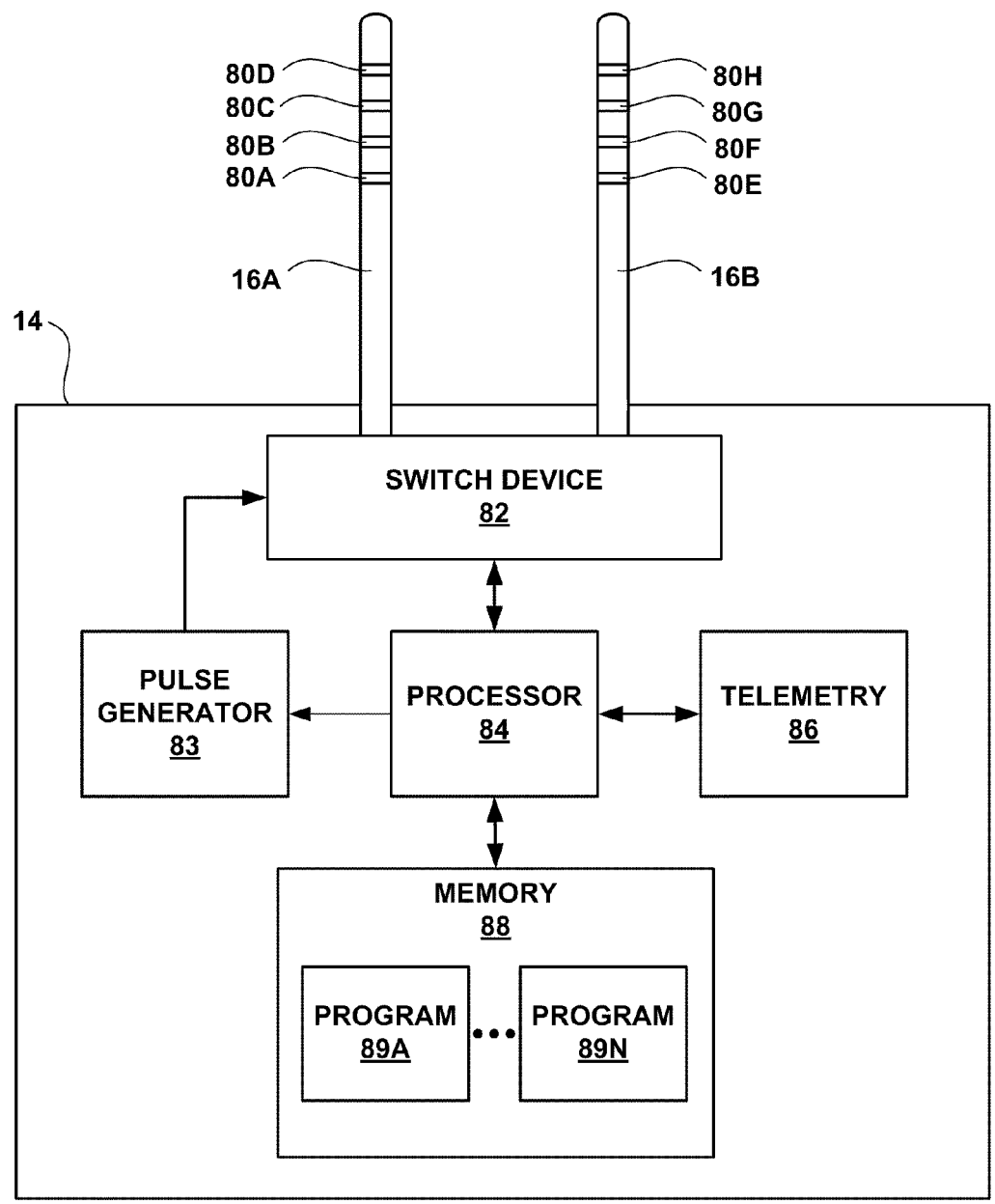
FIG. 7 is a block diagram illustrating exemplary components of an implantable neurostimulator.

FIG. 7 is a block diagram illustrating an example configuration of neurostimulator 14. Neurostimulator 14 may deliver neurostimulation therapy via electrodes 80A-D of lead 16A (FIG. 1) and electrodes 80E-H of lead 16B (collectively "electrodes 80"). Electrodes 80 may be, for example, ring electrodes. In the example illustrated in FIG. 7, each of leads 16 includes four electrodes 80 which are implanted such that they are substantially parallel to each other and spinal cord 18 (FIG. 1), on substantially opposite sides of spinal cord 18, at approximately the same height relative to spinal cord 18, and oriented such that the distal ends of leads 16 are higher relative to the spinal cord than the proximal ends of leads 16. Such a configuration is commonly used to provide SCS therapy. The configuration, type, and number of electrodes 80 illustrated in FIG. 7 are merely exemplary. For example, neurostimulator 14 may include any number of leads that each has any number of electrodes.

Neurostimulator 14 includes pulse generator 83, processor 84, telemetry circuit 86, memory 88, and neurostimulation therapy programs 89A-89N ("programs 89") stored in memory 88. Electrodes 80 are electrically coupled to a switch device 82 via leads 16. Switch device 82 may be a switch array, switch matrix, multiplexer, or any other type of switching device suitable to selectively couple stimulation energy to selected electrodes. Processor 84 controls a pulse generator 83 to generate stimulation pulses, and controls switch device 82 to couple the stimulation energy to selected electrodes. Pulse generator 83 is coupled to electrodes 80 via switch device 82. Pulse generator 83 may be coupled to a power source, such as a rechargeable or non-rechargeable battery.

Processor 84 controls pulse generator 83 to deliver stimulation energy with parameters specified by one or more of programs 89, such as amplitude, pulse width, and pulse rate. In addition, processor 84 controls switch device 82 to select different electrode combinations for delivery of stimulation energy from pulse generator 83. Processor 84 may include a microprocessor, a controller, a digital signal processor (DSP), an application specific integrated circuit (ASIC), a field-programmable gate array (FPGA), or equivalent discrete or integrated logic circuitry.

Pulse generator 83 may be a single- or multi-channel pulse generator. In particular, pulse generator 83 may be capable of delivering a single stimulation pulse or multiple stimulation pulses at a given time via a single electrode combination or multiple stimulation pulses at a given time via multiple electrode combinations. In some embodiments, however, pulse generator 83 and switch device 82 may be configured to deliver multiple channels on a time-interleaved basis. In this case, switch device 82 serves to time division multiplex the output of pulse generator 83 across different electrode combinations at different times to deliver multiple programs or channels of stimulation energy to the patient.

For testing of electrode combinations, processor 84 controls neurostimulator 14 to smoothly shift stimulation energy between different electrode combinations. Neurostimulator 14 shifts between electrode combinations of different programs by incrementally adjusting the amplitudes of the electrode combinations to smoothly shift from one electrode combination to another. For example, processor 84 may be responsive to changes in programs 89, as received from a programmer, to control switch device 82 and pulse generator 83 to deliver stimulation pulses or groups of pulses to different electrode combinations in successive time slots.

In one time slot, for example, processor 84 controls pulse generator 83 to deliver one or more stimulation pulses with a given amplitude, and controls switch device 82 to deliver the pulses via a first electrode combination. In the next time slot, processor 84 controls pulse generator 83 to deliver one or more stimulation pulses with a different amplitude, and controls switch device 82 to deliver the pulses via a second electrode combination. Hence, successive time slots contain stimulation pulses that are delivered at different amplitudes and via different electrode combinations to simulate a smooth shift of stimulation energy between the electrode combinations.

Programmer 60, such as any of programmers 11, 20, 30, 40 and 50 of FIGS. 1-5, controls neurostimulator 14 to test electrode combinations so that a user may identify desirable combinations. Programmer 60 controls neurostimulator 14 to test a number of electrode combinations and allows the user to select particular electrode combinations that provide efficacious results. Telemetry circuit 86 allows processor 84 to communicate with programmer 60 during the electrode testing process. In particular, processor 84 receives, as updates to programs 89, values for stimulation parameters such as amplitude and electrode combination, from the programmer via telemetry circuit 86, and delivers one or more stimulation pulses according to the received stimulation parameters.

As described above, processor 84 receives stimulation parameters for at least two electrode combination interleaved as to provide patient 12 with the perception of continual stimulation. Processor 84 continues to receive stimulation patterns from programmer 60 and deliver stimulation pulses to patient 12 until the entire series of electrode combinations are tested or the user has interacted with the programmer to stop the testing. Processor 84 may also receive updated program information created by the user after completion of the electrode testing and update one or more of programs 89 such that therapy delivery circuit 82 delivers stimulation pulses according to the updated program.

In addition to program 89, memory 88 may include program instructions that, when executed by processor 84, cause neurostimulator 14 to perform various functions ascribed to the neurostimulator herein. Memory 88 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Figure 8:
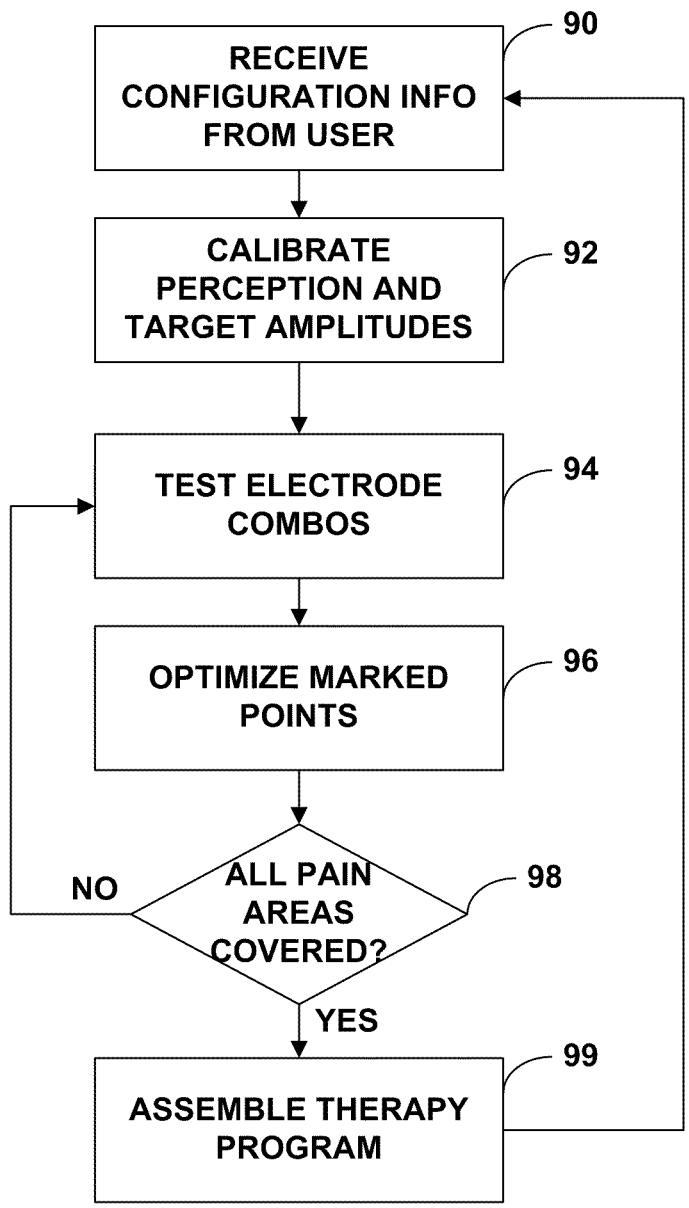
FIG. 8 is a flow diagram illustrating exemplary operation of a programmer programming an implantable neurostimulator.

FIG. 8 is a flow diagram illustrating exemplary operation of a programmer, such as programmer 11 of FIG. 1, programming neurostimulator 14 in accordance with the techniques of the invention. Programmer 11 receives configuration information from a user (90). The configuration information may relate to electrode settings and pulse settings. The electrode setting information received by programmer 11 may include the number of leads, a type of lead for each of the leads, a lead orientation, a lead positioning, a subset of electrodes over which the shifting feature should operate, a lead pattern to use, and a starting location (e.g., a first electrode combination). For example, the lead information may indicate that the lead is a 1×8 lead, the starting location is the top electrode, and the lead pattern is the best single cathode combination. The pulse setting information may include pulse width, rate and rise parameters.

Programmer 11 may then initiate a calibration sequence with the user to identify perception and target amplitudes (92). During the calibration sequence, programmer 11 increases the amplitude of the stimulation on an electrode combination and marks the amplitude level at which the user first perceives stimulation, i.e., the perception amplitude or perception amplitude as described herein, and the amplitude level at which the stimulation is strong but still comfortable (SBC), i.e., the target amplitude. Programmer 11 may calibrate perception and target amplitudes for any number of electrode combinations. Programmer 11 stores the perception and target amplitude values for later use during the shifting process.

Programmer 11 begins testing different electrode combinations in accordance with user input (94). To begin, the user may select the portions of the lead array over which the shifting feature should operate. For example, the selected portions may include a single lead, a subset of a single lead, across multiple leads, or a particular subset of electrodes in an array. The user also selects an electrode combination, i.e., electrode pattern, to shift about the selected portion of the lead. The combination could include, for example, a single bipole, a guarded cathode combination, a single cathode (in systems that support unipolar stimulation), or any other combination of one or more electrodes on a lead or multiple leads. Finally, the user selects a starting point, i.e., the location of the first electrode combination to be evaluated. The first electrode combination could be at the end of one lead or at a boundary of a selected subset of an array.

To begin the shifting process, programmer 11 programs neurostimulator 14 to apply stimulation pulses to patient 12 via the first electrode combination identified by the user, i.e., the starting location. Programmer 11 ramps the stimulation amplitude of the first electrode combination upward in incremental steps until it reaches the target amplitude identified during calibration. If no calibration sequence was performed, the programmer ramps up the stimulation amplitude of the first electrode combination in incremental steps until the user identifies a strong but still comfortable (SBC) level, which serves as the target amplitude level.

Programmer 11 begins to smoothly transition to a second electrode combination upon reaching the target amplitude of the first electrode combination. As discussed above, the incremental steps in the transition may be directly or indirectly controlled by a user. Programmer 11 shifts to the second electrode combination in a manner that simulates a smooth shift of stimulation energy for purposes of patient perception. Although the stimulation energy is not delivered continuously and simultaneously by the electrode combinations, the rate at which time slots containing pulses are interleaved causes the patient to perceive a smooth shift from the first electrode combination to the next. In particular, the patient perceives that the physiological effects of the pulses from the different electrode combinations are occurring on a substantially continuous or overlapping basis.

Programmer 11 turns on the second electrode combination at a low level of amplitude and incrementally increases the amplitude of pulses delivered via the second electrode combination while concurrently decreasing the amplitude of pulses delivered via the first electrode combination in alternating time slots. The first electrode combination exists in program 1 (P1), while the second electrode combination exists in program (P2). Each incremental step may be contingent on receiving input from the user. In other embodiments, programmer 11 automatically increments the amplitude of stimulation energy delivered via the electrode combination over time unless the user provides input indicating discomfort.

During the electrode combination testing, programmer 11 receives input from the user identifying particularly efficacious electrode combinations. After the electrode combination testing is complete, programmer 11 allows the user to return to the marked settings and optimize those settings (96). The user may, for example, be able to return to the marked settings and switch between them for purposes of comparison.

Programmer 11 determines whether the program covers all symptom areas experienced by patient 12 (98). If the electrode combination identified does not cover all symptom areas, programmer 11 runs the user through another electrode combination testing session to determine an efficacious electrode combination for the other symptom areas. Patient 12 may, for example, be experiencing leg pain as well as lower back pain. The electrode combination testing may be performed for each of the symptom areas to identify electrode combinations that are particularly affective for each area of pain. In some embodiments, programmer 11 may repeat testing the same electrode combinations. In other embodiments, programmer 11 may modify the electrode combinations based upon marked combinations of some other pre-defined algorithm.

When programmer 11 identifies electrode combinations for all of the symptom areas, the programmer assembles a program set that includes programs for each symptom area (99). As described above, the programs of the program set each contain a number of stimulation parameters, including the stimulation amplitudes and electrode combinations identified during the testing. Programmer 11 programs neurostimulator 14 with the created program set via a telemetry unit.

As discussed above, stimulation energy is shifted from one electrode combination to the next electrode combination using a series of incremental steps. In the first step, stimulation is occurring only on the first electrode combination using a single channel (program P1) of output from the implantable device. In the first incremental step of shifting, the system turns on the second combination at a low level of amplitude and using a second channel of stimulation (program P2). These different programs P1, P2 of stimulation are delivered with their pulses or groups interleaved in alternating time slots, using capabilities available in current neurostimulators, such that their physiological effects occur simultaneously and overlap in the perception of patient 12.

In a simple example, the amplitude at which the second program P2 of stimulation is introduced could be zero. In a more complex design, the second program P2 could be introduced at an amplitude equal to the lower threshold, or amplitude, at which the patient first perceives stimulation. This lower amplitude could be measured directly from a full calibration, interpolated from a partial calibration using only a subset of possible electrodes, or estimated as a percentage, e.g., 40%, of the current SBC level of stimulation.

In subsequent steps of the shifting process, the amplitude of the first electrode combination (associated with program P1) is decreased while the amplitude on the second electrode combination (associated with program P2) is increased. Step sizes, which may be linear and fixed or vary according to exponential, logarithmic or algorithmic change, may be dependent on characteristics of the lead locations and the electrode spacing within a lead. For example, larger spacing may make a slower rate of change more appropriate. The number of steps to complete a full shift may vary, although ten steps are provided for purposes of example.

The shift is complete when the amplitude of the second combination (P2) reaches the SBC amplitude at which the first combination began. At this point, the amplitude (P1) of the first combination has reached either zero or the lower amplitude, and can be shut off with no loss of patient sensation. At this point, the shifting process continues from the second combination (now using P2 with a strong-but-comfortable amplitude) to a third combination adjacent to the second, reusing the program P1, which becomes available when the first combination is turned off.

In some embodiments, at any point during the shifting process, the user can increase or decrease the intensity of stimulation to maintain comfortable sensations that are strong enough to evaluate the efficacy of the combinations. When an increase or decrease in intensity is initiated by the user, the programmer adjusts both of the currently active programs as well as the target, or SBC, amplitude.

The shifting of stimulation energy between successive electrode combinations may step between adjacent electrode combinations or non-adjacent electrode combinations. In addition, the shift process may step between similar electrode patterns or different electrode patterns. For example, the first and second electrode combinations may share a common pattern of electrodes, but represent a shifting upward or downward on a lead set.

As an illustration, for a 2×8 electrode arrangement in which two leads each carry eight electrodes, and the electrodes on one lead are designated 0 through 7 from top to bottom, and the electrodes on the other lead are designated 8-15 from top to bottom, a first combination could be the following: 0+ 1− 2+, where the number designates the electrode position and the plus or minus designates the polarity of the electrode.

In this example, a shift to a second electrode combination could yield the same pattern but simply move down one electrode position, e.g., 1+ 2− 3+. In other embodiments, the first and second electrode combinations may have different patterns, e.g., combination 1=0+ 1− and combination 2=0+ 1− 2+, and then combination 3=1+ 2−.

Figure 9:
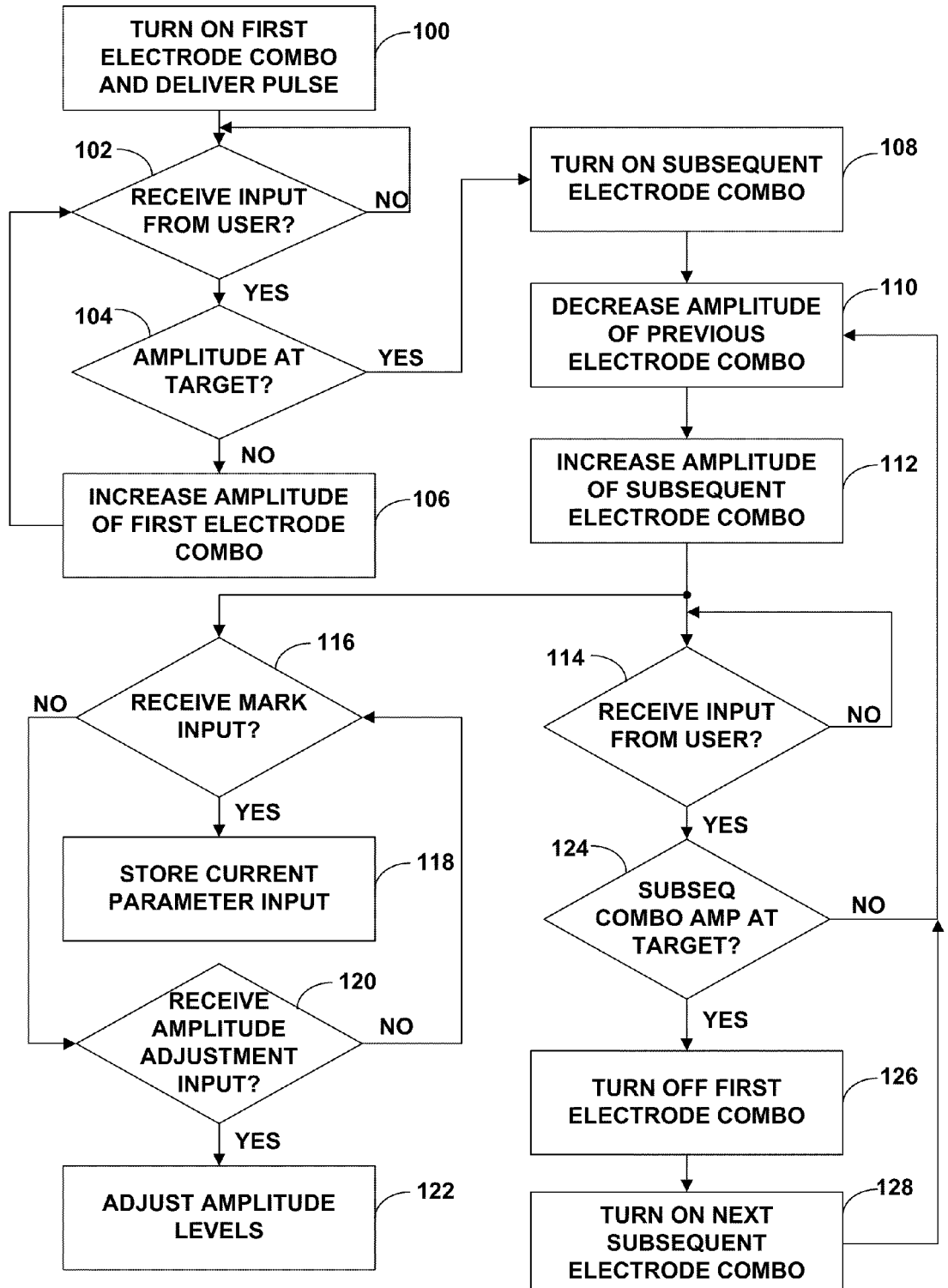
FIG. 9 is a flow diagram illustrating exemplary operation of a programmer testing electrode combinations.

FIG. 9 is a flow diagram illustrating exemplary operation of a programmer, such as programmer 11 of FIG. 1, in testing electrode combinations. Electrode combination testing is performed under user control, with each incremental step contingent on receiving input from the user. Initially, programmer 11 controls neurostimulator 14 to select a first electrode combination and delivers a pulse or group of pulses in a time slot via the first electrode combination (100). The user may specify which electrode combination programmer 11 should test during initial configuration.

Programmer 11 next determines whether it has received input from the user (102) for an increase in amplitude of the stimulation energy delivered via the first electrode combination. The user may, for example, be a physician, and the physician may actuate a button when a patient indicates that the pulse amplitude is comfortable. In another embodiment, patient 12 may be the user, thereby eliminating the need for communication between the physician and patient 12. In the example of FIG. 9, programmer 11 does not increment the stimulation amplitude any further until input is received from the user.

Upon receiving input from the user to indicate that the stimulation amplitudes are comfortable, programmer 11 determines whether the stimulation amplitude of the first electrode combination has reached the target amplitude (104). When the stimulation amplitude of the first electrode combination is below the target amplitude, programmer 11 increases the amplitude of the stimulation of the first electrode combination by a step (106), and waits for user input (102).

When the stimulation amplitude of the first electrode combination reaches the target amplitude, programmer 11 turns on a subsequent electrode combination (108). As described above, the subsequent electrode combination may be the next electrode combination in a pre-defined sequence of electrode combinations. Alternatively, the next electrode combination may be selected in response to input from the user, such as time-domain or sequence-domain input identifying a time or position within a sequence, or planar input identifying a direction or location.

Programmer 11 decreases the amplitude of the first electrode combination (110) and increases the amplitude of the subsequent electrode combination by a single step (112). The step may be a fixed linear step or an exponential or other algorithmic change such as a logarithm. For example, the first step may be 10% of the target amplitude. As described above, programmer 11 interleaves time slots containing one or more stimulation pulses provided to the first electrode combination and the subsequent electrode combination. The time slots are interleaved at a frequency that provides the patient with the feeling of a smooth shift between the electrode combinations.

Programmer 11 waits to receive user input indicating that the stimulation amplitude remains comfortable after the step (114). Programmer 11 concurrently monitors for mark input from the user (116). Mark input may be received when a user determines that a particular setting is efficacious. Upon receiving mark input, programmer 11 stores current parameter values (118). For example, programmer 11 may store the amplitude values for each of the electrode combinations, i.e., the first electrode combination and the subsequent electrode combination. Additionally, programmer 11 may store the current target amplitude. Programmer 11 may return to the marked settings at a later time to allow the user to optimize the parameters.

Programmer 11 also monitors for amplitude adjustment input from the user (120). Amplitude adjustment information may be received at any time during the shifting process. The user can increase or decrease the overall intensity of stimulation to maintain comfortable sensations that are strong enough to evaluate the efficacy of the combinations. Programmer 11 adjusts the overall intensity of the stimulation in response to receiving input from the user (122). For example, programmer 11 may adjust one or both of the stimulation amplitudes applied to the first and subsequent electrode combinations as well as the target amplitude toward which programmer 11 is working.

Programmer 11 determines whether the amplitude of the subsequent electrode combination is at the target amplitude (124). If the amplitude of the subsequent electrode combination has not reached the target amplitude, programmer 11 adjusts the amplitudes of the previous electrode combination and the subsequent electrode combination. Specifically, programmer 11 decreases the amplitude of the previous electrode combination one more step and increases the amplitude of the subsequent electrode combination one more step. In some embodiments, the step size may be different between decreasing amplitude or increasing amplitude. In other words, amplitude may be ramped upwards faster or slower than amplitude ramped downwards.

If the amplitude of the subsequent electrode combination has reached the target amplitude, programmer 11 turns off the first electrode combination (126) and turns on the next subsequent electrode combination in the sequence (128). Programmer 11 begins to incrementally shift the two electrode combinations in the same manner to smoothly transition between them. Programmer 11 tests all the electrode combinations of the sequence, transitioning between each one in accordance with the invention. Again, the sequence may be a predefined sequence of adjacent or nonadjacent electrode combinations, or a sequence that is dynamically generated in response to input from the user.

Figure 10:
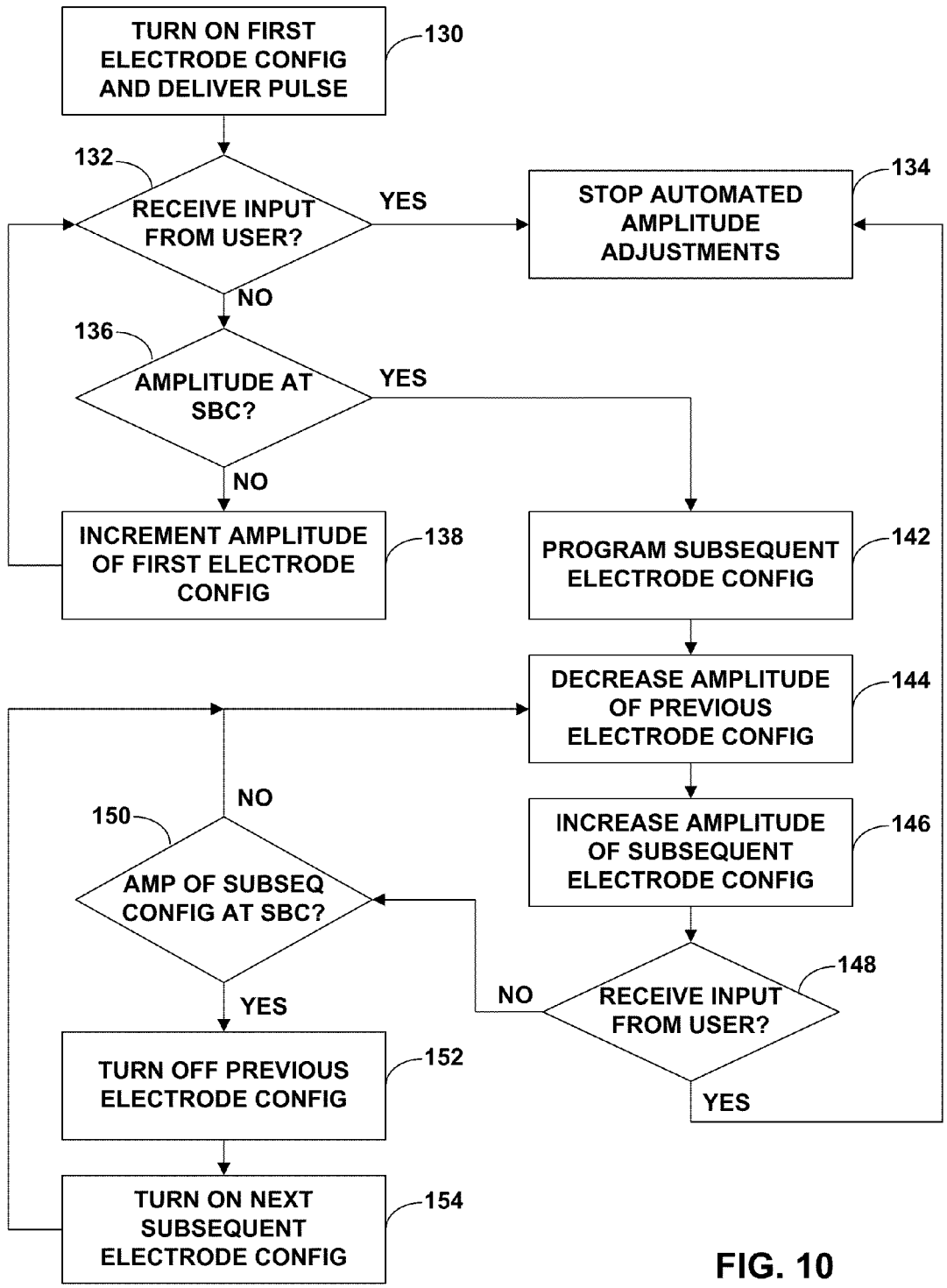
FIG. 10 is a flow diagram illustrating another exemplary operation of a programmer testing electrode combinations.

FIG. 10 is a flow diagram illustrating exemplary operation of a programmer, such as programmer 11 of FIG. 1, testing electrode combinations in a predetermined sequence. The electrode combination testing is performed under user control, with the incremental adjustments occurring automatically until programmer 11 receives input from the user. Initially, programmer 11 controls neurostimulator 14 to turn on a first electrode combination and delivers one or more electrical pulses via the first electrode combination (130). Programmer 11 determines whether it has received input from the user indicating that the amplitude of the stimulation is uncomfortable (132). The user may, for example, be a physician, and the physician may actuate a button when a patient indicates that the stimulation is uncomfortable. When programmer 11 receives input from the user indicating the amplitude of the stimulation is uncomfortable, programmer 11 stops the automated amplitude adjustments (134).

When programmer 11 does not receive input from the user, programmer 11 determines whether the stimulation amplitude of the first electrode combination has reached the target amplitude or SBC level (136). When the stimulation amplitude of the first electrode combination is below the target amplitude, programmer 11 increases the amplitude of the stimulation of the first electrode combination by a step (138). Programmer 11 increases the amplitude by downloading a program update to the neurostimulator via telemetry. The increases in amplitude may occur periodically at a rate of one every few seconds, so that there is sufficient spacing between the amplitude adjustments for the patient to distinguish different stimulation levels and have time to react in the event stimulation quickly becomes uncomfortable. In other embodiments, the rate may be slower or faster.

When the stimulation amplitude of the first electrode combination reaches the target amplitude, programmer 11 turns on a subsequent electrode combination (142). As described above, the subsequent electrode combination may be the next electrode combination in a pre-defined sequence of electrode combinations. In some embodiments, the subsequent electrode combination may be an adjacent electrode combination. Programmer 11 decreases the amplitude of the first electrode combination (144) and increases the amplitude of the subsequent electrode combination by a single step (146). Programmer 11 interleaves the time slots during which stimulation pulses are provided to the first electrode combination and the subsequent electrode combination at a frequency that provides the patient with the feeling of a smooth transition between the electrode combinations.

Programmer 11 determines whether it has received input from the user indicating that the amplitude of the stimulation is uncomfortable after the step (148). When programmer 11 receives input from the user indicating the amplitude of the stimulation is uncomfortable, programmer 11 stops the automated amplitude adjustments (134).

When programmer 11 does not receive input from the user, programmer 11 determines whether the amplitude of the subsequent electrode combination is at the SBC level (150). If the amplitude of the subsequent electrode combination has not reached the SBC level, programmer 11 adjusts the amplitudes of the previous electrode combination and the subsequent electrode combination. Specifically, programmer 11 decreases the amplitude of the previous electrode combination one more step and increases the amplitude of the subsequent electrode combination one more step.

If the amplitude of the subsequent electrode combination has reached the target amplitude, programmer 11 turns off the first electrode combination (152) and turns on the next subsequent electrode combination in the sequence (154). Programmer 11 begins to incrementally shift the two electrode combinations in the same manner to smoothly shift between them. Programmer 11 tests the electrode combinations of the sequence, shifting between each one in accordance with the invention. Programmer 11 may also concurrently monitor for mark input from the user for amplitude adjustment input from the user as described in detail in FIG. 9.

Figure 11:
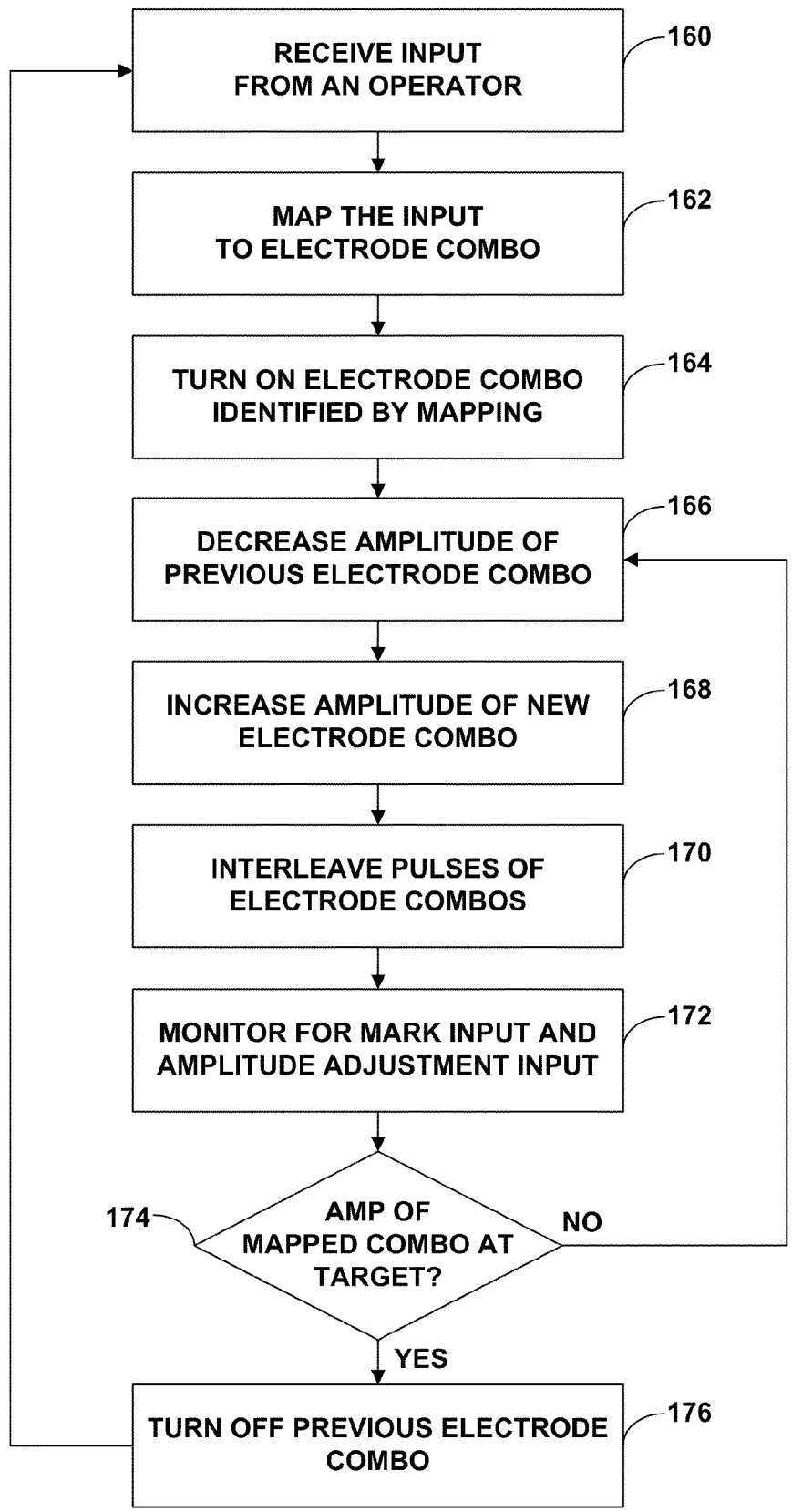
FIG. 11 is a flow diagram illustrating exemplary operation of programmer that receives input from a user to shift between electrode combinations in accordance with the techniques of the invention.

FIG. 11 is a flow diagram illustrating exemplary operation of programmer that receives input from a user, such as programmer 50 of FIG. 5, shifting between electrode combinations in accordance with the techniques described herein. Initially, programmer 50 receives input from a user via controller 54 (160). For example, controller 54 may be a joystick, and the user may manipulate the joystick in a particular direction.

Programmer 50 maps the manipulation of controller 54 to a particular electrode combination (162). Programmer 50 may, for instance, access a map that maps X-Y coordinates of the directional controller to combinations of electrodes on leads 16. Alternatively, programmer 50 may use input from controller 54 to select successive electrode combinations, e.g., by array pointers, without regard to directional or location information. Programmer 50 controls neurostimulator 14 to turn on the electrode combination identified by the mapping (164). Programmer 50 decreases the amplitude of the first electrode combination (166) and increases the amplitude of the subsequent electrode combination by a single step (168). As described above, programmer 50 interleaves the time slots during which stimulation pulses are provided to the first electrode combination and the subsequent electrode combination (170).

Programmer 50 monitors for either mark input or amplitude adjustment input from the user (172). As described in detail above, mark input may be received when the user determines that a particular setting is efficacious. Upon receiving mark input, programmer 50 stores current parameter values, e.g., the amplitude values for one or both of the electrode combinations as well as the current target amplitude.

Amplitude adjustment input may be received at any time during the shifting process. Programmer 50 adjusts the overall intensity of the stimulation in response to receiving input from the user by adjusting one or both of the stimulation amplitudes of the first and subsequent electrode combinations as well as the target amplitude toward which programmer 50 is working. Hence, in this example, the controller supports selection of the electrode combination, while separate amplitude controls may be provided to support incremental adjustment of amplitude from one electrode combination to another.

Programmer 50 determines whether the stimulation amplitude of the mapped electrode combination has reached the target amplitude (174). When the stimulation amplitude of the mapped electrode combination is below the target amplitude, programmer 50 decreases the amplitude of the first electrode combination (166) and increases the amplitude of the subsequent electrode combination by another step (168). Each incremental adjustment of stimulation amplitude may occur automatically, or be contingent on receiving input from the user.

If the amplitude of the mapped electrode combination has reached the target amplitude, programmer 50 turns off the first electrode combination (176). In this manner, the user may manipulate controller 54 to search for an electrode combination that provides effective stimulation to patient 12.

Figure 12:
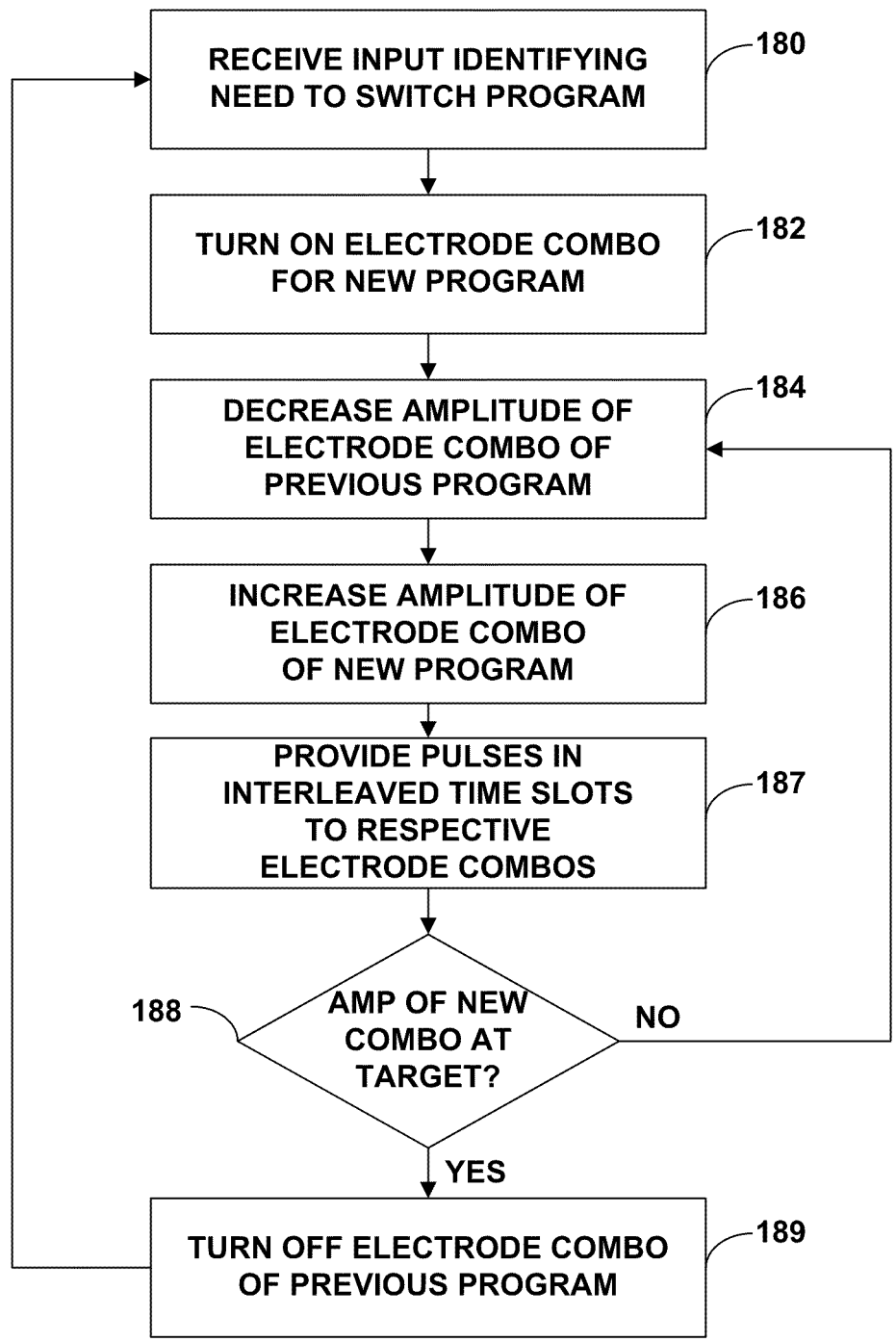
FIG. 12 is a flow diagram illustrating exemplary operation of a neurostimulator shifting between electrode combinations while switching neurostimulation therapy programs.

FIG. 12 is a flow diagram illustrating exemplary operation of a neurostimulator, such as neurostimulator 14 of FIG. 1, shifting between electrode combinations while switching neurostimulation therapy programs. Initially, neurostimulator 14 receives input identifying the need to switch between programs (180). Neurostimulator 14 may include one or more detectors that detect variables such as movement of a patient, heart rate of a patient or the like, and identify the need to switch between programs based on a change in one of the measured variables. For example, neurostimulator 14 may include an accelerometer, and may detect the need to switch programs upon the accelerometer detecting the patient moving from a lying down position to a standing position. Alternatively, neurostimulator 14 may receive input from a patient programmer indicating that the patient would like to change programs, or that the patient will be moving from a lying down position to a standing up position, and correlate that input with the need to switch therapy programs.

Neurostimulator 14 turns on the electrode combination associated with the new program (182). Neurostimulator 14 decreases the amplitude of the electrode combination associated with the previous program (e.g., the lying down program) (184) and increases the amplitude of the electrode combination associated with the subsequent program (e.g., the standing up program) by an incremental step (186). As described above, programmer 50 interleaves the time slots during which stimulation pulses are provided to electrode combinations (187).

Neurostimulator 14 determines whether the stimulation amplitude of the electrode combination associated with the new program has reached the target amplitude (188). When the stimulation amplitude of the electrode combination associated with the new program is below the target amplitude, neurostimulator 14 decreases the amplitude of the electrode combination associated with the previous program (184) and increases the amplitude of the electrode combination associated with the new program by another incremental step (186). If the amplitude of the electrode combination associated with the new program has reached the target amplitude, neurostimulator 14 turns off the electrode combination associated with the previous program (189).

Figure 13:
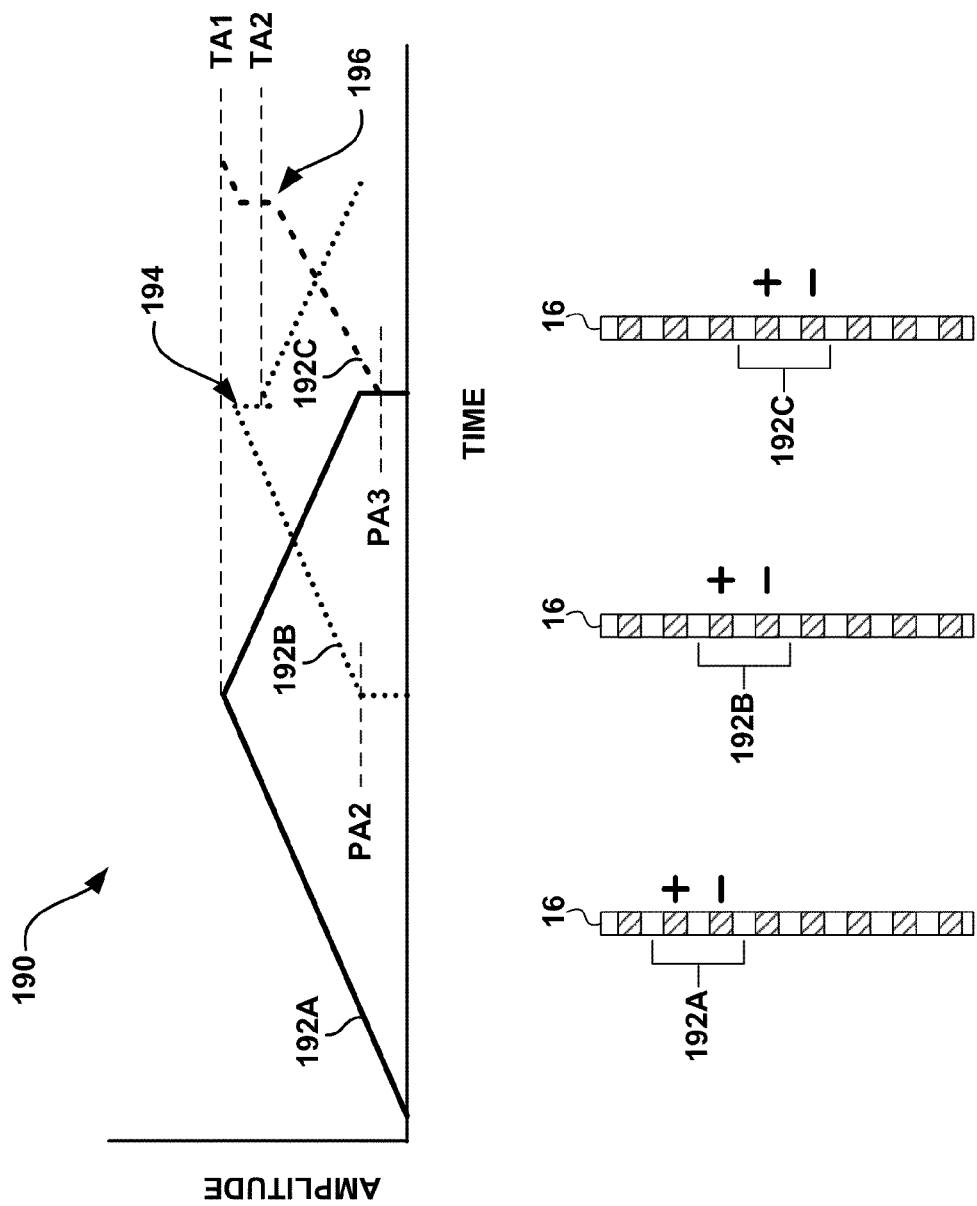
FIG. 13 is an exemplary timing diagram illustrating the shifting process between successive electrode combinations.

FIG. 13 is an exemplary timing diagram 190 illustrating the shifting process between subsequent electrode combinations. Programmer 11 will be used as an example. In particular, timing diagram 190 illustrates the testing of three subsequent electrode combinations, electrode combination 192A, electrode combination 192B, and electrode combination 192C. Timing diagram 190 is described in terms of electrode combination testing, but similar timing mechanisms are utilized to shift between electrode combinations associated with different neurostimulation programs. In FIG. 13, for purposes of illustration, electrode combinations 192A, 192B, and 192C are shown as simple +/− combinations of electrodes on a lead 16. For purposes of illustration, the exemplary progression between electrode combinations 192A, 192B, 192C is a succession of two downward shifts of the +/− combination on lead 16.

Initially, the amplitude of the one or more stimulation pulses delivered by electrode combination 192A is increased until it reaches a target amplitude (labeled TA1 in FIG. 13). The amplitude of the stimulation pulses delivered by electrode combination 192A is increased incrementally, and the incremental increases proceed under user control. As described above, each incremental step may be contingent on input from the user or programmer 11 may proceed through the incremental steps automatically unless it receives input from the user to stop.

Upon reaching the TA1 threshold, programmer 11 controls the neurostimulator to turn on electrode combination 192B and gradually shift between electrode combinations 192A and 192B. In timing diagram 190 illustrated in FIG. 12, the initial amplitude of electrode combination 192B is set at a perception amplitude (labeled PA2 in FIG. 13). PA2 may, for example, be the lowest amplitude at which the patient may detect stimulation on that particular electrode combination. The perception amplitude may, for example, either be detected during a previous calibration session or may be estimated based on calibration of another electrode combination or based on the target amplitude. In some embodiments in which a perception amplitude is not available, the initial amplitude of the subsequent electrode combination 192B may be zero.

Programmer 11 incrementally adjusts stimulation amplitudes of electrode combinations 192A and 192B and interleaves the output pulses in alternating time slots such that the patient feels continuous stimulation. Programmer 11 incrementally decreases the amplitude of electrode combination 192A while concurrently incrementally increasing the amplitude of electrode combination 192B toward TA1 step by step. In timing diagram 190 of FIG. 13, the target amplitude for electrode combination 192B is the same as 192A. The target amplitude for each of electrode combinations may be different, however, and may be tested for during calibration.

During the amplitude increase on electrode combination 192B, programmer 11 receives input from the user indicating that the stimulation has become uncomfortable, and the programmer decreases the overall intensity of the stimulation at arrow 194 in response to the input. As illustrated in timing diagram 190, programmer 11 decreases the target amplitude and the amplitude of the stimulation pulses applied to electrode combination 192B. In some embodiments, programmer 11 may additionally decrease the amplitude of the stimulation pulses applied to the electrode combination whose amplitude is incrementally decreasing (i.e., electrode combination 192A in this example).

Programmer 11 continues to incrementally increase the amplitude of the stimulation pulses delivered to electrode combination 192B toward the reduced target amplitude (labeled TA2 in FIG. 13). Upon reaching TA2, programmer 11 controls the neurostimulator to shut off electrode combination 192A and turn on the next subsequent electrode combination, i.e., electrode combination 192C. Programmer 11 incrementally adjusts stimulation amplitudes of electrode combinations 192B and 192C in the manner described above. In other embodiments, a specified period of time may separate the end of combination 192A and the beginning of combination 192C. In this manner, 192B would operate alone during the transition period. In some embodiments, electrode combination 192A may be shut off prior to electrode combination 192B reaching TA2.

During the amplitude increase on electrode combination 192C, programmer 11 receives input from the user indicating that the stimulation has become too weak, and the programmer increases the overall intensity of the stimulation at arrow 196 in response to the input. As illustrated in timing diagram 190, programmer 11 increases the target amplitude back to the original target amplitude (TA1) and also increases the amplitude of the stimulation pulses applied to electrode combination 192C. Programmer 11 continues to incrementally increase the amplitude of the stimulation pulse delivered to electrode combination 192C toward the original target amplitude.

Figure 14:
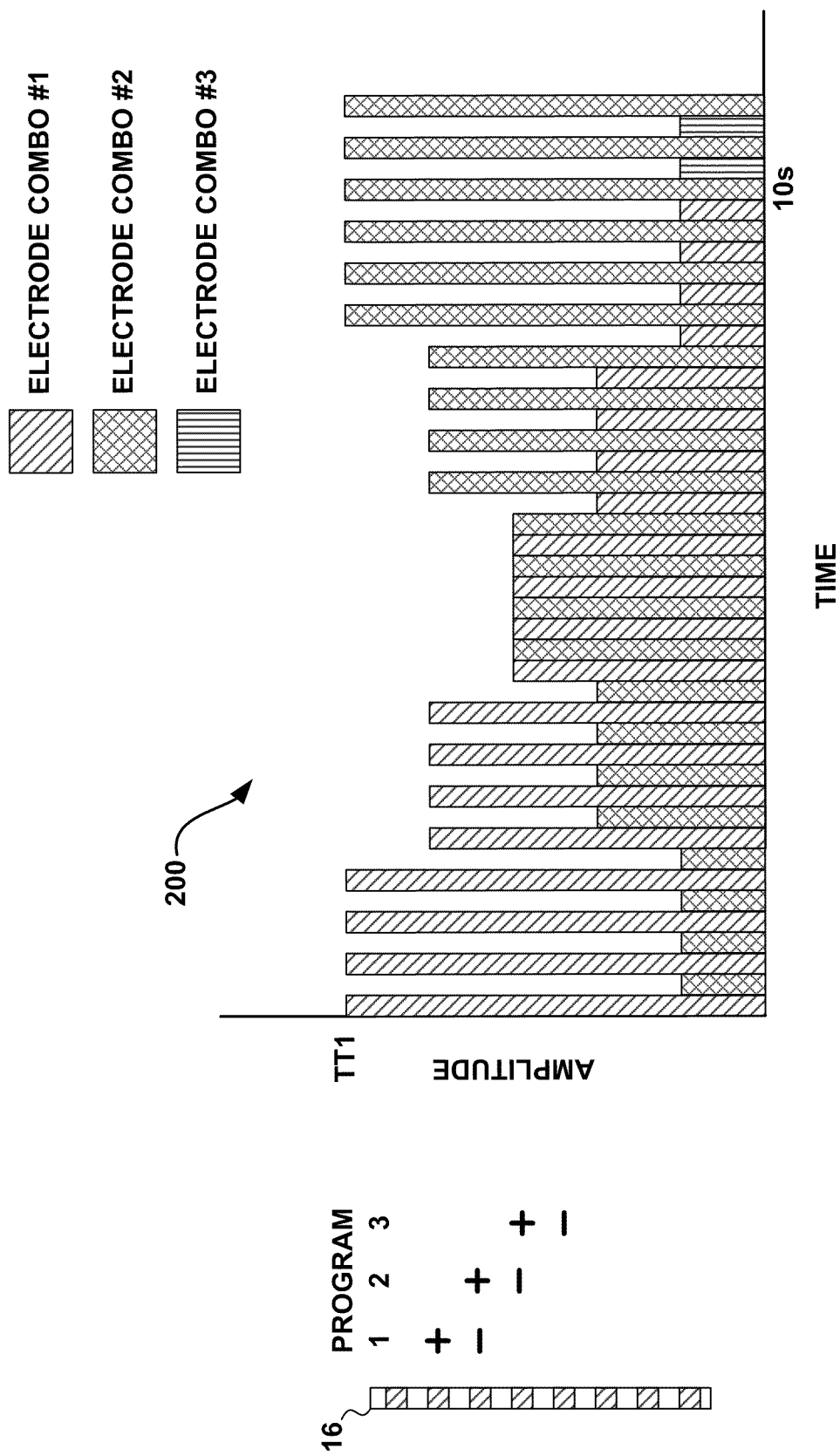
FIG. 14 depicts another exemplary timing diagram illustrating the interleaving of stimulation energy to subsequent electrode combinations in order to provide a smooth shift from a first electrode combination to a second electrode combination.

FIG. 14 depicts another exemplary timing diagram 200 illustrating the interleaving of time slots containing one or more stimulation pulses delivered by different electrode combinations in order to provide a smooth shift from a first electrode combination to a second electrode combination. As described briefly above, programmer 11 interleaves the time slots at a high enough frequency that the patient feels a smooth shift from the first electrode combination to the next. The physiological effects of the stimulation pulses in the alternating time slots appear to occur almost simultaneously and overlap in the patient's perception.

In the example illustrated in timing diagram 200, the entire shift process proceeds over a ten second interval with the stimulation amplitudes being interleaved every one-quarter of a second. Programmer 11 controls neurostimulator 14 to deliver a first stimulation energy via the first electrode combination for 250 milliseconds, then deliver a stimulation energy via the second electrode combination for 250 milliseconds, and then deliver stimulation energy via the first electrode combination for 250 milliseconds and so forth. Hence, the electrode combinations are assigned respective time slots and interleaved at a relatively high frequency to simulate a smooth shifting of energy between the electrode combinations. Within each time slot, multiple pulses of stimulation energy may be applied, according to the pulse width and rate of the stimulation energy. In some embodiments, stimulation energy might not be delivered throughout the entire time slot assigned to a respective electrode combination. For example, the stimulation energy may be delivered via the first electrode combination for only 200 milliseconds of the 250 millisecond time slot. The remaining 50 milliseconds may be a pause where no stimulation energy is delivered by any electrode combination. Consequently, in some embodiments, stimulation may not be delivered during the entire pulse time slot.

Every incremental step in amplitude is therefore applied to patient 12 for two seconds. In particular, programmer 11 controls neurostimulator 14 to deliver stimulation in eight consecutive time slots during each of the amplitude adjustments, e.g., four time slots of pulses for the first electrode combination at an associated stimulation amplitude and four time slots of pulses for the second electrode combination at an associated stimulation amplitude. The time slots for the first and second electrode combinations are interleaved such that they alternate every other time slot. Thus, neurostimulator 14 provides stimulation pulses in a first time slot via a first electrode combination and stimulation pulses in a second slot via the second electrode combination. In some embodiments, neurostimulator 14 may deliver more pulses for each electrode combination before adjusting amplitude. For example, in each time slot, 100 pulses or more may be delivered for each combination at an associated amplitude before an amplitude adjustment of each electrode combination is made. Again, the number of pulses provided in a given time slot will depend on the length of the time slot and the pulse width and pulse rate, but may range from one pulse per time slot, to several pulses per time slot, to a few hundred pulses per time slot. In one example, a time slot is approximately 250 ms in length and carries approximately 250 pulses. In another example, a time slot is approximately 250 ms in length, and carries 200 pulses as well as a 50 ms pause before the next time slot.

The shift between electrodes may occur at different frequencies over different shift periods, and is thus not limited to a ten second shift period with pulses being interleaved every 250 milliseconds. For example, programmer 11 may control neurostimulator 14 to deliver only a single pulse or multiple pulses at each amplitude at each amplitude.

Timing diagram 200 also illustrates the incremental adjustments made to the amplitudes of the stimulation pulses associated with each of the electrode combinations. In the example illustrated in FIG. 14, the amplitudes of the first and second electrode combinations are increased and decreased, respectively, by 20% per step. Programmer 11 may, however, be configured to adjust the amplitudes by any percentage per step.

As shown in timing diagram 200, when the amplitude of the first electrode combination reaches the target amplitude, programmer 11 turns on the second electrode configuration at the perception amplitude level. The perception amplitude level in this example is 20% of the target amplitude. Programmer 11 decreases the amplitude of the first electrode combination and increases the amplitude of the second electrode combination as described in detail above.

For simplicity, in some instances, delivery of neurostimulation energy via different electrode combinations may be accomplished by interleaving on a pulse-by-pulse basis. However, it is not necessary that individual pulses be delivered in each time slot. Rather, a given electrode combination may deliver multiple pulses in an assigned time slot for a first electrode combination, followed by delivery of multiple pulses in the next assigned time slot by a different electrode combination. Therefore, although delivery of stimulation energy occurs on a time-interleaved basis, as described herein, each time slot may include a single pulse or multiple pulses from a given electrode combination.

Figure 15:
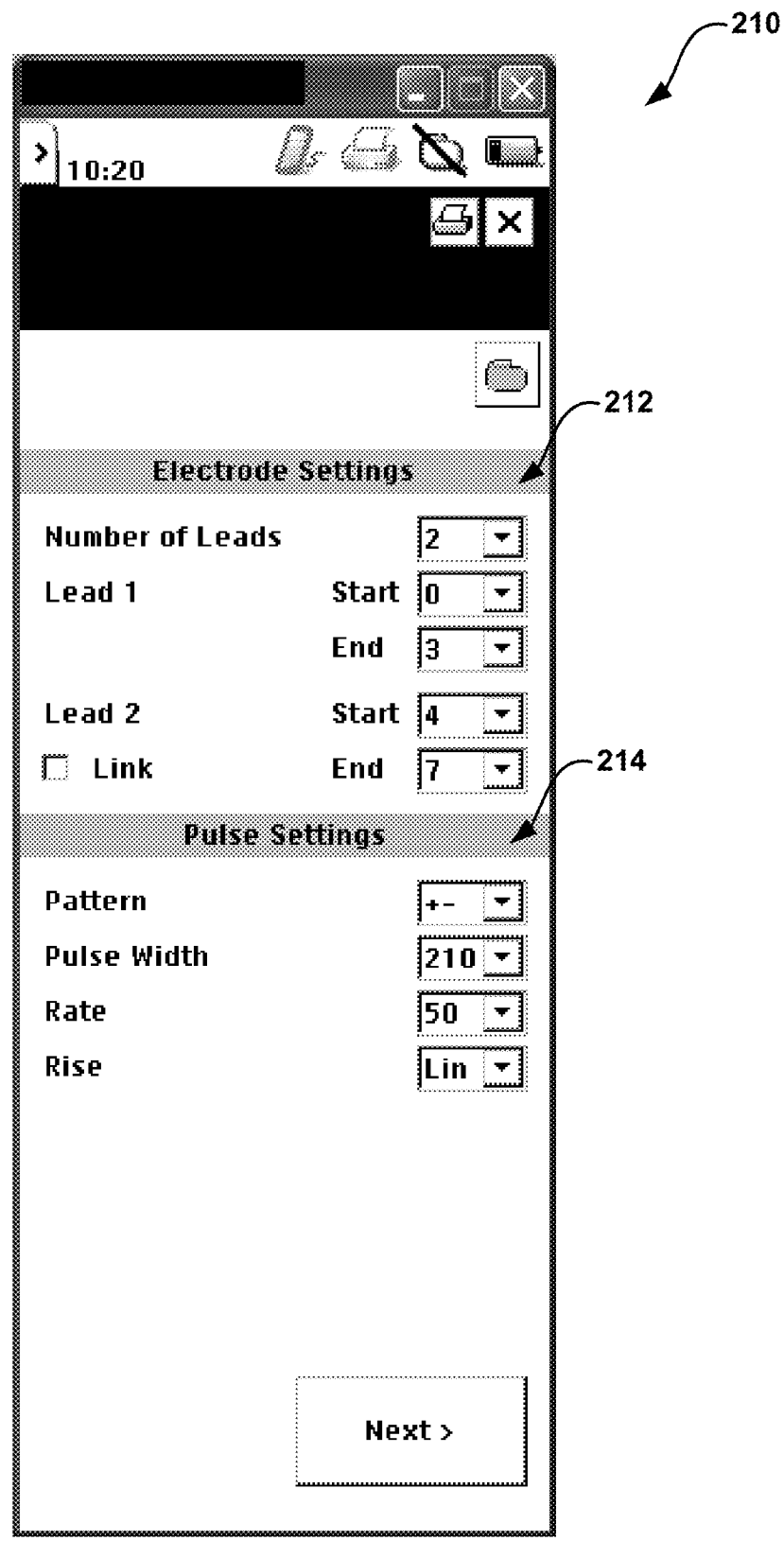
FIG. 15 is a screen illustration showing an exemplary user interface for configuring a programmer for electrode combination testing.

FIG. 15 is a screen illustration showing an exemplary user interface 210 for configuring a programmer for electrode combination testing. Programmer 11 will be used as an exemplary programmer. User interface 210 may be presented on a touch screen display or LCD. User interface 210 includes an electrode setting section 212 and a pulse setting section 214. The user of programmer 11 may interact with electrode setting section 212 to identify the number of leads associated with neurostimulator 14 as well as which electrode to start and end with on each lead. Additionally, the user may interact with electrode setting section 212 to select the portions of each of the leads over which the shifting feature should operate. Electrode setting section 212 may include additional setting options (not shown) for the user.

Pulse setting section 214 includes a number of pull-down menus with which the user may interact to specify the electrode pattern, the pulse width, the rate, and the rise. For example, the user may interact with pulse setting section to indicate whether the electrode pattern is a single bipole, a guarded cathode combination, a single cathode, or any other combination.

Figure 16:
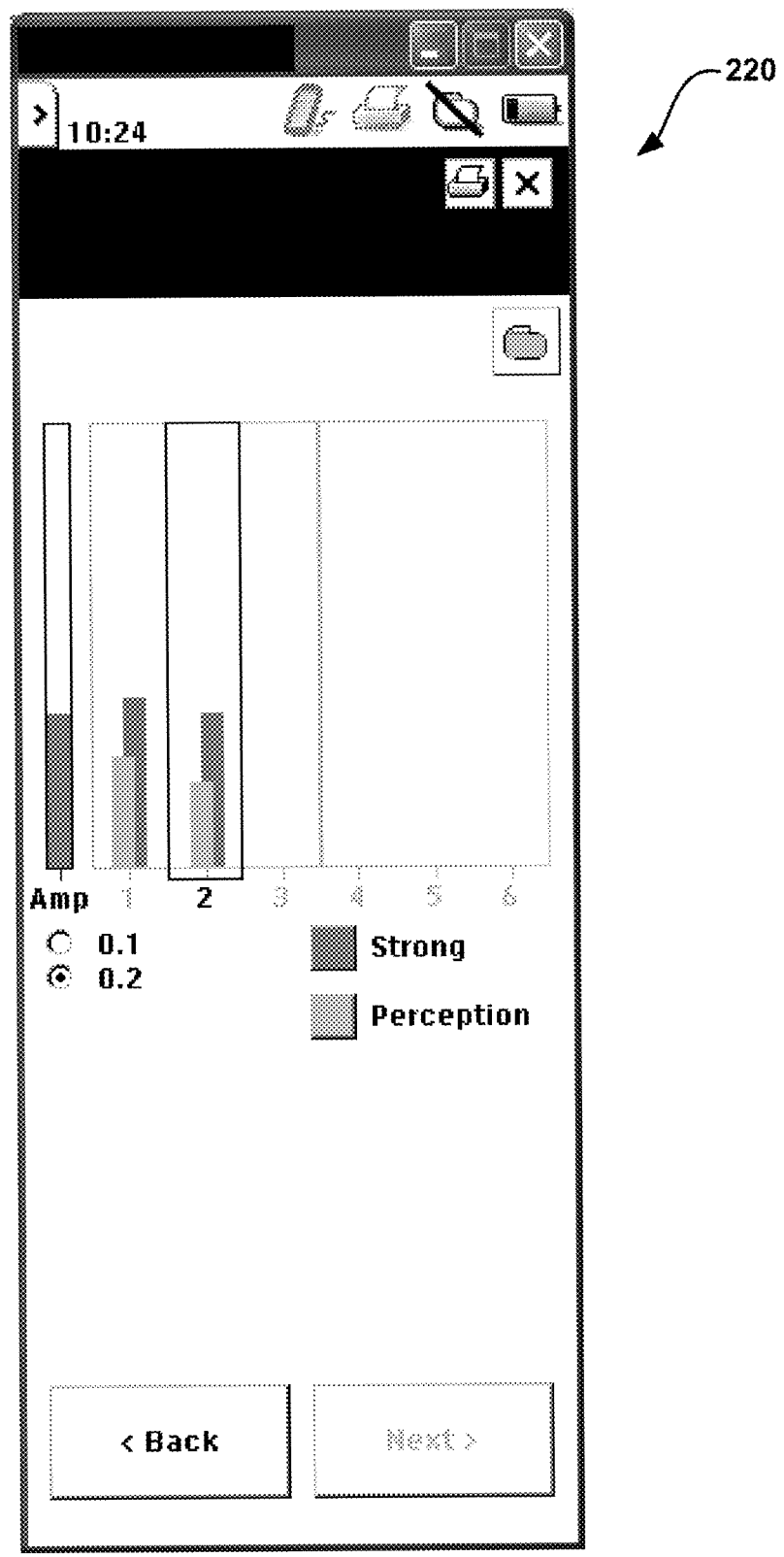
FIG. 16 is a screen illustration showing an exemplary user interface for interacting with a user to calibrate detection and target amplitudes.

FIG. 16 is a screen illustration showing an exemplary user interface 220 for interacting with a user to calibrate detection and target amplitudes. In the example illustrated in FIG. 16, user interface 220 includes calibrated detection and target amplitudes for two electrode combinations. To calibrate detection and target amplitude for an electrode combination, the user identifies which of the electrode combinations to calibrate. The user may, for example, use a peripheral pointing device, such as a stylus, to select one of the electrode combinations. In the example illustrated in FIG. 16, the user is calibrating electrode combination 2.

After selecting the particular electrode combination to calibrate, the amplitude of the one or more stimulation pulses delivered by the selected electrode combination is incrementally increased. The user identifies the amplitude at which he/she perceives the stimulation and the amplitude that provides SBC level stimulation, i.e., the target amplitude. The user may interact with user interface 220 to calibrate any number of the electrode combinations that will be tested. Although the calibration user interface depicted in FIG. 16 is a single user interface for calibrating all the electrode combinations, the user may calibrate the electrode combination using a series of different calibration user interfaces, one for each electrode combination.

Figure 17:
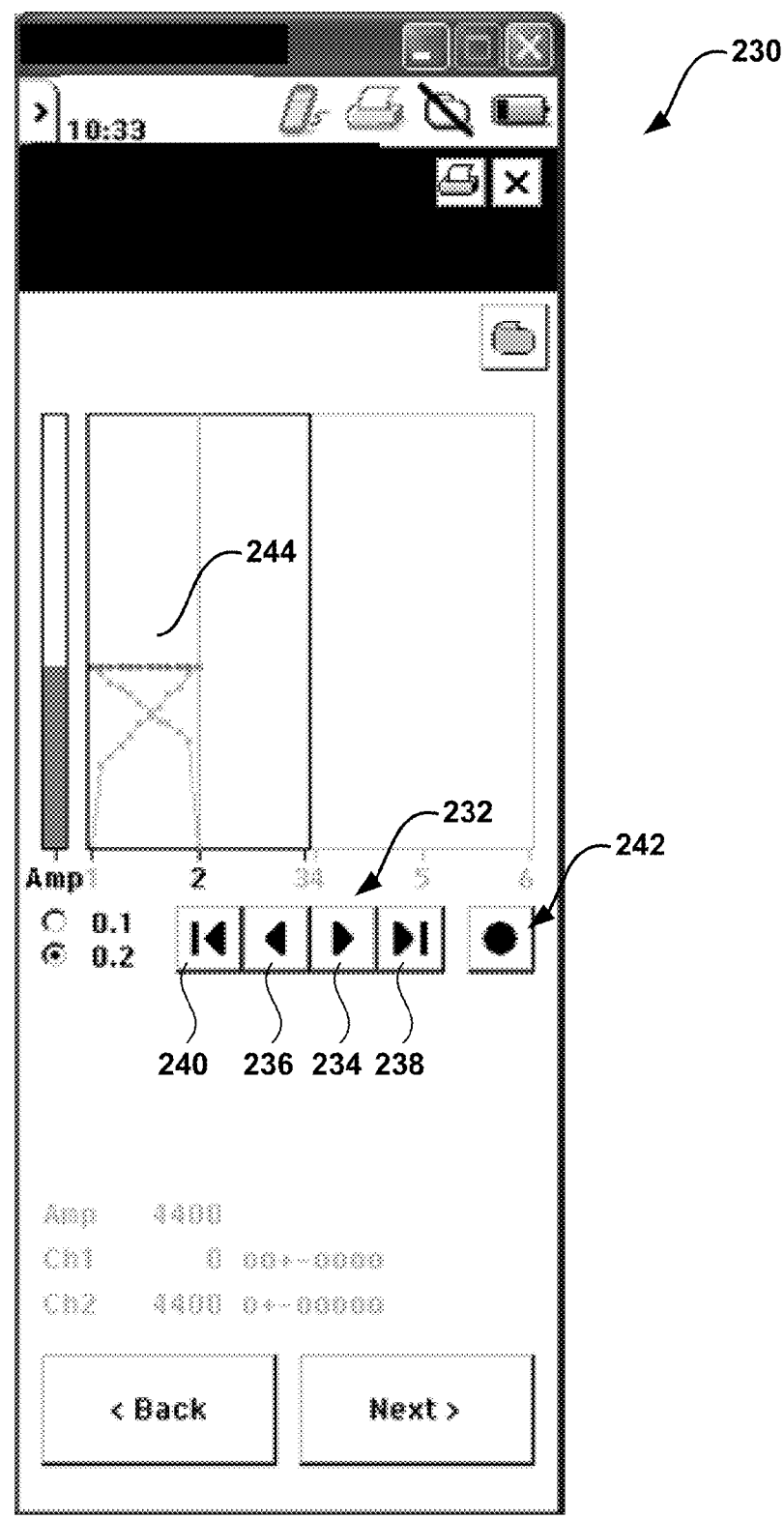
FIG. 17 is a screen illustration showing an exemplary user interface for interacting with a user to control the shift between a first and second electrode combination.

FIG. 17 is a screen illustration showing an exemplary user interface 230 for interacting with a user to control the shift between a first and second electrode combination. User interface 230 may be a touch screen display, and the user may interact with user interface 230 via the display. The user may also interact with user interface 230 using peripheral pointing devices, such as a stylus or mouse.

User interface 230 includes shifting controls 232 for controlling the shift between the first and second electrode combinations. Shifting controls 232 include a forward control 234, a back control 236, a jump forward control 238 and a jump back control 240. In some embodiments, a pause control also may be provided. The user may interact with shifting controls 232 between each incremental step in the shift. In this manner, each step in the shift may be contingent on input from the user. Alternatively, programmer 11 may proceed through the incremental steps automatically until the user interacts with shifting controls 232. Jump back control 240 may go directly to the previous marked point, while jump forward control 238 may go directly to the next marked point.

User interface 230 further includes a mark button 242. Mark button 242 allows the user to indicate settings that provide efficacious results. Upon actuation of mark button 242, programmer 11 stores the settings, e.g., the amplitudes and electrode combinations, and the user may return to those setting to fine tune them. User interface 230 also presents the user with a graph 244 showing the steps of the shift.

Figure 18:
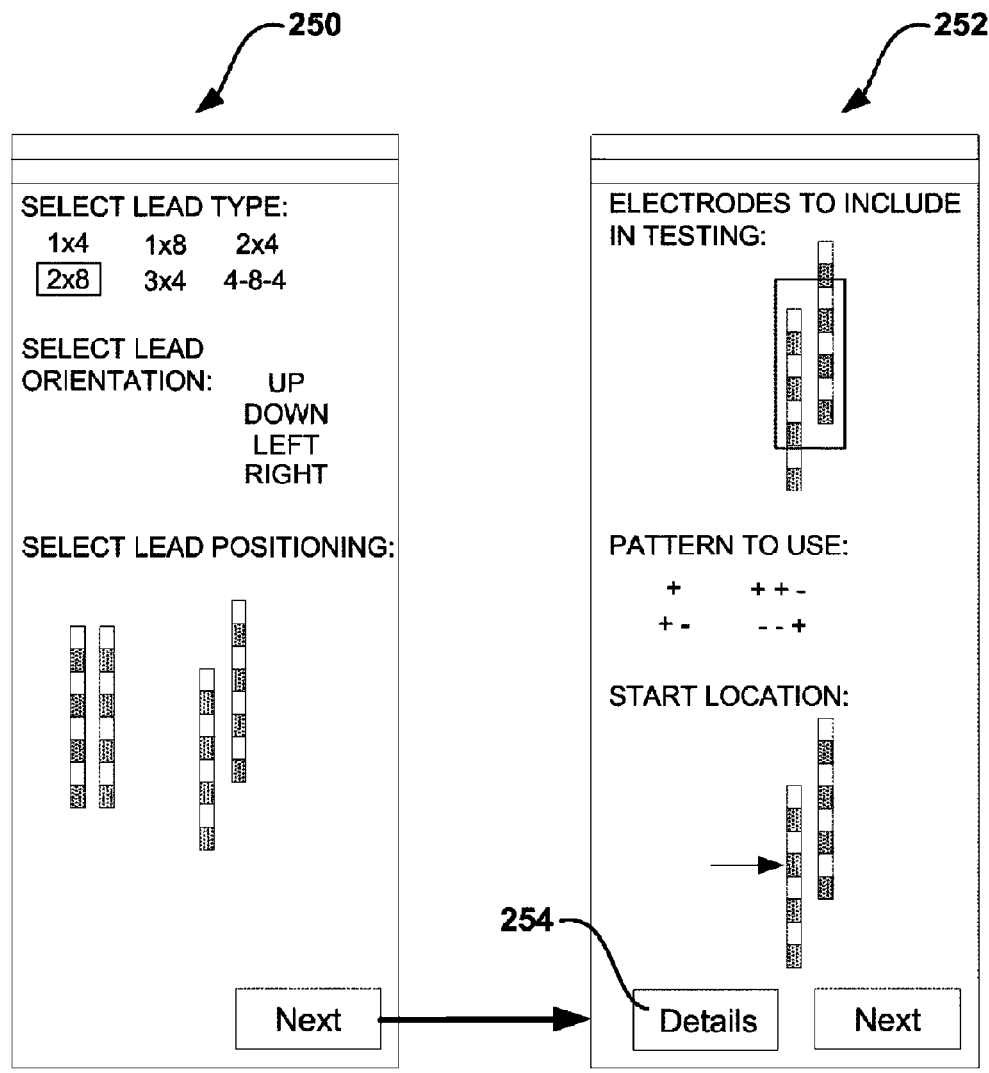
FIG. 18 is a screen illustration showing a series of exemplary user interfaces for configuring a programmer for electrode combination testing.

FIG. 18 is a screen illustration showing a series of exemplary user interfaces for configuring a programmer, such as programmer 11, for electrode combination testing. Initially, a user interacts with user interface 250 to select a lead type, lead orientation, and a lead positioning. The user selects the electrode configuration information on user interface 250 and moves on to the next user interface 252. User interface 252 allows the user to select particular electrodes of the leads to use in testing, the pattern to use, and the starting location of the electrode testing.

The user may also select details button 254, which provides the user with another user interface (not shown in FIG. 18) for specifying amplitude stepping information, such as pulse width, rate, and amplitude increment information. For example, the user may input amplitude increment information such as step size and step rate.

FIG. 19-22 are schematic diagrams illustrating another exemplary programmer 254 to search stimulation programs for controlling an implantable neurostimulator 14 to test electrode combinations. Programmer 254 may be configured as a clinician programmer and may generally correspond in structure and function to the programmers shown in FIGS. 2-5. In the example of FIGS. 19-22, programmer 254 comprises a touch screen display 255 that presents a pair of leads, each including a set of eight electrodes. For example, a first lead 256 includes electrodes 0-7 and a second lead 258 includes electrodes 8-15. The orientation of leads 256, 258 in display 255 is such that the distal end of each lead is at the top of the display. Display 255 further presents an amplitude adjustment area 260, a pulse width adjustment area 262 and a frequency adjustment area 264. A user may select or enter parameter information within areas 260, 262, 264 to control the parameters of the stimulation energy delivered according to a particular program. In addition, display 255 presents device 266 in the form of up/down and side-to-side arrows. A user manipulates device 266 to move a selected pattern of electrodes up or down along a lead or pair of leads, or side-to-side from one lead to another. The up/down or side-to-side indication from device 266 may indicate progression from one electrode combination to another electrode combination in an array of electrode combinations, e.g., without regard to directional information.

Figure 19:
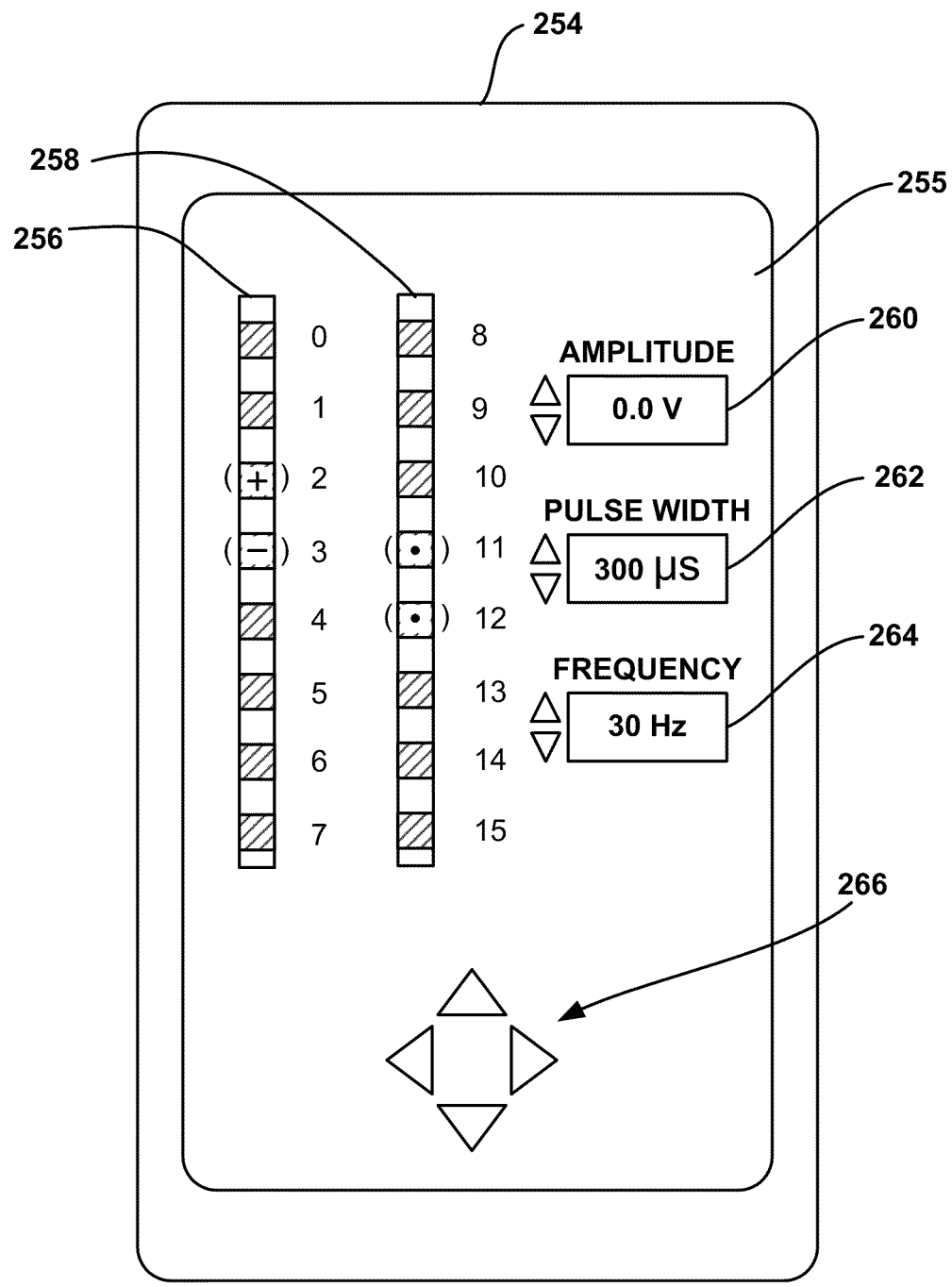
FIG. 19-22 are schematic diagrams illustrating another exemplary programmer to search stimulation programs for controlling an implantable neurostimulator to test electrode combinations.

In the example of FIG. 19, a bipolar combination of electrodes 2 (+) and 3 (−) on lead 256 is to be shifted to a bipolar combination of electrodes 11 (+) and 12 (−) on lead 258. However, the shifting of pulse voltage or current amplitude occurs on an incremental basis over a series of alternating, time-interleaved time slots. In a first time slot, prior to shifting, one or more pulses at a full amplitude are delivered across electrodes 2 and 3 and, in a second time slot, one or more pulses at no amplitude are delivered across electrodes 11 and 12. In a third slot, at the start of the shifting process, one or more pulses with a slightly reduced amplitude are delivered across electrodes 2 and 3 and, in a fourth time slot, a small amplitude is delivered across electrodes 11 and 12. The process continues until, on successive time slots, no amplitude is delivered across electrodes 2 and 3 and a full amplitude is delivered across electrodes 11 and 12. At this point, the incremental shifting of voltage or current amplitude has been completed, such that stimulation is shifted entirely from electrodes 2, 3 to electrodes 11, 12. Notably, the reference to "full" amplitude above does not necessarily mean the maximum amplitude capable of delivery by neurostimulator 14, but rather the entire target amplitude established by a user for delivery of stimulation according to a particular program across a desired electrode combination.

The shifting of amplitude between electrodes 2, 3, as a first electrode combination, and electrodes 11, 12, as a second electrode combination, is performed incrementally. In the example of FIG. 19, each increment of the shifting process is responsive to manipulation of device 266 by a user. In particular, each time the user touches the right-hand side-to-side arrow of device 266, the amplitude is shifted by one increment to the right, i.e., from electrodes 2, 3 on lead 256 to electrodes 11, 12 on lead 258. To execute each incremental shift in response to the user input, programmer 254 sends a corresponding command to neurostimulator 14. As mentioned previously, each incremental shift may be a fixed amount, or vary in a linear or nonlinear manner. In some embodiments, a user may press on an arrow continuously to cause programmer 254 to direct neurostimulator 14 through a series of increments. Hence, the user may press an arrow repeatedly or hold down the arrow to achieve a plurality of shift increments. In other embodiments, the user may not need to continually press on an arrow to achieve a plurality of shift increments. One press of an arrow may cause a shift to the new electrode combination as described until a target amplitude of the new electrode combination is reached. Once the target amplitude is reached, another arrow may be pressed to shift to another electrode combination.

To present the progress of the incremental shifting process to the user, display 255 may identify the electrodes involved in the process, e.g., by highlighting, blinking, or colors, or by brackets or parentheses, as shown in FIG. 19. In addition, the progress of the incremental shifting process may be presented by icons that change their appearance as the shifting process progresses. Prior to shifting, the current electrode combination is indicated and identified by polarity, e.g., plus or minus polarity, while the electrode combination to which stimulation is to be shifted, i.e., the new electrode combination, is not identified yet. At the start of shifting, the current electrode combination still is identified by plus and minus icons, depending on actual polarity, while the new electrode combination is identified by dot icons.

Figure 20:
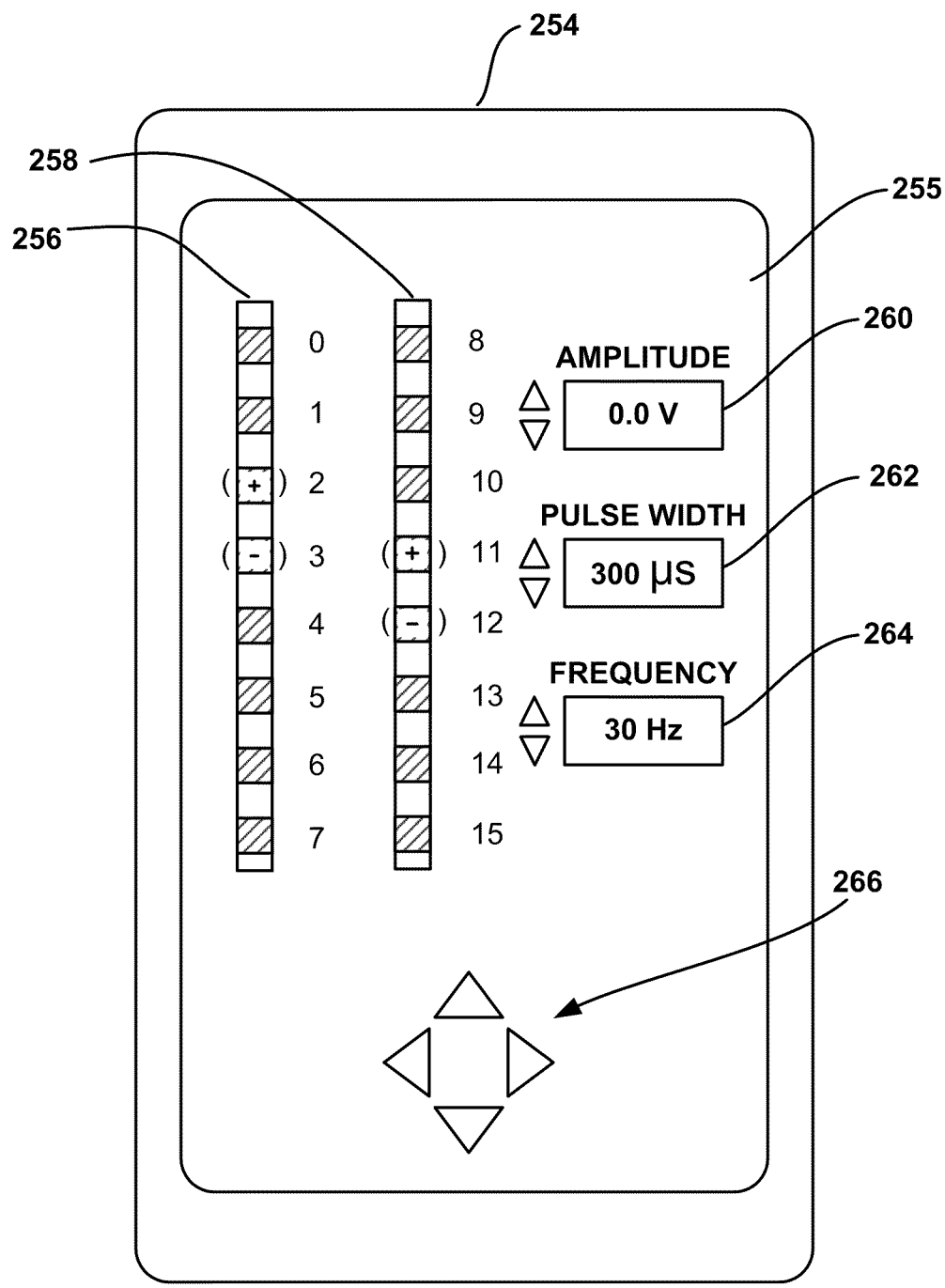
Figure 21:
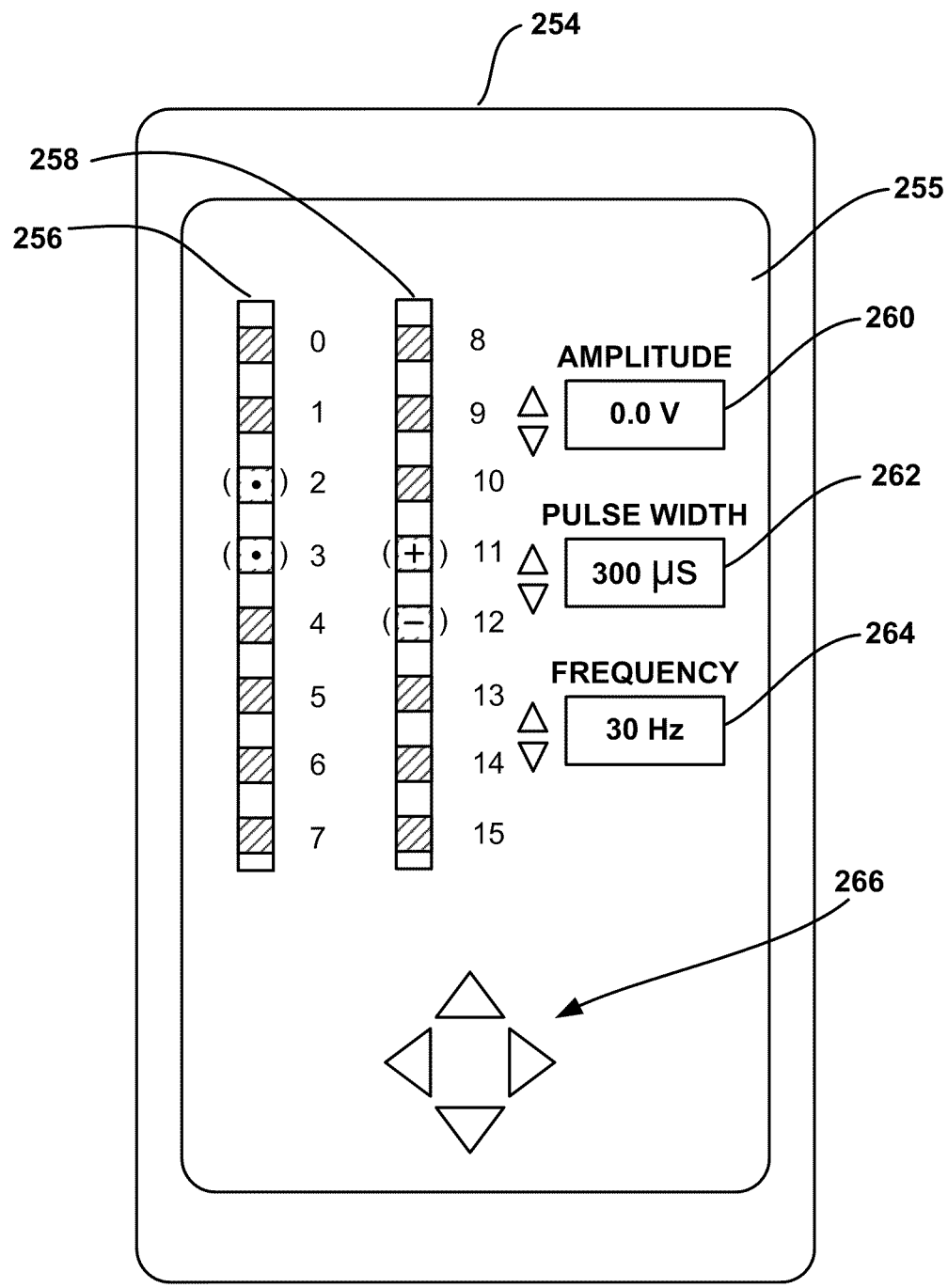

As the current shifting process proceeds, the plus and minus icons for the current electrode combination reduce in size, e.g., as shown in FIG. 20. At the same time, the icons for the new electrode combination progress from dots to small plus and minus icons. As the amount of amplitude shifted from the current electrode combination increases, the plus and minus icons for the current and new electrode combinations become progressively smaller and larger, respectively, until the plus and minus icons for the current electrode combination are transformed into dots, as shown in FIG. 21. Eventually, the dots vanish, leaving only the large plus and minus icons associated with the new electrode combination. Hence, display 255 presents the progression of amplitude shifting in terms of a change in size and/or appearance of icons used to identify the electrodes in the respective electrode combinations. Other devices may be provided to indicate the progression of amplitude shifting, however, such as numeric values, percentages, bar graphs, gauges, meters, hourglasses, and the like.

Figure 22:
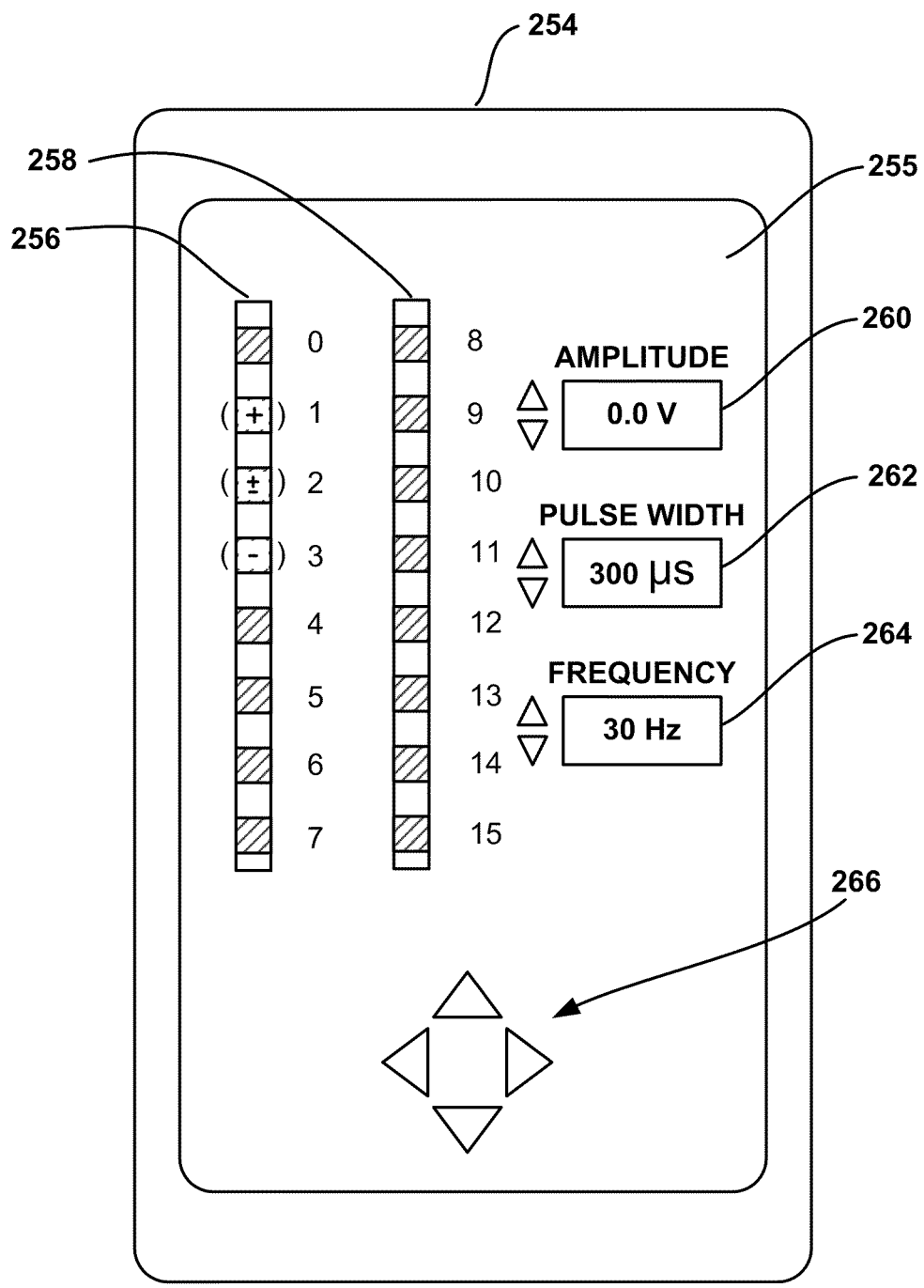

FIG. 22 illustrates a scenario in which the shift from one electrode combination to another requires that a cathode become an anode, or an anode become a cathode. In the example of FIG. 22, a first electrode combination including electrodes 1 and 2 is shifted downward on lead 256 to a new electrode combination including electrodes 2 and 3. In this case, electrode 3 changes polarity from minus to plus. Display 255 may indicate the progression of the incremental amplitude shifting process in a manner similar to that described above with reference to FIGS. 18-21, e.g., by changing the appearance and/or size of the polarity icons. For an electrode, like electrode 2, that transitions from plus to minus, display 255 may present a combined plus/minus (+/−) icon that indicates the mixed status of the electrode during the transition. As the amplitude shifting progresses, the minus icon will become smaller and the plus icon will become larger, until the minus icon vanishes entirely, leaving on the full size plus icon.

Figure 23:
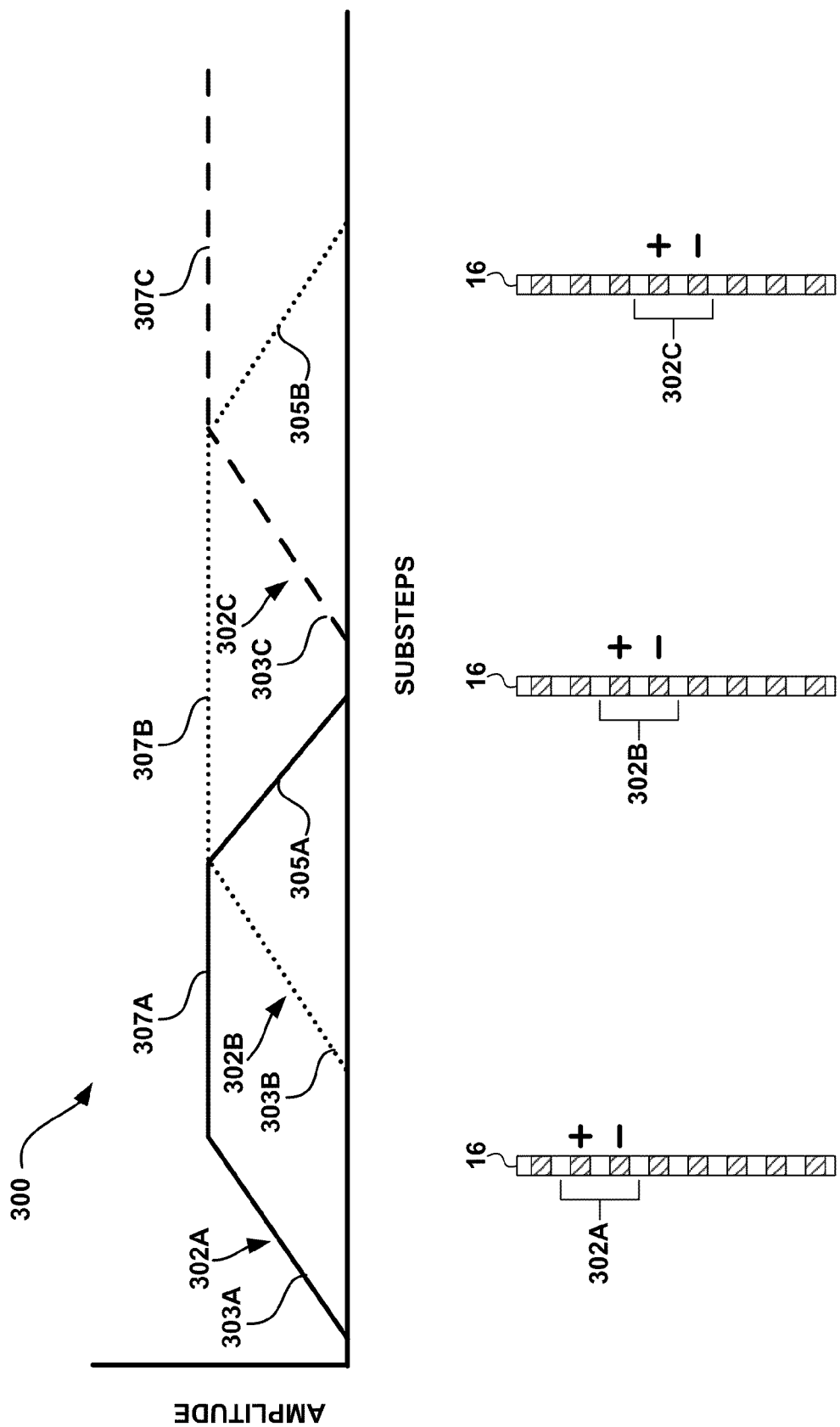
FIG. 23 is an exemplary timing diagram illustrating an alternative process for shifting stimulation energy between successive electrode combinations.

FIG. 23 is an exemplary timing diagram 300 illustrating an alternative process for shifting stimulation energy between successive electrode combinations. Like the process illustrated in FIG. 13, the process of FIG. 23 shifts stimulation energy between different electrode combinations. However, the amplitude (current or voltage) of stimulation energy delivered via an existing electrode combination is maintained at a substantially constant level while the amplitude of stimulation energy delivered via another electrode combination is gradually increased. Accordingly, the amplitudes of the stimulation energy are not simultaneously decreased and increased for the previous electrode combination and the new electrode combination, respectively. Instead, the amplitude for the previous electrode combination is held at a target amplitude level until the amplitude for the new electrode combination reaches the target amplitude level. The target amplitude levels for the previous and new electrode combinations may be the same or different. The process illustrated in FIG. 23 may be implemented by programmer 11 in combination with stimulator 14.

In the example of FIG. 23, timing diagram 300 illustrates the testing of three subsequent electrode combinations, electrode combination 302A, electrode combination 302B, and electrode combination 302C. Timing diagram 300 is described in terms of electrode combination testing, but similar timing mechanisms may be utilized to shift between electrode combinations associated with different neurostimulation programs during normal operation of a stimulator 14. In FIG. 23, for purposes of illustration, electrode combinations 302A, 302B, and 302C are shown as simple +/− combinations of electrodes on a lead 16. For purposes of illustration, the exemplary progression between electrode combinations 302A, 302B, and 302C is a succession of two downward shifts of the +/− combination on lead 16.

Initially, the amplitude of the one or more stimulation pulses delivered by electrode combination 302A is increased until it reaches a target amplitude. The amplitude of the stimulation pulses delivered by electrode combination 302A is increased incrementally, and the incremental increases proceed automatically or under user control. As described above, each incremental step may be contingent on input from the user or programmer 11 may proceed through the incremental steps automatically unless it receives input from the user to stop.

Upon reaching the target amplitude threshold, the amplitude of the stimulation energy delivered via electrode combination 302A levels off to a substantially constant level corresponding to the target amplitude level. For transition to another electrode combination 302B, either automatically or under user control, programmer 11 controls the neurostimulator to turn on electrode combination 302B. Programmer 11 then controls the stimulator to gradually increase the amplitude of stimulation energy delivered via electrode combination 302B. While the amplitude is gradually increased for the new electrode combination 302B, amplitude for the previous electrode combination 302A is maintained at a substantially constant amplitude level.

Hence, the process depicted in FIG. 23 is different from the process of FIG. 13, in which the amplitude for the previous electrode combination is gradually decreased while the amplitude for the new electrode combination is gradually increased. Instead, the amplitude for electrode combination 302A remains substantially constant until the amplitude for the second electrode combination 302B reaches its target amplitude level, which may be the same or different from the target amplitude level for the previous electrode combination 302A.

As in the example of FIG. 13, the initial amplitude of electrode combination 302B in FIG. 23 may be set at a perception amplitude, i.e., the lowest amplitude at which the patient may detect stimulation on that particular electrode combination. Alternatively, as shown in FIG. 23, the amplitude of electrode combination 302B (as well as 302A and 302C) may be ramped upward from an amplitude level of zero. In either case, according to the process shown in FIG. 23, the amplitude of the previous electrode combination is maintained at a substantially constant level while the amplitude of the next electrode combination is gradually ramped upward.

One exception to maintaining the amplitude of the previous electrode combination at a constant level may arise when the user adjusts the target amplitude level, in which case, the levels for the previous electrode combination and new electrode combination may be dynamically rescaled in proportion to the new target amplitude level. Rescaling when the target amplitude is adjusted will be described in further detail below with respect to FIG. 26.

As shown in FIG. 23, programmer 11 incrementally adjusts the stimulation amplitude of electrode combination 302B and interleaves one or more output pulses from electrode combination 302A and electrode combination 302B in alternating time slots. In some embodiments, interleaving of single pulses or groups of pulses may cause the patient to feel a sensation of substantially continuous stimulation. Programmer 11 controls the stimulator to maintain the amplitude of electrode combination 302A substantially constant at the target amplitude while concurrently incrementally increasing the amplitude of electrode combination 302B toward the target amplitude step by step.

Once the amplitude of the new electrode combination 302B reaches the target amplitude, programmer 11 controls the stimulator to gradually decrease the amplitude of the previous electrode combination 302A. Again, programmer 11 may control such amplitude changes automatically or under user control. The amplitude of the previous electrode combination 302A decreases in multiple steps over a period of time until it reaches zero, in which case electrode combination 302A is turned "OFF." At that point, only electrode combination 302B is "ON" and continues to deliver stimulation energy at the target amplitude level.

As shown in FIG. 23, the amplitude "curve" for each electrode combination 302A, 302B, 302C may be characterized by a "frontside" region 303A, 303B, 303C, in which the respective electrode combination increases in amplitude from the initial level to the target level, a "backside" region 305A, 305B, 305C, in which the respective electrode combination decreases in amplitude from the target level to the end level, and a "flat" region 307A, 307B, 307C in which the amplitude of the respective electrode combination remains substantially constant at the target amplitude level.

During the amplitude increase on electrode combination 302B, programmer 11 may receive input from the user indicating that the stimulation has become uncomfortable, and the programmer decreases the overall intensity of the stimulation at arrow 194 in response to such input. In some embodiments, programmer 11 may decrease the target amplitude and the amplitude of the stimulation pulses applied to electrode combination 302B. Also, programmer 11 may decrease the amplitude of the stimulation pulses applied to the previous electrode combination whose amplitude is being held constant or incrementally decreasing (i.e., electrode combination 302A in this example).

In either case, programmer 11 continues to maintain the amplitude of the stimulation pulses delivered to electrode combination 302B at the applicable target level while the amplitude of electrode combination 302A is reduced, eventually to zero. Then, when a transition from the second electrode combination 302B to a third electrode combination 302C is desired, programmer 11 controls the stimulator to maintain the amplitude of electrode combination 302B at a substantially constant level, and begins to gradually increase the amplitude of electrode combination 302C in a series of incremental steps.

When the amplitude of electrode combination 302C reaches a desired target level, programmer 11 controls the stimulator to gradually reduce the amplitude of electrode combination 302B. The process continues until the amplitude of electrode combination 302B reaches zero and the electrode combination 302B is turned "OFF." At that point, the amplitude of electrode combination 302C is held constant until a user changes the target amplitude or a transition to another electrode combination is completed. The transition process continues for each electrode combination evaluated by the user, and may terminate upon user command, when a predetermined sequence of electrode combinations has been evaluated, or when all permitted electrode combinations have been evaluated.

During the amplitude increase on electrode combination 302C, programmer 11 may receive input from the user indicating that the stimulation has become too weak, in which case the programmer may increase the target amplitude level of the stimulation in response to the input. As in the case of intolerable amplitude, an increase when amplitude is too weak likewise may result in a rescaling of the amplitude levels of any electrode combinations on which the amplitude is being increased, decreased or maintained at a constant level.

In general, as shown in FIG. 23, the first electrode combination 302A increases to a target amplitude level in a series of incremental steps. As the amplitude of the second electrode combination 302B gradually increases, the amplitude of the first electrode combination 302A is held constant. When the second electrode combination 302B reaches its target amplitude level, however, the amplitude of the first electrode combination 302A begins to decline.

Both electrode combinations 302A, 302B are at their target amplitude levels, which may be the same or different, for a moment before the amplitude of the first electrode combination 302A begins to decline. Notably, only one of the electrode combinations 302A, 302B changes it amplitude during each time slot. Each step, also referred to as a substep, may include one or more time slots. Hence, the amplitudes of the electrode combinations change on an interleaved basis in alternating time slots. Each time slot carries a single pulse or multiple pulses from the respective electrode combination. As a further characteristic of the process of FIG. 23, in some embodiments, at least one of the two electrode combinations is always at its target amplitude level.

The amplitude curve for each electrode combination may be asymmetric. In particular, the number of substeps required for the amplitude to increase from the initial amplitude level (e.g., zero) to the target amplitude level may be greater than the number of substeps required for the amplitude to decrease from the target amplitude level to the ending amplitude level. As an illustration, the amplitude for each electrode combination 302A, 302B or 302C may require nine "forward" substeps to reach the target amplitude level. The substeps are forward in the temporal sense. Again, substeps refer to the amplitude increase or decrease in each time slot allocated to a respective electrode combination 302A, 302B or 302C.

The existing electrode combination remains at the target amplitude level until the next electrode combination reaches that target amplitude level, at which time the amplitude for the existing electrode combination begins to decrease. Although nine forward substeps are required, per this illustration, for the electrode combination to reach the target amplitude level, only five forward substeps are required for the amplitude to be reduced to its final amplitude, e.g., zero. Hence, with nine forward substeps to reach the target amplitude level, and only five forward substeps to reach the final amplitude level, the amplitude curve for the electrode combination can be considered asymmetric in the sense that ascent requires more substeps than descent.

In this illustrative example, there may actually be eighteen substeps for each electrode combination. When the amplitude decreases from the target amplitude level, however, movements in the "forward" direction may include only odd- or even-numbered substeps. In other words, even or odd steps may be skipped as the amplitude decreases from the target amplitude level to the ending amplitude level. If even substeps are skipped, for example, only five substeps are required to cover the space of nine substeps, for a total of 14 forward substeps from start to end, plus any number of time slots during which the electrode combination may be held at the target amplitude level.

Notably, programmer 11 may permit the user to transition between electrode combinations in both forward and reverse. Forward and reverse refer to movement along the substep or time axis in FIG. 23. Hence, a user may move forward by increasing stimulation amplitude on an electrode combination 302C and then eventually decreasing amplitude upon completion of transition to another electrode combination 302B. Likewise, the user may move in reverse, e.g., by increasing amplitude toward the target amplitude level along the backside region 305, decreasing amplitude toward the initial amplitude value along the frontside region 303, or moving in forward or reverse along the flat region 307. If the user shifts forward past the point at which the next electrode combination (e.g., 302B) has reached its target level, forward substeps to decrease the amplitude of the previous combination (e.g., 302A along backside region 305A) proceed only in odd-numbered substeps. However, substeps in the "reverse" direction, such that the amplitude of the previous combination (e.g., 302A along backside region 305A) increases along the backside region 305A, may include every substep. In this case, the even steps along backside region 305A are not skipped when going in reverse.

Consequently, forward and reverse movement along frontside region 303A requires nine substeps in each direction, while forward movement along backside region 305A requires five odd substeps (with skipping of even substeps) and reverse movement along backside region 305A requires all nine even and odd substeps. Hence, in the example of FIG. 23, the number and size of amplitude increments during shifting from one electrode combination to another electrode combination is not necessarily uniform. Although the frontside and backside regions 303A, 305A of the amplitude curve include eighteen substeps, the number of substeps is provided for purposes of illustration and should not be considered limiting of the various embodiments of the invention described in this disclosure. Rather, different numbers of substeps and different skipping algorithms may be chosen as deemed appropriate for a given application.

Programmer 11 may be configured, in some embodiments, to permit a user to eliminate one of two consecutive electrode combinations upon conclusion of evaluation of the combinations. With reference to FIG. 23, for example, upon transitioning between electrode combinations 302A, 302B and 302C, the user may determine that one of the electrode combination 302B is undesirable or at least no more effective than the adjacent electrode combinations 302A and 302C. In this case, the user may choose to eliminate electrode combination 302B. As a result, the stimulator applies only one active electrode combination (302A or 302C), instead of two active combinations in an overlapping manner (e.g., 302A and 302B or 302B and 302C).

A single active program draws less energy than two active programs, promoting increased battery longevity in the stimulator. The user can then independently refine the stimulation parameters, e.g., amplitude, frequency, pulse width, and electrode polarity, for each electrode combination 302A, 302C by determining their independent effects. In this manner, post-processing to eliminate electrode combinations reduces the number of active programs applied during the shifting process to promote increased battery life as the user continues to evaluate refinements to the electrode combinations and associated parameters.

Figure 24:
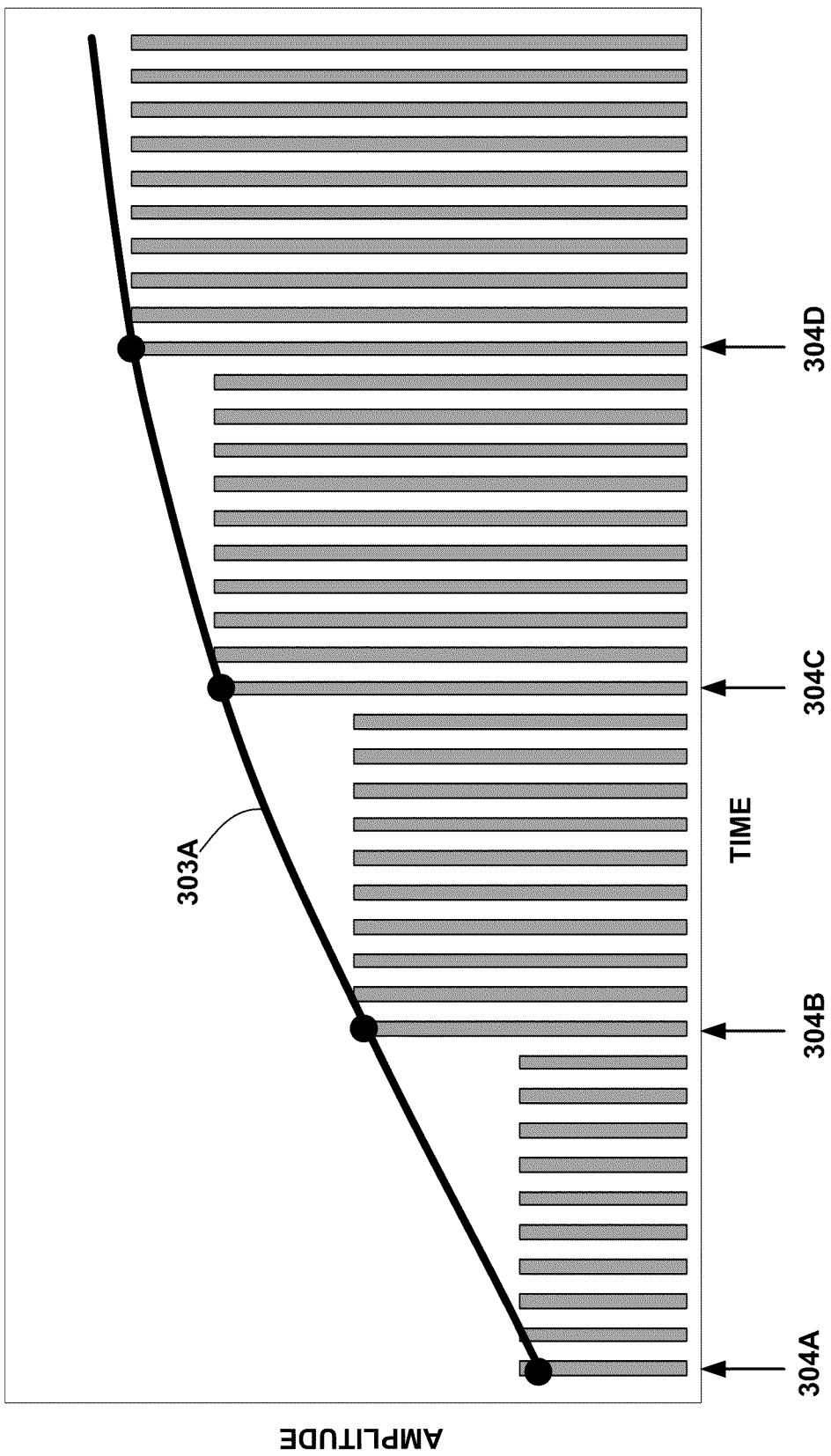
FIG. 24 is an exemplary timing diagram illustrating a gradual increase in stimulation energy delivered via a selected electrode combination in accordance with the alternative shifting process of FIG. 23.

FIG. 24 is an exemplary timing diagram illustrating a gradual increase in stimulation energy delivered via a selected electrode combination in accordance with the alternative shifting process of FIG. 23. The diagram of FIG. 24 represents the first four substeps 304A, 304B, 304C, 304D of the frontside region of the amplitude curve for a particular electrode combination. Again, the frontside and backside region of the amplitude curve may have nine substeps, subject to skipping of even substeps during forward movement in the backside region.

In the example of FIG. 24, each substep includes ten stimulation pulses. Although successive substeps 304A, 304B, 304C, 304D are shown adjacent one another in time, each substep may be delivered on an alternating basis with a substep for another electrode combination. If stimulation is delivered independently via a single electrode combination, however, the substeps may be delivered successively. In general, the upward progression of substeps 304A, 304B, 304C, 304D defines a smooth frontside curve 303A, with the dots in FIG. 24 representing substep transition points.

Figure 25:
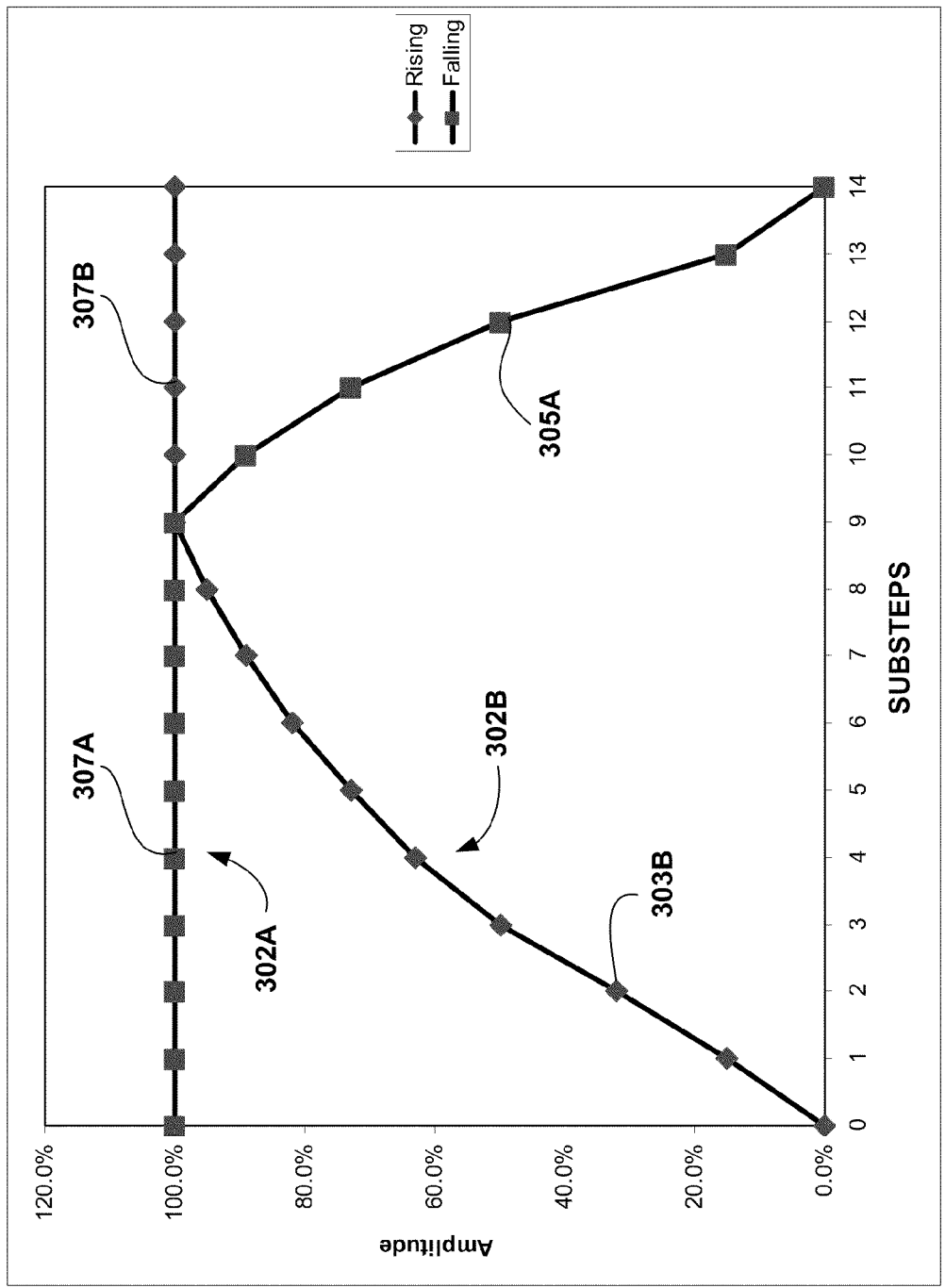
FIG. 25 is an exemplary graph illustrating a process for shifting stimulation energy from a first electrode combination to a second electrode combination in accordance with the alternative shifting process of FIG. 23.

FIG. 25 is an exemplary graph illustrating a process for shifting stimulation energy from a first electrode combination to a second electrode combination in accordance with the alternative shifting process of FIG. 23. FIG. 25 illustrates transition between electrode combinations 302A and 302B by shifting amplitude. In particular, FIG. 25 shows flat region 307A, which represents the maintenance of the first electrode combination 302A at a substantially constant target amplitude level while the amplitude for the second electrode combination 302B gradually increases along front-side region 303B. In addition, FIG. 25 shows flat region 307B of second electrode combination 302B as amplitude for the first electrode combination 302A gradually decreases along the backside region 305A.

In the example of FIG. 25, the front-side and back-side regions are asymmetrical. Again, the amplitude reduction along the back-side region is accelerated relative to the amplitude increase along the front-side region. In other words, the reduction takes less sub-steps than the increase due to substep skipping. In total, it takes fourteen sub-steps to go from one full shift at which first electrode combination 302A is at the target amplitude level and the next electrode combination 302B is at its initial amplitude level, to the next full shift at which the first electrode combination is at its end amplitude level and the next electrode combination is at its target amplitude level.

Figure 26:
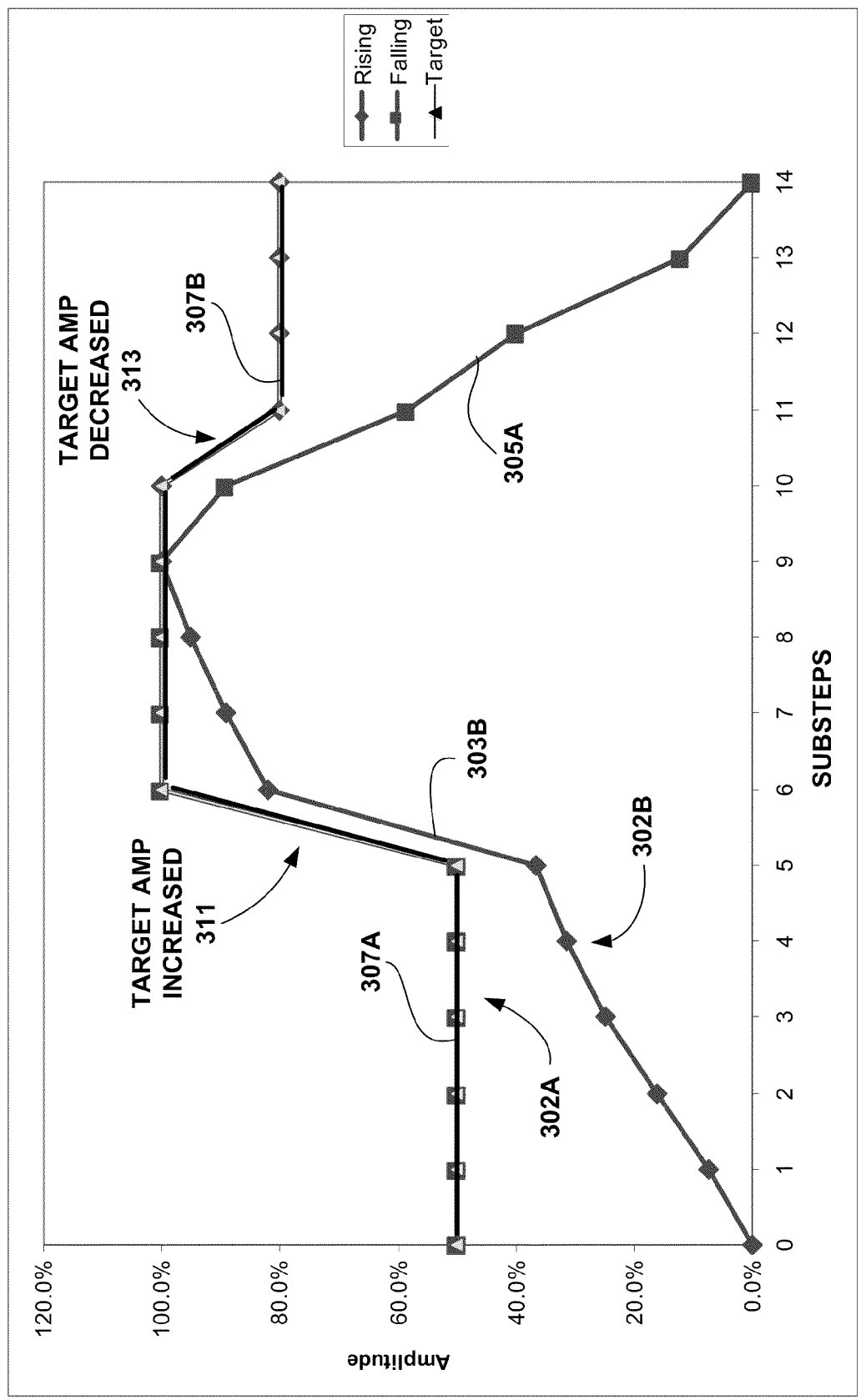
FIG. 26 is an exemplary graph illustrating rescaling of the shifting process of FIG. 25 when a target stimulation amplitude is increased or decreased in accordance with the alternative shifting process of FIG. 23.

FIG. 26 is an exemplary graph illustrating rescaling of the shifting process of FIG. 25 when a target stimulation amplitude is increased or decreased in accordance with the alternative shifting process of FIG. 23. In the example of FIG. 26, as the amplitude of first electrode combination 302A is held constant at the target level, and the amplitude of second electrode combination 302B increases gradually along front-side region 303B, the user increases the target amplitude level. In response, programmer 11 controls the stimulator to increase the target amplitude levels, resulting in a rescaling of the amplitude curves upward in the region identified by reference numeral 311. Following the rescaling, the amplitude continues along its ordinary course, until the user adjusts the target amplitude level downward, resulting in a rescaling of the amplitude curves downward in the region identified by reference numeral 313.

Figure 27:
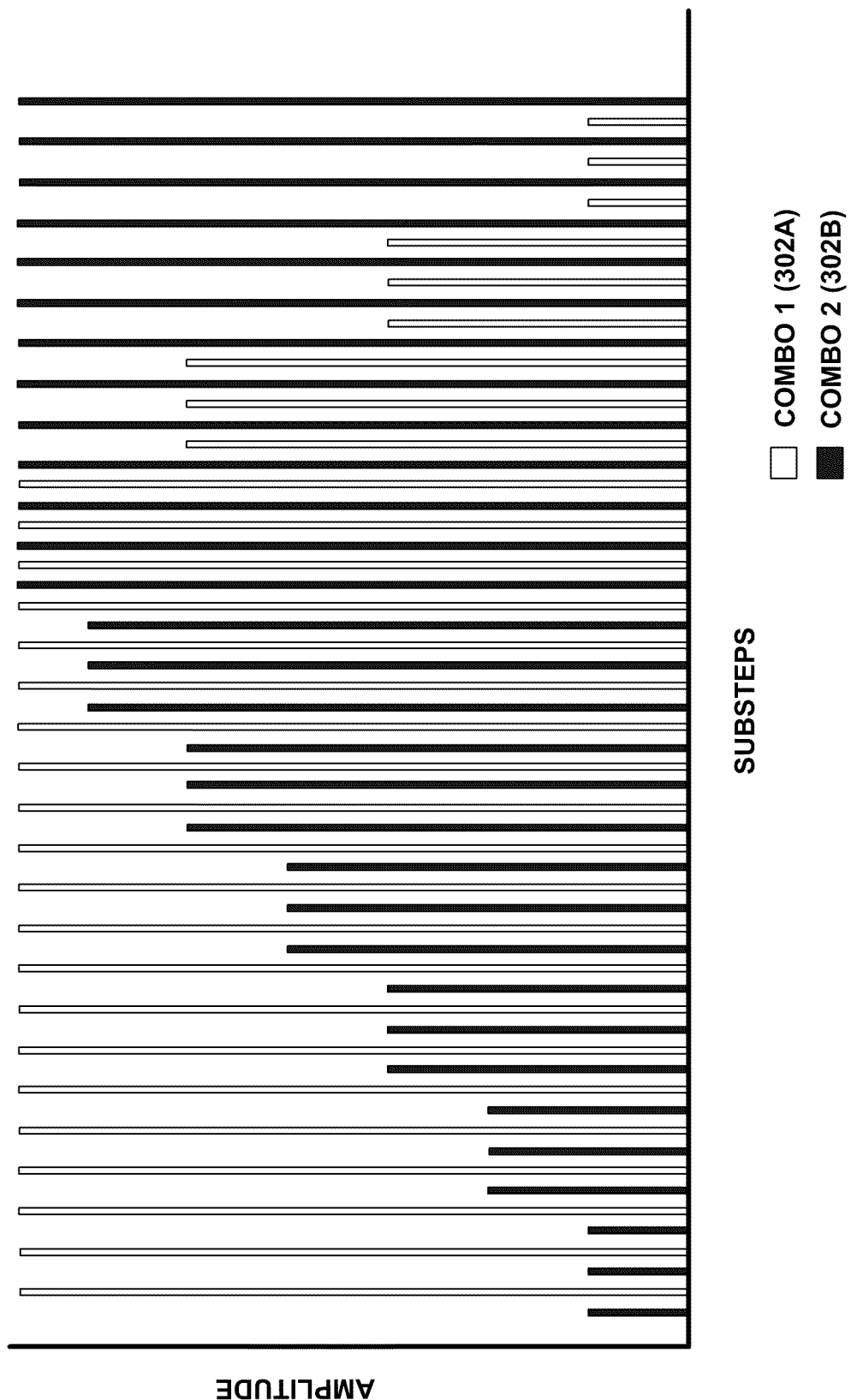
FIG. 27 is an exemplary graph illustrating the interleaving of stimulation energy to subsequent electrode combinations in order to provide a smooth shift from a first electrode combination to a second electrode combination in accordance with the alternative process of FIG. 23.

FIG. 27 is an exemplary graph illustrating the interleaving of stimulation energy to subsequent electrode combinations in order to provide a smooth shift from a first electrode combination to a second electrode combination in accordance with the alternative process of FIG. 23. The white columns show the amplitude of one or pulses delivered in respective time slots for first electrode combination 302A. The black columns show the amplitude of one or more pulses in respective time slots for second electrode combination 302B. FIG. 27 shows a gradual increase of the amplitude of electrode combination 302B over a series of substeps. Each substep includes one or more time slots, and each time slot includes one or more stimulation pulses.

In the example of FIG. 27, each substep includes three time slots, and the front-side region include seven sub-steps. The time slots are allocated to for delivery of stimulation pulses via electrode combinations 302A and 302B on an alternating basis. FIG. 27 also shows a gradual decrease in the amplitude of electrode combination 302A over a series of three substeps. The number of sub-steps and time slots per sub-step are both reduced in FIG. 27, relative to the numbers discussed above with respect to FIG. 23, for ease of illustration. Accordingly, an implementation may include more sub-steps and more time slots per sub-step. In addition, the amplitude increase or decrease per step may be greater or lesser than that shown in FIG. 27. Also, the sub-steps may progress along a logarithmic curve, rather than a linear curve.

Figure 28:
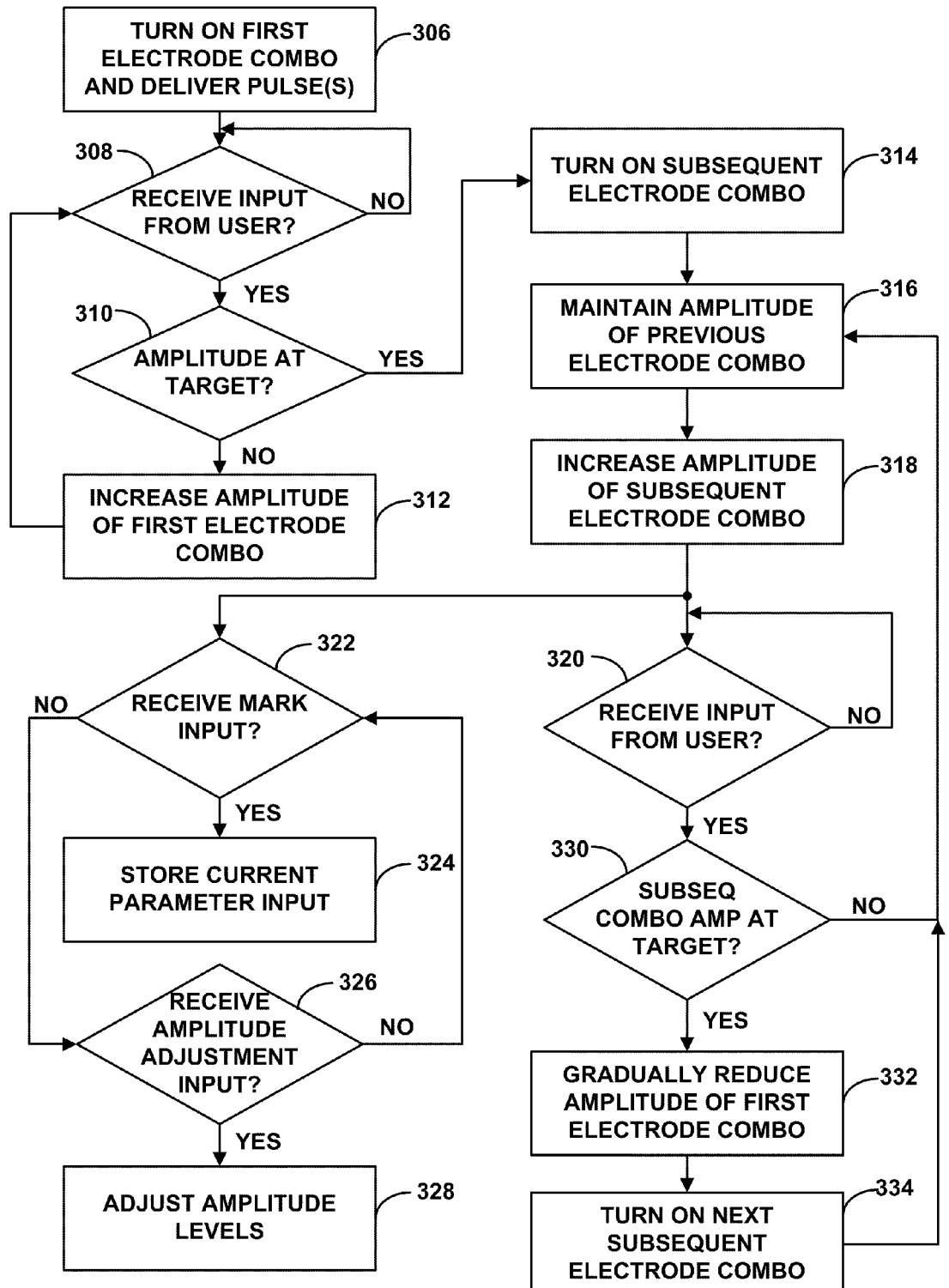
FIG. 28 is a flow diagram illustrating exemplary operation of a programmer testing electrode combinations in accordance with the alternative process of FIG. 23.

FIG. 28 is a flow diagram illustrating exemplary operation of a programmer testing electrode combinations in accordance with the alternative amplitude shifting process of FIG. 23. FIG. 28 generally corresponds to FIG. 9, but illustrates a different approach in which the amplitude of the previous electrode combination is maintained at a constant level during gradual increase of the amplitude of another electrode combination. In the example of FIG. 28, electrode combination testing is performed under user control, with each incremental step contingent on receiving input from the user. Initially, programmer 11 controls neurostimulator 14 to select a first electrode combination and delivers a pulse or group of pulses in a time slot via the first electrode combination (306). The user may specify which electrode combination programmer 11 should test during initial configuration.

Programmer 11 next determines whether it has received input from the user (308) for an increase in amplitude of the stimulation energy delivered via the first electrode combination 302A. The user may, for example, be a physician, and the physician may actuate a button when a patient indicates that the pulse amplitude is comfortable. In another embodiment, patient 12 may be the user, thereby eliminating the need for communication between the physician and patient 12. In the example of FIG. 28, programmer 11 does not increment the stimulation amplitude any further until input is received from the user.

Upon receiving input from the user to indicate that the stimulation amplitudes are comfortable, programmer 11 determines whether the stimulation amplitude of the first electrode combination has reached the target amplitude (310). When the stimulation amplitude of the first electrode combination 302A is below the target amplitude, programmer 11 increases the amplitude of the stimulation of the first electrode combination by a step (312), and waits for user input (308).

When the stimulation amplitude of the first electrode combination reaches the target amplitude, programmer 11 turns on a subsequent electrode combination 302B (314). The subsequent electrode combination 302B may be the next electrode combination in a pre-defined sequence of electrode combinations. Alternatively, the next electrode combination 302B may be selected in response to input from the user, such as time-domain or sequence-domain input identifying a time or position within a sequence, or planar input identifying a direction or location.

Programmer 11 maintains the amplitude level of the first electrode combination 302A (316) at a constant target level, and increases the amplitude of the subsequent electrode combination by a single step (318). The step may be a fixed linear step or an exponential or other algorithmic change such as a logarithm. For example, the first step may be 10% of the target amplitude. As described above, programmer 11 interleaves time slots containing one or more stimulation pulses provided to the first electrode combination and the subsequent electrode combination. The time slots are interleaved at a frequency that provides the patient with the feeling of a smooth shift between the electrode combinations.

Programmer 11 waits to receive user input indicating that the stimulation amplitude remains comfortable after step (320). Programmer 11 concurrently monitors for mark input from the user (322). Mark input may be received when a user determines that a particular setting is efficacious. Upon receiving mark input, programmer 11 stores current parameter values (324). For example, programmer 11 may store the amplitude values for each of the electrode combinations, i.e., the first electrode combination and the subsequent electrode combination. Additionally, programmer 11 may store the current target amplitude. Programmer 11 may return to the marked settings at a later time to allow the user to optimize the parameters.

Programmer 11 also monitors for amplitude adjustment input from the user (326). Amplitude adjustment information may be received at any time during the shifting process. The user can increase or decrease the overall intensity of stimulation to maintain comfortable sensations that are strong enough to evaluate the efficacy of the combinations. Programmer 11 adjusts the overall intensity of the stimulation in response to receiving input from the user (328). For example, programmer 11 may adjust one or both of the stimulation amplitudes applied to the first and subsequent electrode combinations as well as the target amplitude toward which programmer 11 is working. After adjusting the stimulation amplitudes (328), the process of FIG. 28 may continue, e.g., on an iterative basis, to evaluate additional electrode combinations and stimulation parameter values.

Programmer 11 determines whether the amplitude of the subsequent electrode combination is at the target amplitude (330). If the amplitude of the subsequent electrode combination has not reached the target amplitude, programmer 11 maintains the amplitude of the previous electrode combination 302A at the constant target level, and increases the amplitude of the subsequent electrode combination 302B. Specifically, programmer 11 increases the amplitude of the subsequent electrode combination one more step. In some embodiments, as mentioned above, the step size may be different between decreasing amplitude or increasing amplitude. In other words, amplitude may be ramped upwards faster or slower than amplitude ramped downwards.

If the amplitude of the subsequent electrode combination has reached the target amplitude level, programmer 11 gradually reduces the amplitude of the first electrode combination 302A (332) to its end level, e.g., zero, while maintaining the amplitude of the subsequent combination at substantially the target amplitude. Although not illustrated in FIG. 28, programmer 11 may gradually reduce the amplitude of the first electrode combination in a series of increments, while maintaining the second combination at the target amplitude, in response to a series of user inputs. Then, programmer 11 turns on the next subsequent electrode combination 302C, and maintains the amplitude of the subsequent electrode combination 302B at the constant target level (316) while the amplitude of the next electrode combination 302C is increased gradually (318). Programmer 11 tests all the electrode combinations of the sequence, transitioning between each one in accordance with the process shown in FIG. 23. Again, the sequence may be a predefined sequence of adjacent or non-adjacent electrode combinations, or a sequence that is dynamically generated in response to input from the user.

Figure 29:
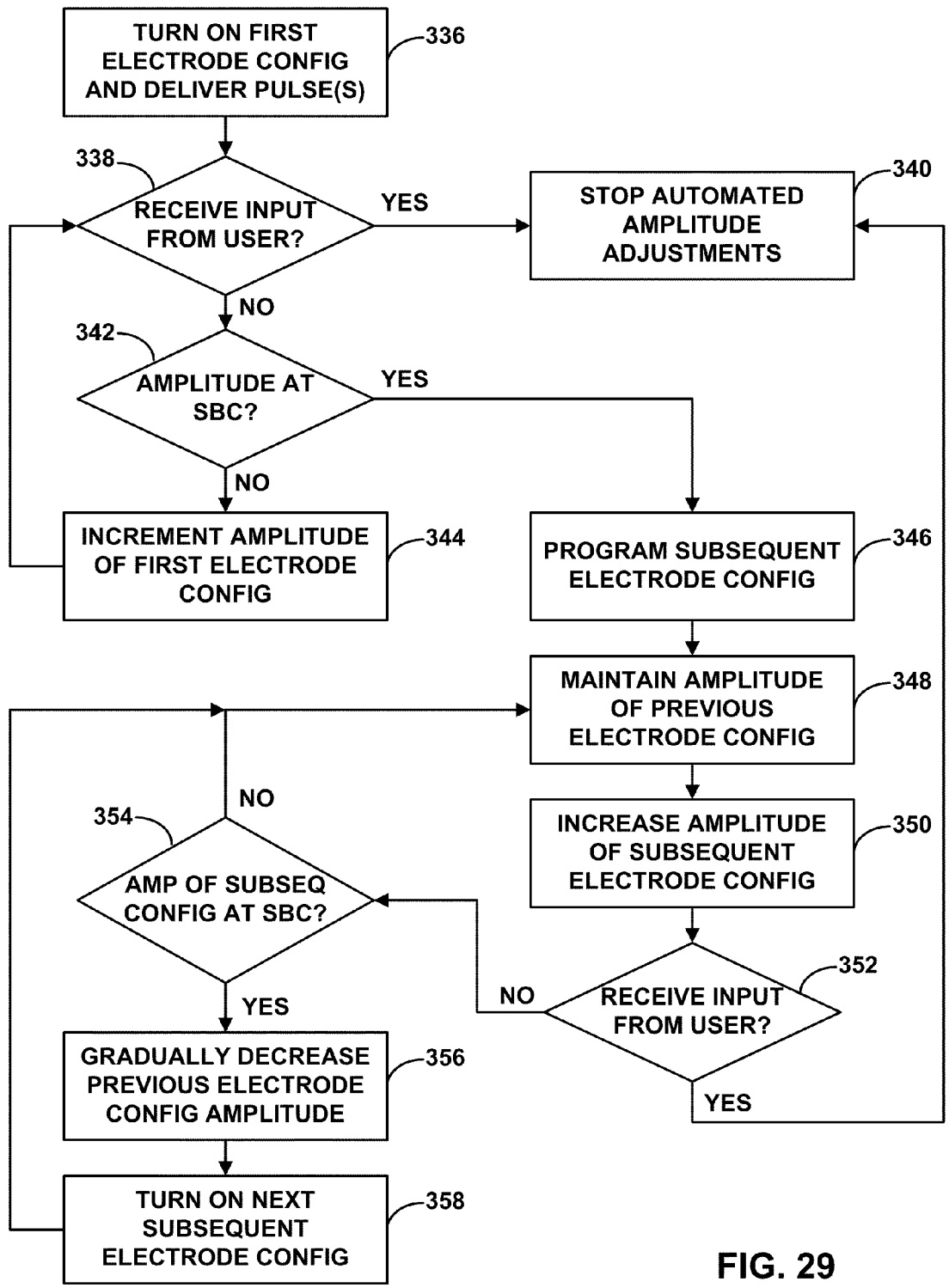
FIG. 29 is a flow diagram illustrating exemplary operation of programmer that receives input from a user to shift between electrode combinations in accordance with the alternative process of FIG. 23.

FIG. 29 is another flow diagram illustrating exemplary operation of a programmer that receives input from a user to shift between electrode combinations in accordance with the alternative process of FIG. 23. FIG. 29 generally corresponds to FIG. 10, but illustrates a different approach in which the amplitude of the previous electrode combination is maintained at a constant level during gradual increase of the amplitude of another electrode combination. The electrode combination testing in FIG. 29 is performed under user control, with the incremental adjustments occurring automatically until programmer 11 receives input from the user.

Initially, programmer 11 controls neurostimulator 14 to turn on a first electrode combination 301B and delivers one or more electrical pulses via the first electrode combination (336). Programmer 11 determines whether it has received input from the user indicating that the amplitude of the stimulation is uncomfortable (338). The user may, for example, be a physician, and the physician may actuate a button or other input media when a patient indicates that the stimulation is uncomfortable. Alternatively, the patient may actuate such a button. When programmer 11 receives input from the user indicating that the amplitude of the stimulation is uncomfortable, programmer 11 stops the automated amplitude adjustments (340).

When programmer 11 does not receive input from the user, programmer 11 determines whether the stimulation amplitude of the first electrode combination has reached the target amplitude or SBC level (342). The SBC level is a strong but comfortable (SBC) level, measured during a calibration stage, at which patient 12 notices a therapeutic stimulation effect without the therapy inducing pain or discomfort. The SBC level determined by calibration may serve as a target level. Alternatively, a predetermined target level may be used.

When the stimulation amplitude of the first electrode combination is below the target or SBC amplitude level, programmer 11 automatically increments the amplitude of the stimulation of the first electrode combination by a substep (344). Programmer 11 increases the amplitude by downloading a program update to the neurostimulator via telemetry. The automatic increases in amplitude may occur periodically at a rate of one every few seconds, so that there is sufficient spacing between the amplitude adjustments for the patient to distinguish different stimulation levels and have time to react in the event stimulation quickly becomes uncomfortable. In other embodiments, the rate may be slower or faster.

When the stimulation amplitude of the first electrode combination reaches the target amplitude, the programmer turns on a subsequent electrode combination (346). As described above, the subsequent electrode combination may be the next electrode combination in a pre-defined sequence of electrode combinations. In some embodiments, the subsequent electrode combination may be an adjacent electrode combination. Programmer 11 maintains the amplitude of the first electrode combination (348) at the substantially constant SBC level, and increases the amplitude of the subsequent electrode combination by a single substep (350). Programmer 11 interleaves the time slots during which stimulation pulses are provided to the first electrode combination and the subsequent electrode combination at a frequency that provides the patient with the feeling of a smooth transition between the electrode combinations.

Programmer 11 determines whether it has received input from the user indicating that the amplitude of the stimulation is uncomfortable after the step (352). When programmer 11 receives input from the user indicating the amplitude of the stimulation is uncomfortable, programmer 11 stops the automated amplitude adjustments (340). When programmer 11 does not receive input from the user, programmer 11 determines whether the amplitude of the subsequent electrode combination is at the SBC level (354). If the amplitude of the subsequent electrode combination has not reached the SBC level, programmer 11 maintains the amplitude of the previous electrode combination and incrementally increases the amplitude of the subsequent electrode combination, e.g., by one substep.

If the amplitude of the subsequent electrode combination has reached the SBC amplitude, programmer 11 gradually decreases the amplitude of the first electrode combination (356), e.g., by substeps to a zero amplitude or some other amplitude level, while maintaining the level of the second electrode combination, and then turns on the next subsequent electrode combination in the sequence (358). Programmer 11 begins to incrementally increases the amplitude of the next subsequent electrode combination while maintaining the amplitude of the previous electrode combination in the same manner. Programmer 11 tests the electrode combinations of the sequence, shifting between each one in accordance with the alternative technique outlined in FIG. 23. Programmer 11 may also concurrently monitor for mark input from the user for amplitude adjustment input from the user as described in detail in FIG. 28.

Figure 30:
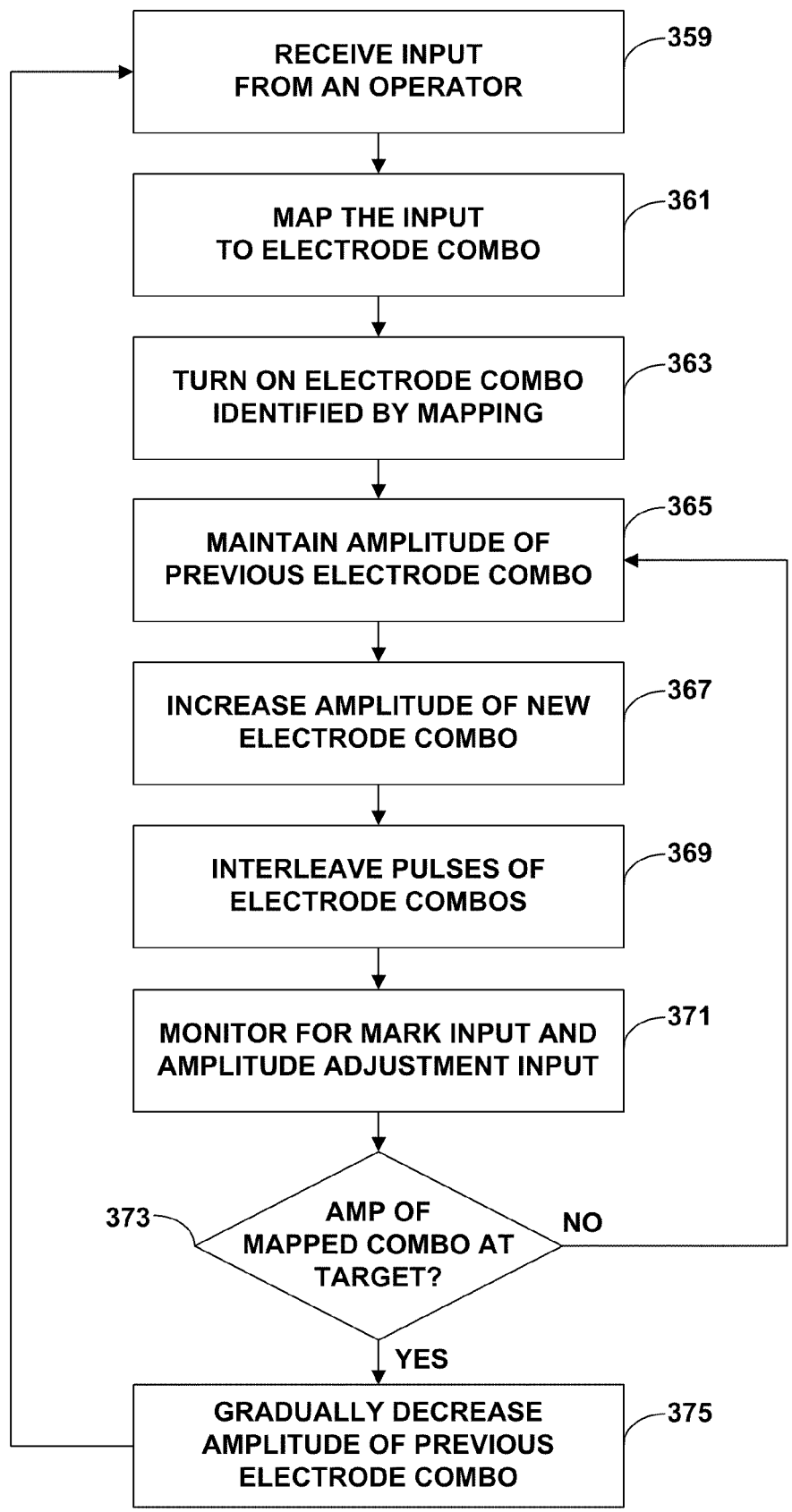
FIG. 30 is a flow diagram illustrating exemplary operation of programmer that receives input from a user to shift between electrode combinations in accordance with the alternative process of FIG. 23.

FIG. 30 is a flow diagram illustrating exemplary operation of a programmer that receives input from a user, such as programmer 50 of FIG. 5, shifting between electrode combinations in accordance with the alternative technique of FIG. 23. Initially, programmer 50 receives input from a user via controller 54 (359). Programmer 50 maps the manipulation of controller 54 to a particular electrode combination (361). As mentioned previously, programmer 50 may, for instance, access a map that maps X-Y coordinates of the directional controller to combinations of electrodes on leads 16. Alternatively, programmer 50 may use input from controller 54 to select successive electrode combinations, e.g., by array pointers, without regard to directional or location information.

Programmer 50 controls neurostimulator 14 to turn on the electrode combination identified by the mapping (363) and gradually increases the amplitude of the electrode combination to a target level. Programmer 50 maintains the amplitude of the first electrode combination (365) at the target amplitude, and gradually increases the amplitude of a subsequent electrode combination by a single substep (367). As described above, programmer 50 interleaves the time slots during which stimulation pulses are provided to the first electrode combination and the subsequent electrode combination (369).

Programmer 50 monitors for either mark input or amplitude adjustment input from the user (371). As described in detail above, mark input may be received when the user determines that a particular setting is efficacious. Upon receiving mark input, programmer 50 stores current parameter values, e.g., the amplitude values for one or both of the electrode combinations as well as the current target amplitude. Amplitude adjustment input may be received at any time during the shifting process, which may result in rescaling of the amplitude curves as described with respect to FIG. 26. Programmer 50 adjusts the overall intensity of the stimulation in response to receiving input from the user by adjusting one or both of the stimulation amplitudes of the first and subsequent electrode combinations as well as the target amplitude toward which programmer 50 is working.

Programmer 50 determines whether the stimulation amplitude of the newly mapped electrode combination has reached the target amplitude (373). When the stimulation amplitude of the mapped electrode combination is below the target amplitude, programmer 50 maintains the amplitude of the first electrode combination (365) at the target level and increases the amplitude of the subsequent electrode combination by another substep (367). Each incremental adjustment of stimulation amplitude may occur automatically, or be contingent on receiving input from the user. If the amplitude of the mapped electrode combination has reached the target amplitude, programmer 50 gradually decreases the amplitude of the first electrode combination (375) while maintaining the amplitude of the new electrode combination at the target level.

The gradual decreases (375) may be performed automatically, e.g., without user intervention, at a series of predetermined intervals. Alternatively, each incremental decrease may be performed in response to a user input. For example, a user may control progression of the amplitude increases and decreases for the first and second electrode combinations by a series of user inputs that specify substeps in amplitude adjustment. In some embodiments, the substeps may be taken forward or in reverse, as will be described in detail. As an illustration, a user may click an up, down, forward or reverse arrow repeatedly to increase the amplitude of one electrode combination and decrease the amplitude of another electrode combination in a series of controlled, incremental steps.

Figure 31:
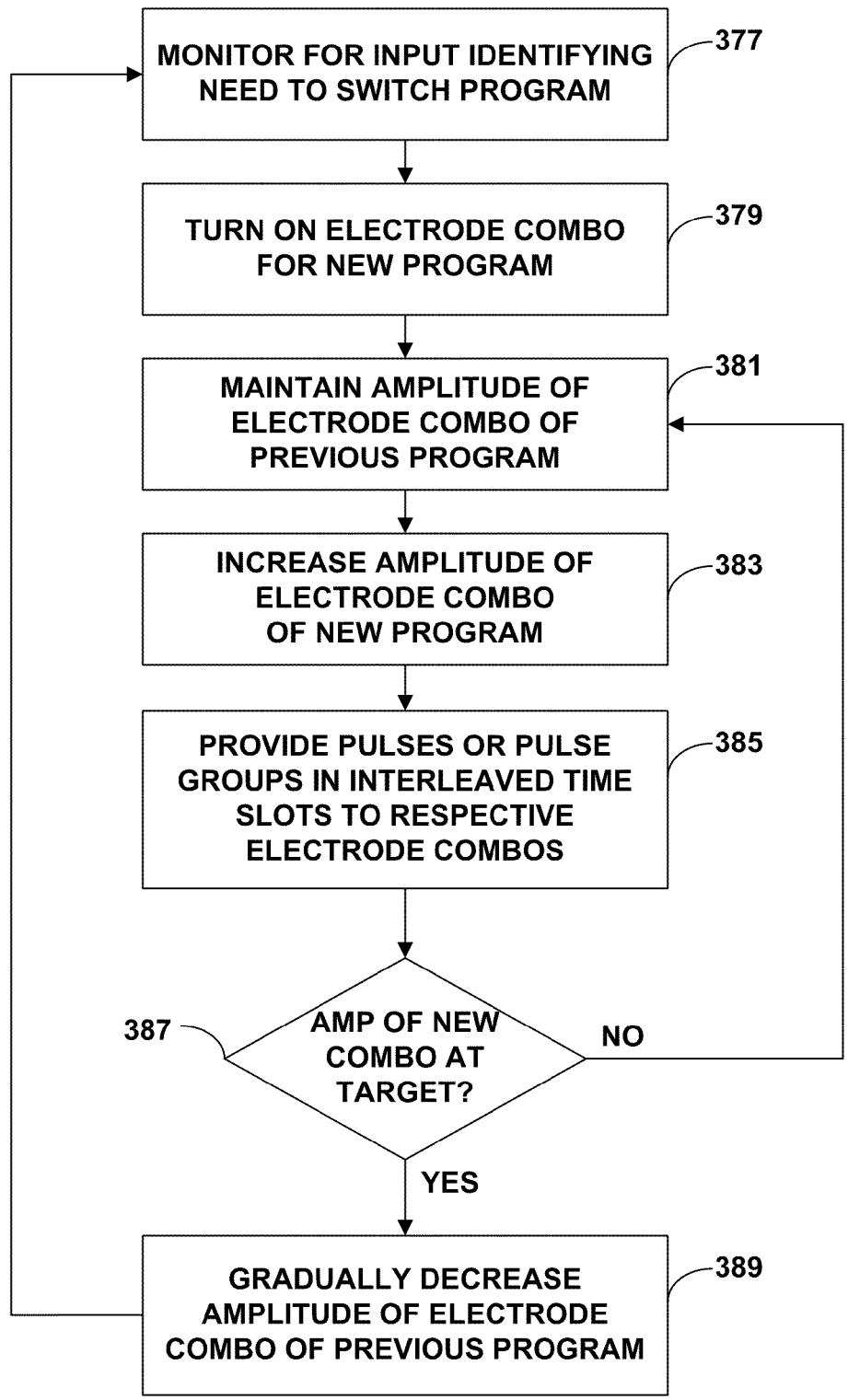
FIG. 31 is a flow diagram illustrating exemplary operation of a neurostimulator shifting between electrode combinations while switching neurostimulation therapy programs in accordance with the alternative process of FIG. 23.

FIG. 31 is a flow diagram illustrating exemplary operation of a neurostimulator, such as neurostimulator 14 of FIG. 1, shifting between electrode combinations while switching neurostimulation therapy programs according to the alternative technique shown in FIG. 23. Initially, neurostimulator 14 receives input identifying the need to switch between programs (377). As described with reference to FIG. 12, neurostimulator 14 may include one or more detectors that detect variables such as movement of a patient, heart rate of a patient or the like, and identify the need to switch between programs based on a change in one of the measured variables. Alternatively, neurostimulator 14 may receive input from a patient programmer indicating that the patient would like to change programs, or that the patient will be changing position or posture, and correlate that input with the need to switch therapy programs.

When neurostimulator 14 switches programs, it turns on the electrode combination associated with the new program (379). Neurostimulator 14 maintains the amplitude of the electrode combination associated with the previous program at a substantially constant target level (381) and increases the amplitude of the electrode combination associated with the subsequent program by an incremental step (383). Programmer 50 interleaves the time slots during which stimulation pulses are provided to electrode combinations (385).

Neurostimulator 14 determines whether the stimulation amplitude of the electrode combination associated with the new program has reached the target amplitude (387). If not, neurostimulator 14 maintains the amplitude of the electrode combination associated with the previous program at the substantially constant target level (381) and increases the amplitude of the electrode combination associated with the new program by another incremental substep (383). If the amplitude of the electrode combination associated with the new program has reached the target amplitude, neurostimulator 14 gradually reduces the amplitude of electrode combination associated with the previous program (389), and eventually turns off the previous electrode combination. Then, neurostimulator 14 maintains the amplitude of the current program, and monitors for the next input identifying a need to switch programs.

FIGS. 32-39 are graphs illustrating a shifting process in accordance with the alternative technique of FIG. 23 in conjunction with an exemplary screen shot 400 of a programmer illustrating a corresponding electrode diagram and stimulation parameters. In particular, FIGS. 32-39 illustrate progress along the amplitude shifting curves given a sequence of user inputs. In FIGS. 32-39, there are eighteen substeps, consistent with the example of FIG. 23, because some steps on the backside region may be skipped when going forward past the midpoint at which both electrode combinations are at the target level.

Figure 32:
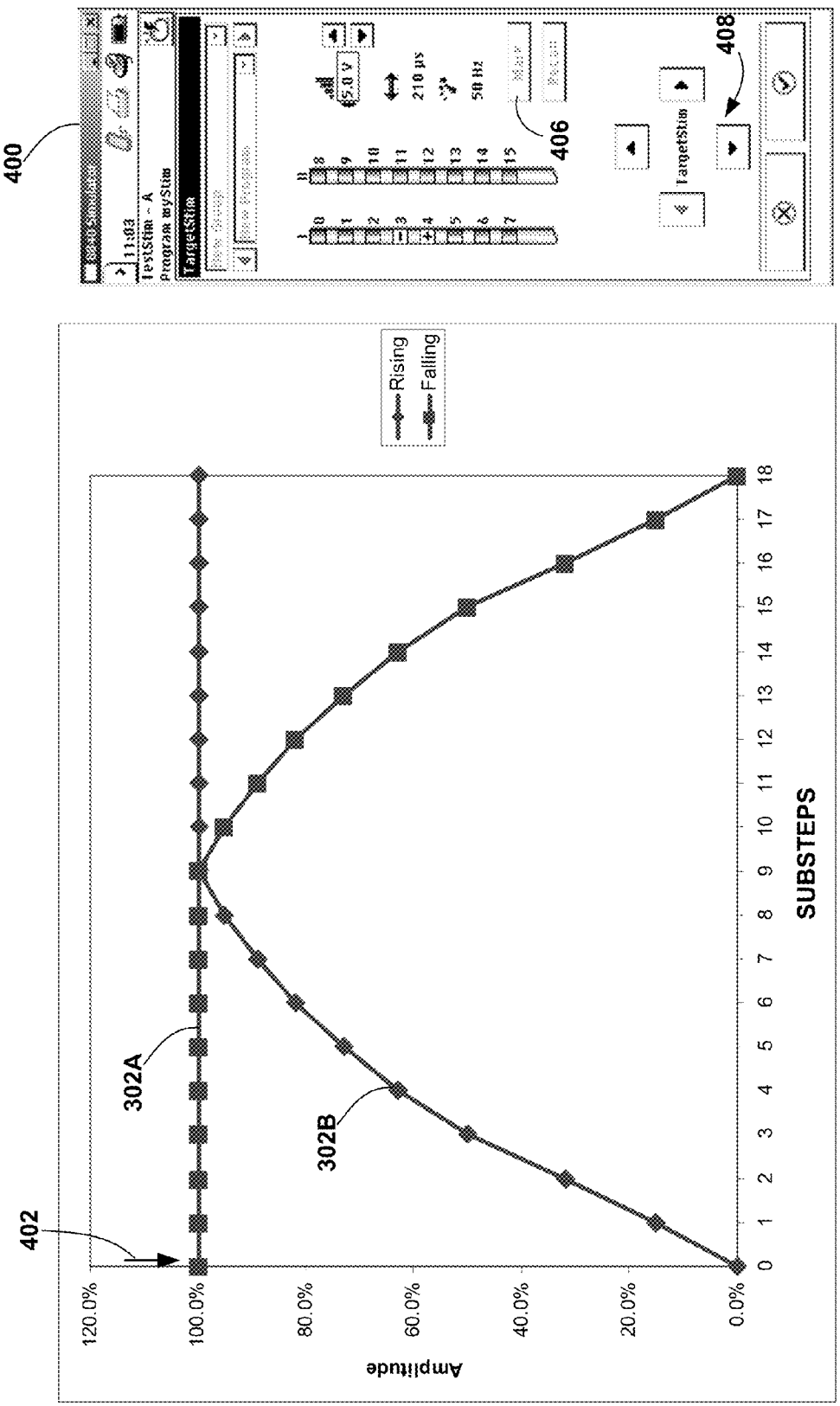
FIGS. 32-39 are graphs illustrating a shifting process in accordance with the alternative process of FIG. 23 in conjunction with an exemplary screen shot of a programmer illustrating a corresponding electrode diagram and stimulation parameters.

In the example of FIGS. 32-39, electrical stimulation energy is shifted from a first electrode combination 302A (Lead I: 3−, 4+) to a second electrode combination 302B (Lead I: 4−, 5+). FIGS. 32-39 show progression of the shifting process, including forward and reverse progression along the amplitude curves associated with electrode combinations 302A and 302B. As indicated by arrow 402, FIG. 32 represents the start of the shifting process, at which the amplitude of electrode combination 302A is at the target level, and the amplitude of electrode combination 302B is at an initial amplitude level, e.g., zero.

The programmer screen shot 400 in FIG. 32 illustrates allocation of all amplitude to the bipolar electrode combination of electrode 3 (−) and electrode 4 (+) on lead I. At this point, there is no progression of amplitude shifting to the next electrode combination formed by the bipolar electrode combination of electrode 4 (−) and electrode 5 (+). Screen shot 400 includes a diagram of leads and associated electrodes, current parameter settings, such as voltage or current amplitude (e.g., 5.0 V), pulse width (e.g., 210 microseconds), and pulse rate (e.g., 50 Hz). Screen shot 400 includes a mark input 406 to permit a patient to mark particular combinations, and input arrows 408 to permit shifting of stimulation energy among different electrode combinations.

Figure 33:
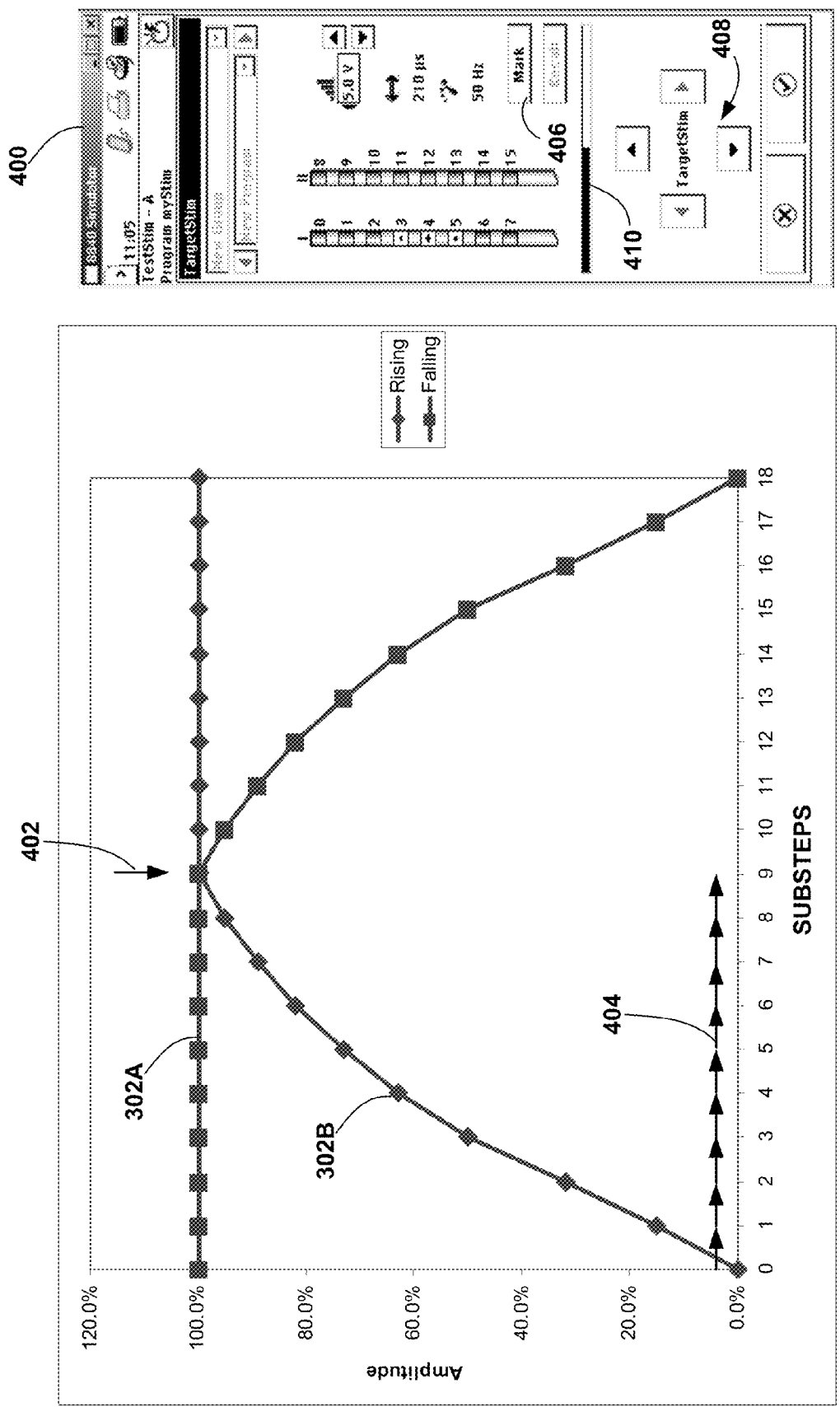

FIG. 33 represents the progression of the shifting process to the point that the amplitude of first electrode combination 302A, which has been maintained at the target level, and the amplitude of second electrode combination 302B are at the same target level. The extent of the progression is represented in terms of amplitude sub-steps by arrow 402 and arrows 404. Each arrow 404 represent a single substep. In the example of FIG. 33, the amplitude on electrode combination 302B has progressed nine substeps along the frontside region of the amplitude curve to the target level. In other words, the user has made nine substeps "down" the lead I, bringing the shifting program amplitudes for electrode combinations 302A and 302B to the midpoint of the curve, i.e., both are at the target amplitude After this midpoint, the amplitude on electrode combination 302A will begin to gradually decrease. In the screenshot 400 of FIG. 33, the size of the minus sign on electrode 3 has decreased, electrode 3 presents a combined plus and minus sign, and a small plus sign is visible in electrode 5, signifying the approximate midpoint of the transition between electrode combinations 302A and 302B. In addition, a progress bar 410 is provided to indicated the extent of the transition between electrode combinations 302A and 302B.

Figure 34:
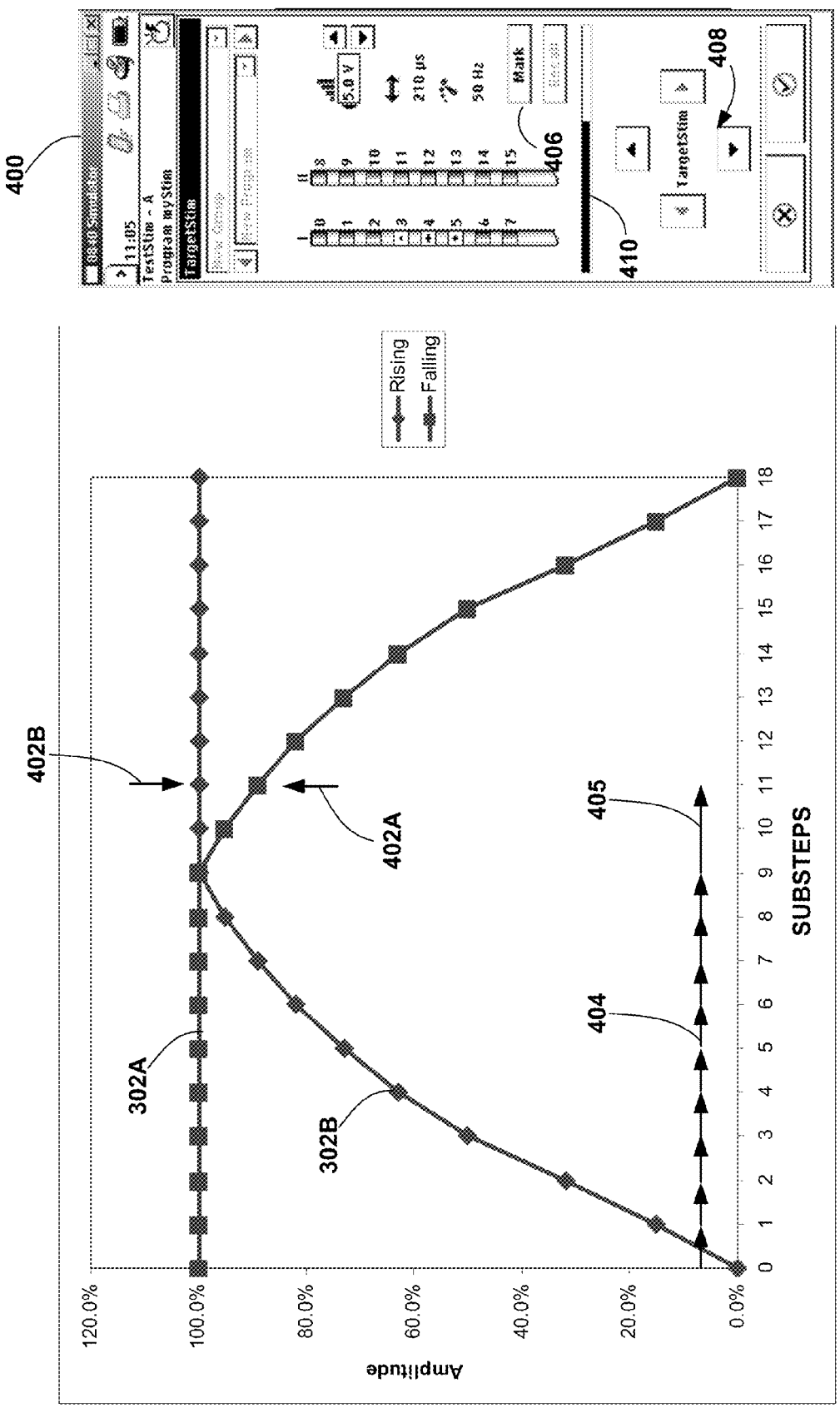

FIG. 34 represents the progression of the shifting process to the point that the amplitude of first electrode combination 302A has begun to gradually decrease along the backside region of its amplitude curve, as indicated by arrow 402A, while the amplitude of second electrode combination 302B is maintained at the substantially constant target level, as indicated by arrow 402B. Arrow 404 shows that the shifting has progressed by eleven substeps. As shown in the example of FIG. 34, the backside and frontside regions of electrode combinations 302A and 302B, respectively, appear symmetrical. When the amplitude curve is on the backside region, however, some of the backside substeps may be skipped such that the backside and frontside regions of electrode combinations 302A and 302B, respectively, are asymmetrical. In the example of FIG. 34, the progression from substep 9 to substep 11 represents a single substep, as substep 10 is skipped on the progression down the backside region. Arrow 405 represents the skipping of substep 10 so that the amplitude progresses directly from substep 9 to substep 11.

Figure 35:
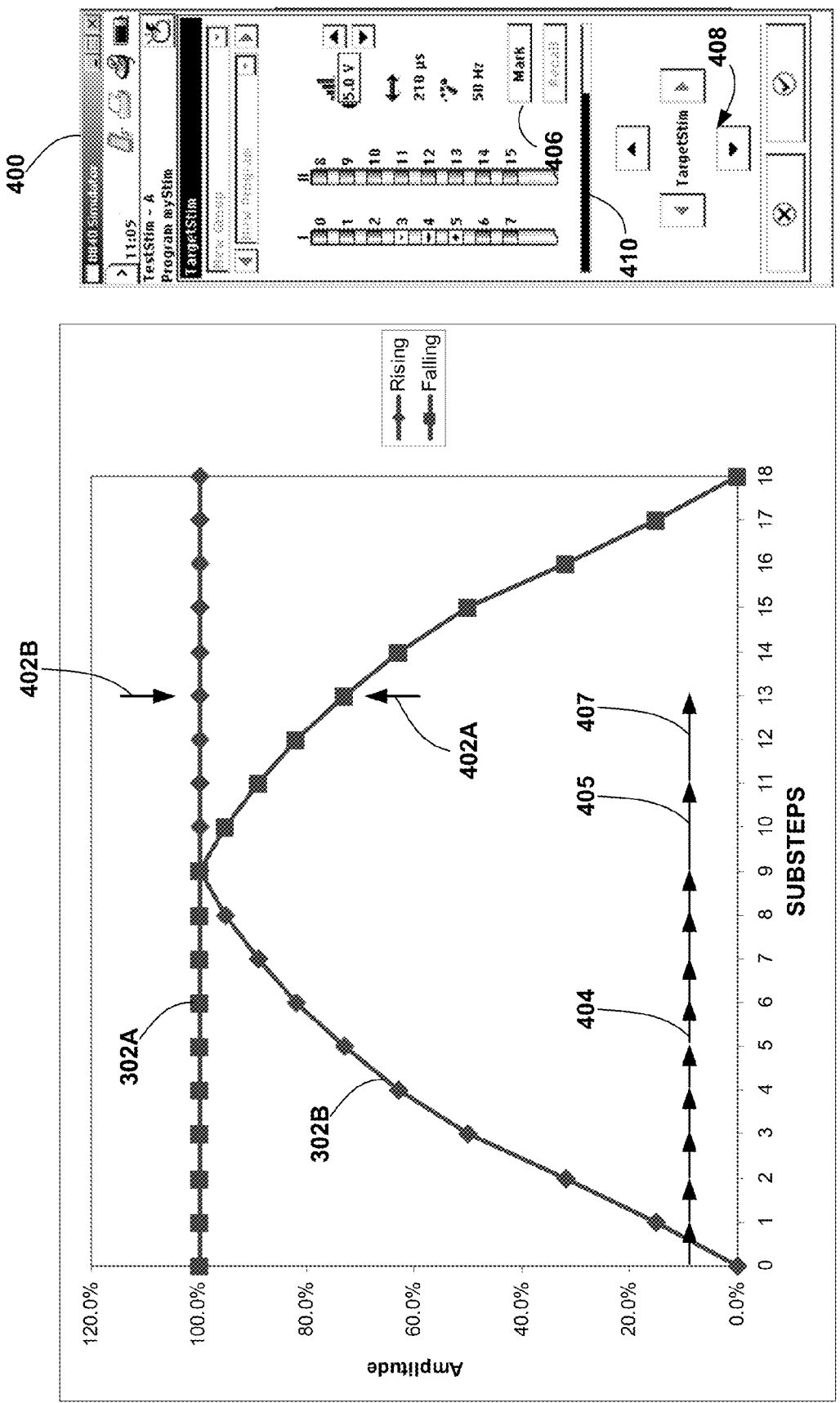

FIG. 35 represents the progression of the shifting process one more substep in the forward direction. With skipping of substep 12, the progression of FIG. 35 goes directly from substep 11 to substep 13, as indicated by arrow 407. With backside skipping, fourteen substeps (nine on the frontside and five on the backside) bring the progression to the next full step at substep 18). As the progression has passed the midpoint, progress bar 410 in screen shot 400 shows the progress if more than halfway along the length of the bar. In addition, the appearance of the plus and minus signs on the lead diagram changes. For example, the size of the minus sign on electrode 3 is diminished, the combined plus/minus sign on electrode 4 is more predominantly a minus sign, and the plus sign on electrode 5 is larger.

Figure 36:
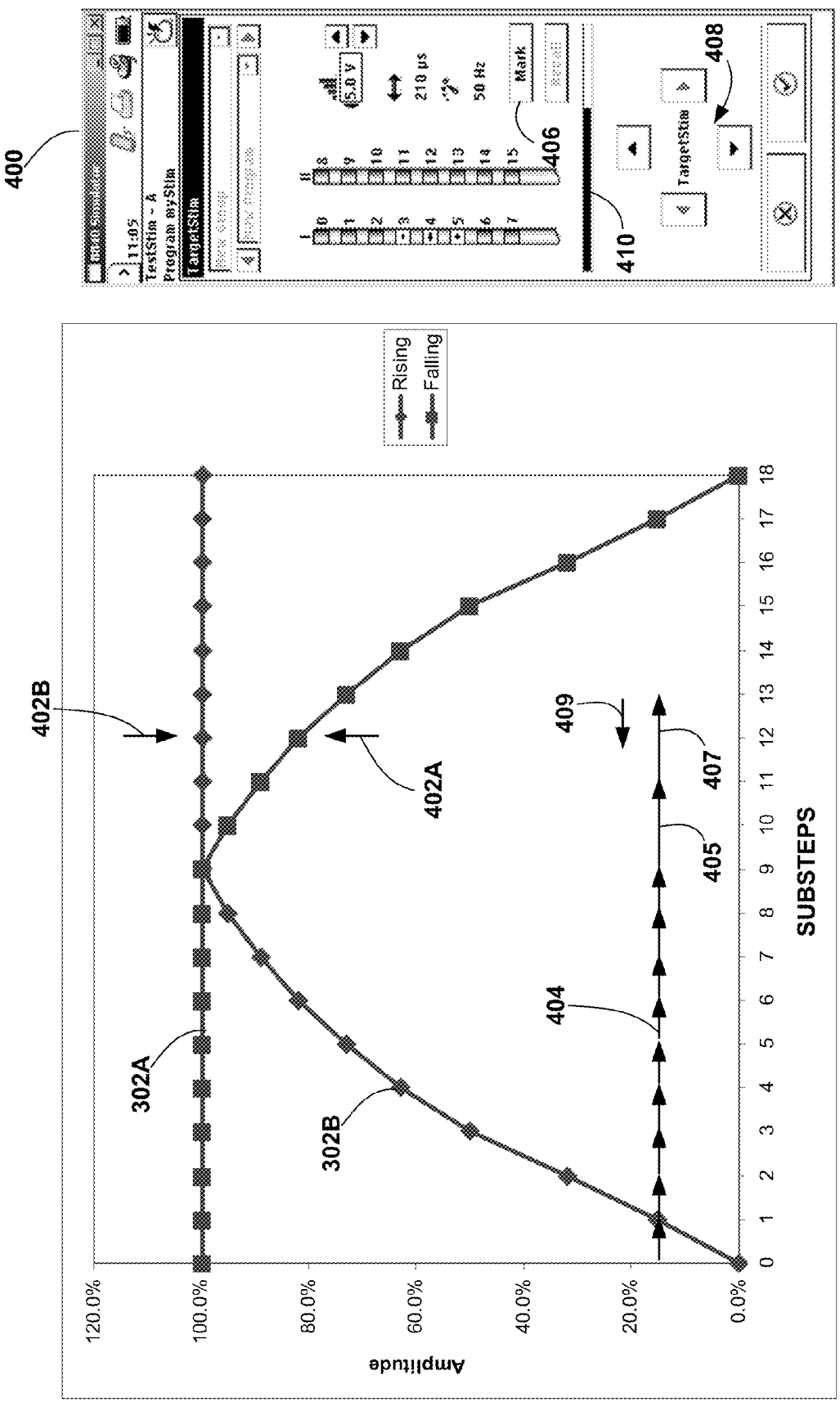

FIG. 36 represents the progression of the shifting process when the user moves one substep in the reverse direction. The sense of "reverse" depends on the initial movement direction. If the initial movement is to the right, i.e., from electrode combination 302A to electrode combination 302B, then "reverse" movements are to the left. Likewise, if the initial movement is to the left, i.e., from electrode combination 302B to electrode combination 302A, then "reverse" movements are to the right.

Although substeps are skipped in the backside region in the forward direction, substeps are not skipped in the backside region in the reverse direction. Accordingly, the amplitude curve progresses from substep 13 to substep 12, as indicated by arrow 409. In this case, the amplitude for electrode combination 402B remains at the target level, but the amplitude for electrode combination 402A increases by one substep. As shown in the graphs of FIGS. 32-39, amplitude may be expressed as a percentage of the target amplitude. The progress bar 410 and lead diagram change in appearance to match the reverse progress along the amplitude curve.

Figure 37:
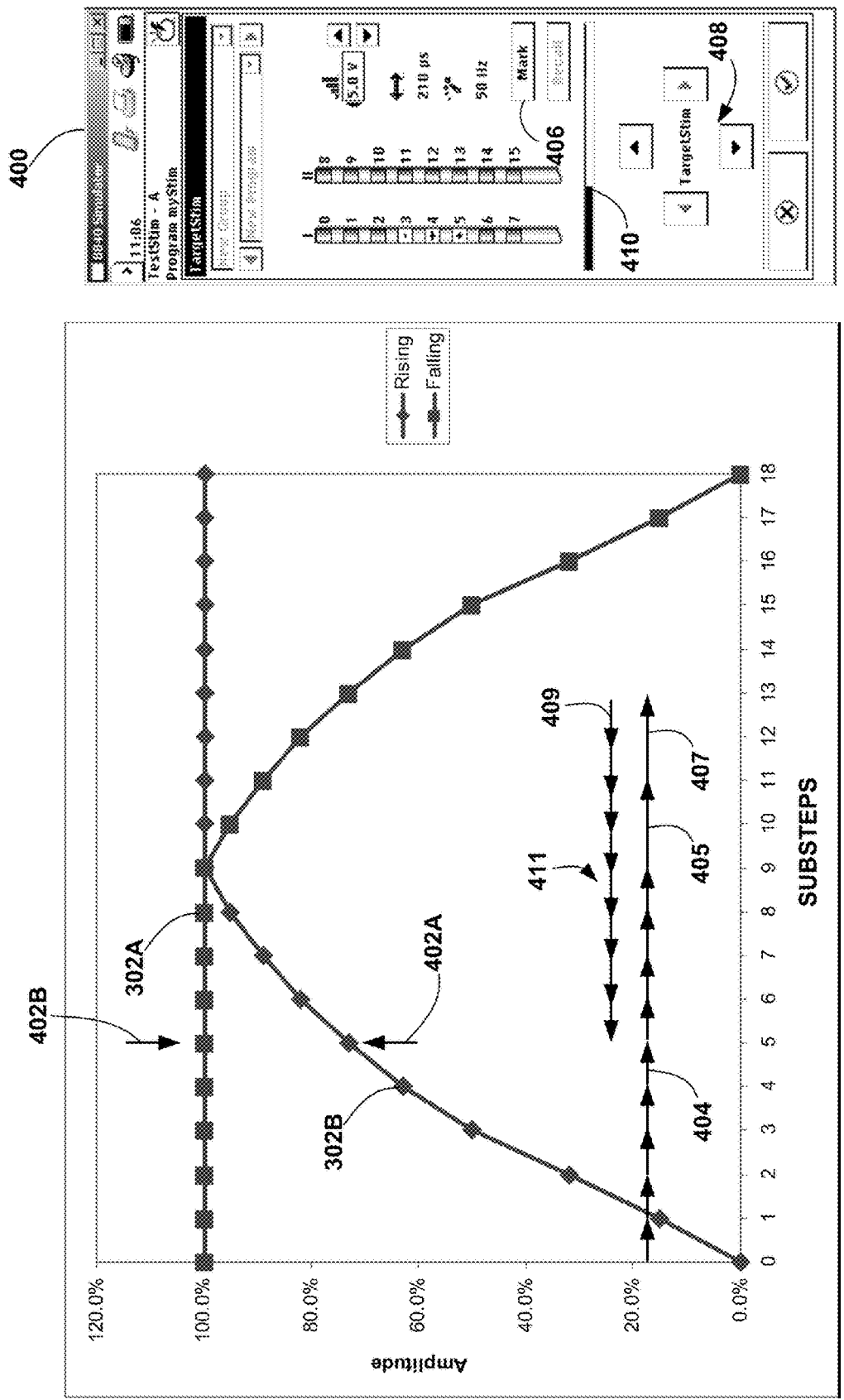

FIG. 37 shows progression of the shifting process when the user moves several additional substeps in the reverse direction, relative to FIG. 36. The reverse substeps are represented by arrows 411, and move the amplitude to substep 5. At substep 5, the amplitude for electrode combination 302B is maintained at the constant target level, while the amplitude for electrode combination 302B is at approximately 70% of the target amplitude level. In FIG. 37, there is no skipping of substeps in the reverse direction. Accordingly, each substep corresponds to a single substep. The progress bar 410 and lead diagram change in screen shot 400 in accordance with the progress represented by the amplitude curve in the graphs of FIG. 37.

Figure 38:
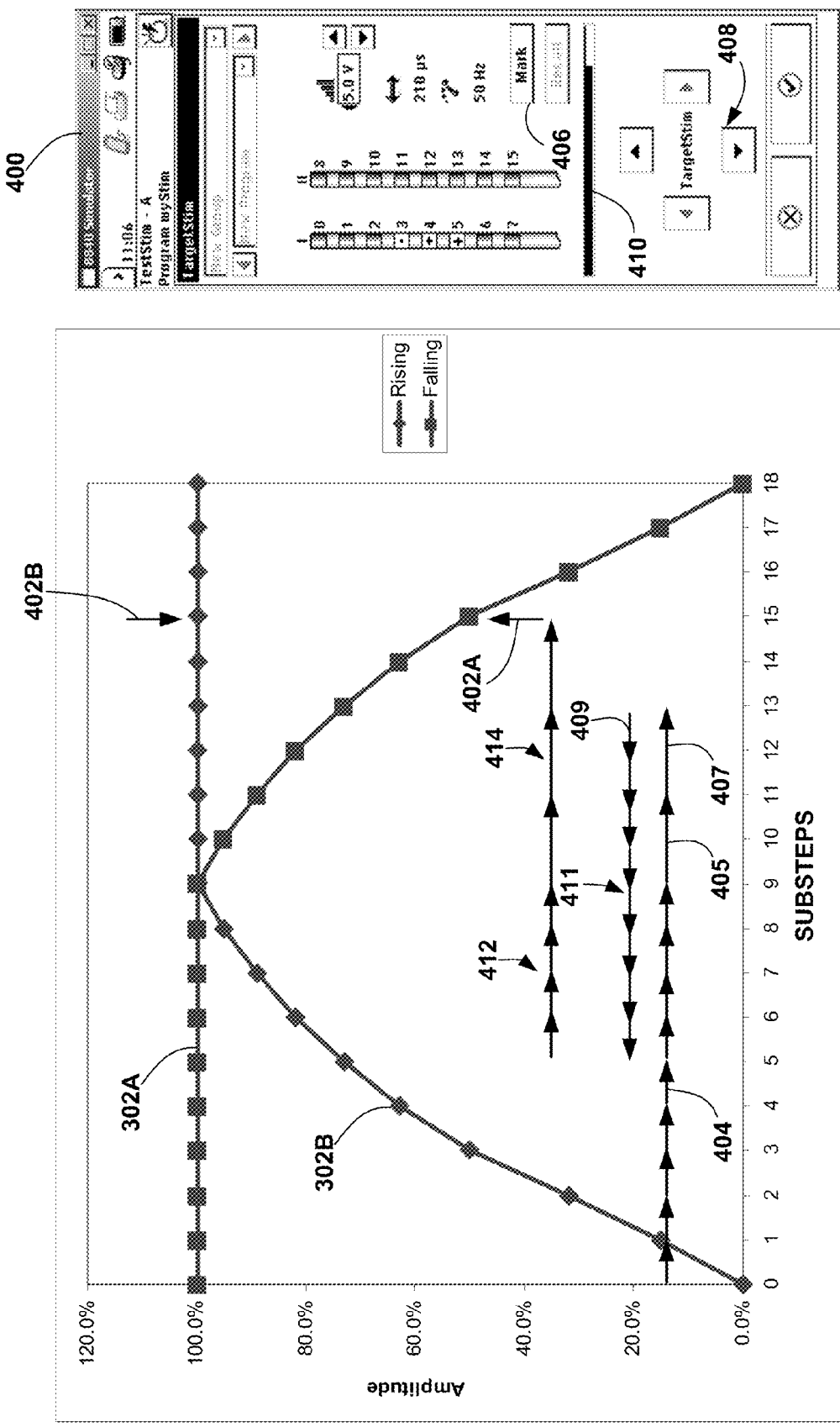

FIG. 38 shows progression of the shifting process when the user moves several substeps in the forward direction, from substep 5 to substep 15. The first four substeps, indicated by reference numeral 412, are single substeps from substep 5 to substep 9. As the substeps extend past substep 9, however, skipping of substeps applies. Skipping applies in the backside region of the amplitude curve as amplitude on electrode combination 302A decreases. Hence, the substeps between substep 9 and substep 15 are double substeps, represented by arrow 414. The progress bar 410 and lead diagram change in screen shot 400 in accordance with the progress represented by the amplitude curve in the graphs of FIG. 38.

Figure 39:
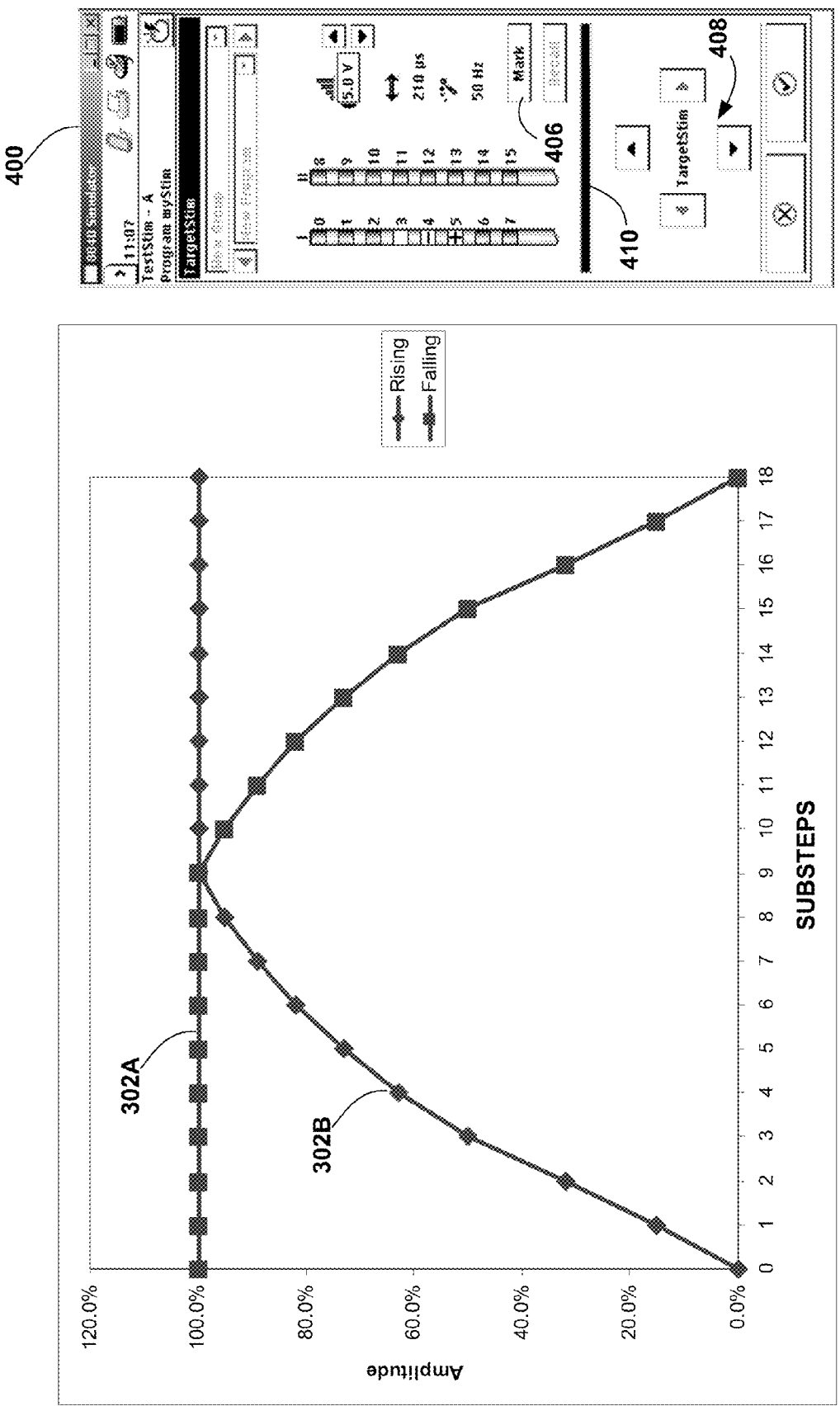

FIG. 39 shows completion of the transition of stimulation amplitude from electrode combination 302A to electrode combination 302B. As shown in FIG. 39, the amplitude of electrode combination 302B is at the target level, and the amplitude of electrode combination 302A is at the end level, e.g., zero. Screen shot 400 illustrates full transition of the amplitude shifting process. For example, electrodes 4 and 5 on lead I have full-sized minus and plus signs, respectively. In addition, the progress bar 410 shows progress along the entire length of the bar. Upon completion of the shifting process, the user may elect to shift amplitude from electrode combination 302B to another electrode combination, following a course similar to that shown in FIGS. 33-39.

Although this disclosure has referred to neurostimulation applications generally, and spinal cord stimulation applications more particularly, such applications have been described for purposes of illustration and should not be considered limiting of the invention as broadly embodied and described herein. The invention may be more generally applicable to electrical stimulation of tissue, such as nerve tissue or muscle tissue, and may be applicable to a variety of therapy applications including spinal cord stimulation, pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, Parkinson's disease, epilepsy, urinary or fecal incontinence, sexual dysfunction, obesity, or gastroparesis. Also, the invention is not necessarily limited to use with completely implanted neurostimulators, and may also be applicable to external stimulators coupled to implanted leads via a percutaneous port.

Various embodiments of the invention have been described. These and other embodiments are within the scope of the following claims.

The invention claimed is:

1. A method comprising:
   delivering electrical stimulation to a patient via a first subset of a plurality of electrodes;
   delivering electrical stimulation to the patient via a second subset of the electrodes; and
   receiving a signal representative of a time-domain user input that specifies incrementally adjusting a level of at least one of the electrical stimulation delivered to the patient via the first subset of the electrodes and the electrical stimulation delivered to the patient via the second subset of the electrodes.

2. The method of claim 1, wherein the time-domain user input comprises actuation of control inputs including play, rewind, stop, and fast-forward inputs.

3. The method of claim 2, wherein the control inputs each define a progression through a pre-defined sequence of steps, and wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

4. The method of claim 1, further comprising receiving the time-domain user input from a user of an external programmer, wherein the signal is received from the external programmer.

5. The method of claim 1, further comprising automatically proceeding through a pre-defined sequence of steps for incrementally adjusting the level of at least one of the electrical stimulation delivered to the patient via the first subset of the electrodes and the electrical stimulation delivered to the patient via the second subset of the electrodes until the signal representative of the time-domain user input is received.

6. The method of claim 1, further comprising, in response to receiving the signal representative of the time-domain user input, automatically proceeding through a pre-defined sequence of steps for incrementally adjusting the level of at least one of the electrical stimulation delivered to the patient via the first subset of the electrodes and the electrical stimulation delivered to the patient via the second subset of the electrodes.

7. The method of claim 1, wherein delivering electrical stimulation to the patient via the second subset of the electrodes comprises delivering electrical stimulation to the patient via the second subset of the electrodes on a time-interleaved basis with the electrical stimulation delivered via the first subset of the electrodes.

8. The method of claim 1, further comprising incrementally adjusting the level of at least one of the electrical stimulation delivered to the patient via the first subset of the electrodes and the electrical stimulation delivered to the patient via the second subset of the electrodes according to the received signal.

9. The method of claim 8, wherein incrementally adjusting the level of electrical stimulation comprises one of incrementally increasing or incrementally decreasing the level of electrical stimulation.

10. The method of claim 1, further comprising presenting a graph with a pre-defined sequence of steps via a user interface, wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

11. The method of claim 1, further comprising skipping one or more steps in a pre-defined sequence of steps when incrementally adjusting the level of electrical stimulation, wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

12. The method of claim 1, wherein a signal representative of the time-domain user input one of specifies the input in the time-domain or specifies the incremental adjustment predetermined by an external programmer based on time-domain user input from a user.

13. A medical device comprising:
means for delivering electrical stimulation to a patient via a first subset of a plurality of electrodes;
means for delivering electrical stimulation to the patient via a second subset of the electrodes; and
means for receiving a signal representative of a time-domain user input that specifies incrementally adjusting a level of at least one of the electrical stimulation delivered to the patient via the first subset of the electrodes and the electrical stimulation delivered to the patient via the second subset of the electrodes.

14. The medical device of claim 13, wherein the time-domain user input comprises actuation of control inputs including play, rewind, stop, and fast-forward inputs.

15. The medical device of claim 14, wherein the control inputs each define a progression through a pre-defined sequence of steps, and wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

16. The medical device of claim 13, further comprising means for automatically proceeding through a pre-defined sequence of steps for incrementally adjusting the level of at least one of the electrical stimulation delivered to the patient via the first subset of the electrodes and the electrical stimulation delivered to the patient via the second subset of the electrodes until the signal is received.

17. The medical device of claim 13, further comprising means for automatically proceeding through a pre-defined sequence of steps for incrementally adjusting the level of at least one of the electrical stimulation delivered to the patient via the first subset of the electrodes and the electrical stimulation delivered to the patient via the second subset of the electrodes in response to receiving the signal representative of the time-domain user input.

18. The medical device of claim 13, wherein the means for delivering electrical stimulation to the patient via the second subset of the electrodes comprises means for delivering electrical stimulation to the patient via the second subset of the electrodes on a time-interleaved basis with the electrical stimulation delivered via the first subset of the electrodes.

19. The medical device of claim 13, further comprising means for incrementally adjusting the level of at least one of the electrical stimulation delivered to the patient via the first subset of the electrodes and the electrical stimulation delivered to the patient via the second subset of the electrodes according to the time-domain user input.

20. The medical device of claim 19, wherein the means for incrementally adjusting the level of electrical stimulation comprises means for one of incrementally increasing or incrementally decreasing the level of electrical stimulation.

21. The medical device of claim 13, wherein the means for receiving the signal comprises means for receiving the signal from an external programmer configured to present a graph with a pre-defined sequence of steps, and wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

22. A medical device comprising:
an electrical stimulation generator configured to deliver electrical stimulation to a patient via a first subset of a plurality of electrodes and deliver electrical stimulation to the patient via a second subset of the electrodes; and
a controller configured to receive a signal representative of a time-domain user input that specifies incrementally adjusting a level of at least one of the electrical stimulation delivered to the patient via the first subset of the electrodes and the electrical stimulation delivered to the patient via the second subset of the electrodes.

23. The medical device of claim 22, wherein the time-domain user input comprises control inputs including play, rewind, stop, and fast-forward inputs.

24. The medical device of claim 23, wherein the control inputs each define a progression through a pre-defined sequence of steps, and wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

25. The medical device of claim 22, wherein the controller is configured to automatically proceed through a pre-defined sequence of steps for incrementally adjusting the level of at least one of the electrical stimulation delivered to the patient via the first subset of the electrodes and the electrical stimulation delivered to the patient via the second subset of the electrodes until the signal is received.

26. The medical device of claim 22, wherein the controller is configured to automatically proceed through a pre-defined sequence of steps for incrementally adjusting the level of at least one of the electrical stimulation delivered to the patient via the first subset of the electrodes and the electrical stimulation delivered to the patient via the second subset of the electrodes in response to receiving the signal representative of the time-domain user input.

27. The medical device of claim 22, wherein the electrical stimulation generator is configured to deliver electrical stimulation to the patient via the second subset of the electrodes on a time-interleaved basis with the electrical stimulation delivered via the first subset of the electrodes.

28. The medical device of claim 22, wherein the electrical stimulation generator is configured to incrementally adjust the level of at least one of the electrical stimulation delivered to the patient via the first subset of the electrodes and the electrical stimulation delivered to the patient via the second subset of the electrodes according to the time-domain user input.

29. The medical device of claim 28, wherein the electrical stimulation generator is configured to one of incrementally increase or incrementally decrease the level of electrical stimulation.

30. The medical device of claim 22, wherein the controller is configured to receive the signal from an external programmer comprising a user interface configured to present a graph with a pre-defined sequence of steps, and wherein the signal representative of the time-domain user input specifies incrementally adjusting the level of at least one of the electrical stimulation delivered to the patient via the first subset of the electrodes and the electrical stimulation delivered to the patient via the second subset of the electrodes along the pre-defined sequence of steps.

31. The medical device of claim 22, wherein the signal received by the controller is representative of a non-directional time-domain user input.

32. A method comprising:
delivering electrical stimulation to a patient via a first subset of a plurality of electrodes;
delivering electrical stimulation to the patient via a second subset of the electrodes; and
receiving a time-domain user input in an external programmer from a user, wherein the time-domain input specifies incrementally adjusting a level of at least one of the electrical stimulation delivered to the patient via the first subset of the electrodes and the electrical stimulation delivered to the patient via the second subset of the electrodes.

33. The method of claim 32, further comprising transmitting a signal representative of the time-domain user input to an implantable medical device configured to deliver electrical stimulation, wherein the signal specifies the incremental adjustment.

34. A system comprising:
an implantable medical device configured to deliver electrical stimulation to a patient via a first subset of a plurality of electrodes and deliver electrical stimulation to the patient via a second subset of the electrodes; and
an external programmer configured to receive a time-domain user input from a user, wherein the time-domain user input specifies incrementally adjusting a level of at least one of the electrical stimulation delivered to the patient via the first subset of the electrodes and the electrical stimulation delivered to the patient via the second subset of the electrodes.

35. The system of claim 34, wherein the external programmer is configured to transmit a signal representative of the time-domain user input to the implantable medical device, and wherein the signal specifies the incremental adjustment.

* * * * *